United States Patent
Colloca

(10) Patent No.: US 11,352,643 B2
(45) Date of Patent: *Jun. 7, 2022

(54) ENHANCED PROMOTER

(71) Applicant: GLAXOSMITHKLINE BIOLOGICALS SA, Rixensart (BE)

(72) Inventor: Stefano Colloca, Rome (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 120 days.

This patent is subject to a terminal disclaimer.

(21) Appl. No.: 16/756,373

(22) PCT Filed: Oct. 16, 2018

(86) PCT No.: PCT/EP2018/078242
§ 371 (c)(1),
(2) Date: Apr. 15, 2020

(87) PCT Pub. No.: WO2019/076892
PCT Pub. Date: Apr. 25, 2019

(65) Prior Publication Data
US 2021/0189420 A1   Jun. 24, 2021

Related U.S. Application Data

(60) Provisional application No. 62/572,927, filed on Oct. 16, 2017, provisional application No. 62/572,944, filed on Oct. 16, 2017, provisional application No. 62/572,951, filed on Oct. 16, 2017.

(51) Int. Cl.
*C12N 15/86* (2006.01)
*C12N 15/861* (2006.01)
*A61P 37/04* (2006.01)
*A61K 39/155* (2006.01)
*A61K 39/00* (2006.01)

(52) U.S. Cl.
CPC ............ *C12N 15/86* (2013.01); *A61K 39/155* (2013.01); *A61P 37/04* (2018.01); *A61K 2039/5256* (2013.01); *C12N 2710/10334* (2013.01); *C12N 2710/10343* (2013.01); *C12N 2830/001* (2013.01); *C12N 2840/44* (2013.01)

(58) Field of Classification Search
None
See application file for complete search history.

(56) References Cited

FOREIGN PATENT DOCUMENTS

WO     2017017050 A1     2/2017

OTHER PUBLICATIONS

International Search Report and Written Opinion for corresponding International Application No. PCT/EP2018/078242, dated Jan. 8, 2018 (9 pages).
Nitta et al., A CMV-actin-globin hybrid promoter improves adeno-associated viral vector gene expression in the arterial wall in vivo, Journal of Gene Medicine, 2005, p. 1348-1355, vol. 7.

*Primary Examiner* — Nicole Kinsey White
(74) *Attorney, Agent, or Firm* — Birch, Stewart, Kolasch & Birch, LLP

(57) ABSTRACT

A new promoter comprising: (i) an hCMV enhancer sequence; (ii) an hCMV promoter sequence; (iii) a splice donor region; (iv) a cell-derived enhancer sequence; and (v) a splice acceptor region.

16 Claims, 7 Drawing Sheets
Specification includes a Sequence Listing.

SEQUENCE LISTING

<160> NUMBER OF SEQ ID NOS: 14

<210> SEQ ID NO 1

<211> LENGTH: 37830
<212> TYPE: DNA
<213> ORGANISM: Chimpanzee adenovirus

<400> SEQUENCE: 1

```
catcatcaat aatatacctt attttggatt gaagccaata tgataatgag atgggcggcg      60
cggggcggga ggcgggtccg ggggcgggcc ggcgggcggg gcggtgtggc ggaagtggac     120
tttgtaagtg tggcggatgt gacttgctag tgccgggcgc ggtaaaagtg acgttttccg     180
tgcgcgacaa cgcccacggg aagtgacatt tttcccgcgg tttttaccgg atgttgtagt     240
gaatttgggc gtaaccaagt aagatttggc cattttcgcg ggaaaactga acgggggaag     300
tgaaatctga ttaatttcgc gttagtcata ccgcgtaata tttgtcgagg gccgagggac     360
tttggccgat tacgtggagg actcgcccag gtgttttttg aggtgaattt ccgcgttccg     420
ggtcaaagtc tccgttttat tattatagtc agctgacgcg gagtgtattt ataccctctg     480
atctcgtcaa gtggccactc ttgagtgcca gcgagtagag ttttctcctc tgccgctctc     540
cgctccgctc cgctcggctc tgacaccggg gaaaaaatga acatttcac ctacgatggc     600
ggtgtgctca ccggccagct ggctgctgaa gtcctggaca ccctgatcga ggaggtattg     660
gccgataatt atcctcccct gactccttt gagccaccta cacttcacga actctacgat     720
ctggatgtgg tggggcccag cgatccgaac gagcaggcgg tttccagttt ttttccagag     780
tccatgttgt tggccagcca ggaggggtc gaacttgaga cccctcctcc gatcgtggat     840
tcccccgatc cgccgcagct gactaggcag cccgagcgct gtgcgggacc tgagactatg     900
ccccagctgc tacctgaggt gatcgatctc acctgtaatg agtctggttt tccacccagc     960
gaggatgagg acgaagaggg tgagcagttt gtgttagatt ctgtggaaca acccgggcga    1020
ggatgcaggt cttgtcaata tcaccggaaa aacacaggag actcccagat tatgtgttct    1080
ctgtgttata tgaagatgac ctgtatgttt atttacagta agtttatcat ctgtgggcag    1140
gtgggctata gtgtgggtgg tggtctttgg ggggttttt aatatatgtc agggggttatg    1200
ctgaagactt ttttattgtg attttttaaag gtccagtgtc tgagcccgag caagaacctg    1260
aaccggagcc tgagccttct cgccccagga gaaagcctgt aatcttaact agacccagcg    1320
caccggtagc gagaggcctc agcagcgcgg agaccaccga ctccggtgct tcctcatcac    1380
ccccggagat tcaccccctg gtgccctgt gtcccgttaa gcccgttgcc gtgagagtca    1440
gtgggcggcg gtctgctgtg gagtgcattg aggacttgct ttttgattca caggaacctt    1500
tggacttgag cttgaaacgc cccaggcatt aaacctggtc acctgactg aatgagttga    1560
cgcctatgtt tgcttttgaa tgacttaatg tgtatagata ataagagtg agataatgtt    1620
ttaattgcat ggtgtgttta acttgggcgg agtctgctgg gtatataagc ttccctgggc    1680
taaacttggt tacacttgac ctcatggagg cctgggagtg tttggagaac tttgccggag    1740
ttcgtgcctt gctggacgag agctctaaca ataccctctg gtggtggagg tatttgtggg    1800
gctctccccca gggcaagtta gttttgtagaa tcaaggagga ttacaagtgg gaatttgaag    1860
agcttttgaa atcctgtggt gagctattgg attctttgaa tctaggccac caggctctct    1920
tccaggagaa ggtcatcagg actttggatt ttttccacacc ggggcgcatt gcagccgcgg    1980
ttgctttttct agcttttttg aaggatagat ggagcgaaga gacccacttg agttcgggct    2040
acgtcctgga ttttctggcc atgcaactgt ggagagcatg gatcagacac aagaacaggc    2100
tgcaactgtt gtcttccgtc cgcccgttgc tgattccggc ggaggagcaa caggccgggt    2160
cagaggaccg ggcccgtcgg gatccggagg agagggcacc gaggccgggc gagaggagcg    2220
```

```
cgctgaacct gggaaccggg ctgagcggcc atccacatcg ggagtgaatg tcgggcaggt   2280
ggtggatctt tttccagaac tgcggcggat tttgactatt agggaggatg ggcaatttgt   2340
taagggtctt aagagggaga gggggcttc tgagcataac gaggaggcca gtaatttagc    2400
ttttagcttg atgaccagac accgtccaga gtgcatcact tttcagcaga ttaaggacaa   2460
ttgtgccaat gagttggatc tgttgggtca gaagtatagc atagagcagc tgaccactta   2520
ctggctgcag ccgggtgatg atctggagga agctattagg gtgtatgcta aggtggccct   2580
gcggcccgat tgcaagtaca agctcaaggg gctggtgaat atcaggaatt gttgctacat   2640
ttctggcaac gggcggagg tggagataga gaccgaagac agggtggctt tcagatgcag    2700
catgatgaat atgtggccgg gggtgctggg catggacggg gtggtgatta tgaatgtgag   2760
gttcacgggg cccaacttta acggcacggt gttttttgggg aacaccaacc tggtcctgca  2820
cggggtgagc ttctatgggt ttaacaacac ctgtgtggag gcctggaccg atgtgaaggt   2880
ccgcggttgc gccttttatg gatgttggaa ggccatagtg agccgcccta agagcaggag   2940
ttccattaag aaatgcttgt ttgagaggtg caccttgggg atcctggccg agggcaactg   3000
cagggtgcgc cacaatgtgg cctccgagtg cggttgcttc atgctagtca agagcgtggc   3060
ggtaatcaag cataatatgg tgtgcggcaa cagcgaggac aaggcctcac agatgctgac   3120
ctgcacggat ggcaactgcc acttgctgaa gaccatccat gtaaccagcc acagccggaa   3180
ggcctggccc gtgttcgagc acaacttgct gacccgctgc tccttgcatc tgggcaacag   3240
gcgggggggt ttcctgccct atcaatgcaa ctttagtcac accaagatct tgctagagcc   3300
cgagagcatg tccaaggtga acttgaacgg ggtgttttgac atgaccatga agatctggaa  3360
ggtgctgagg tacgacgaga ccaggtcccg gtgcagaccc tgcgagtgcg ggggcaagca   3420
tatgaggaac cagcccgtga tgctggatgt gaccgaggag ctgaggacag accacttggt   3480
tctggcctgc accagggccg agtttggttc tagcgatgaa gacacagatt gaggtgggtg   3540
agtgggcgtg gcctgggggtg gtcatgaaaa tatataagtt gggggtctta gggtctcttt   3600
atttgtgttg cagagaccgc cggagccatg agcgggagca gcagcagcag cagtagcagc   3660
agcgccttgg atggcagcat cgtgagccct tatttgacga cgcggatgcc ccactgggcc   3720
ggggtgcgtc agaatgtgat gggctccagc atcgacggcc gacccgtcct gcccgcaaat   3780
tccgccacgc tgacctatgc gaccgtcgcg gggacgccgt tggacgccac cgccgccgcc   3840
gccgccaccg cagccgcctc ggccgtgcgc agcctggcca cggactttgc attcctggga   3900
ccactggcga caggggctac ttctcgggcc gctgctgccg ccgttcgcga tgacaagctg   3960
accgccctgc tggcgcagtt ggatgcgctt actcgggaac tgggtgacct ttctcagcag   4020
gtcatggccc tgcgccagca ggtctcctcc ctgcaagctg gcgggaatgc ttctcccaca   4080
aatgccgttt aagataaata aaaccagact ctgtttggat taaagaaaag tagcaagtgc   4140
attgctctct ttatttcata atttttccgcg cgcgataggc cctagaccag cgttctcggt   4200
cgttgagggt gcggtgtatc ttctccagga cgtggtagag gtggctctgg acgttgagat   4260
acatgggcat gagcccgtcc cggggtgga ggtagcacca ctgcagagct tcatgctccg    4320
gggtggtgtt gtagatgatc cagtcgtagc aggagcgctg gcatggtgc ctaaaaatgt    4380
ccttcagcag caggccgatg gccagggga ggcccttggt gtaagtgttt acaaaacggt    4440
taagttggga agggtgcatt cggggagaga tgatgtgcat cttggactgt attttttagat  4500
tggcgatgtt tccgcccaga tcccttctgg gattcatgtt gtgcaggacc accagtacag   4560
```

```
tgtatccggt gcacttgggg aatttgtcat gcagcttaga gggaaaagcg tggaagaact    4620
tggagacgcc tttgtggcct cccagatttt ccatgcattc gtccatgatg atggcaatgg    4680
gcccgcggga ggcagcttgg gcaaagatat ttctggggtc gctgacgtcg tagttgtgtt    4740
ccagggtgag gtcgtcatag gccattttta caaagcgcgg gcggagggtg cccgactggg    4800
ggatgatggt cccctctggc cctggggcgt agttgccctc gcagatctgc atttcccagg    4860
ccttaatctc ggagggggga atcatatcca cctgcggggc gatgaagaaa acggtttccg    4920
gagccgggga gattaactgg gatgagagca ggtttctaag cagctgtgat tttccacaac    4980
cggtgggccc ataaataaca cctataaccg gttgcagctg gtagtttaga gagctgcagc    5040
tgccgtcgtc ccggaggagg ggggccacct cgttgagcat gtccctgacg cgcatgttct    5100
ccccgaccag atccgccaga aggcgctcgc cgcccaggga cagcagctct tgcaaggaag    5160
caaagttttt cagcggcttg aggccgtccg ccgtgggcat gttttttcagg gtctggctca    5220 gcagctccag gcggtcccag agctcggtga cgtgctctac ggcatctcta tccagcatat    5280
ctcctcgttt cgcggggttgg ggcgactttc gctgtagggc accaagcggt ggtcgtccag    5340
cggggccaga gtcatgtcct tccatgggcg cagggtcctc gtcagggtgg tctgggtcac    5400
ggtgaagggg tgcgctccgg gctgagcgct tgccaaggtg cgcttgaggc tggttctgct    5460
ggtgctgaag cgctgccggt cttcgccctg cgcgtcggcc aggtagcatt tgaccatggt    5520
gtcatagtcc agccctccg cggcgtgtcc cttggcgcgc agcttgccct tggaggtggc    5580
gccgcacgag gggcagagca ggctcttgag cgcgtagagc ttggggggcga ggaagaccga    5640 ttcggggggag taggcgtccg cgccgcagac cccgcacacg gtctcgcact ccaccagcca    5700
ggtgagctcg gggcgcgccg ggtcaaaaac caggtttccc ccatgctttt tgatgcgttt    5760
cttacctcgg gtctccatga ggtggtgtcc ccgctcggtg acgaagaggc tgtccgtgtc    5820
tccgtagacc gacttgaggg gtcttttctc cagggggggtc cctcggtctt cctcgtagag    5880
gaactcggac cactctgaga cgaaggcccg cgtccaggcc aggacgaagg aggctatgtg    5940
ggaggggtag cggtcgttgt ccactagggg gtccaccttc tccaaggtgt gaagacacat    6000
gtcgccttcc tcggcgtcca ggaaggtgat tggcttgtag gtgtaggcca cgtgaccggg    6060
ggttcctgac gggggggtat aaaaggggt gggggcgcgc tcgtcgtcac tctcttccgc    6120
atcgctgtct gcgagggcca gctgctgggg tgagtattcc ctctcgaagg cgggcatgac    6180
ctccgcgctg aggttgtcag tttccaaaaa cgaggaggat ttgatgttca cctgtcccga    6240
ggtgatacct ttgagggtac ccgcgtccat ctggtcagaa acacgatctc ttttattgtc    6300
cagcttggtg gcgaacgacc cgtagagggc gttggagagc agcttggcga tggagcgcag    6360
ggtctggttc ttgtccctgt cggcgcgctc cttggccgcg atgttgagct gcacgtactc    6420
gcgcgcgacg cagcgccact cggggaagac ggtggtgcgc tcgtcgggca ccaggcgcac    6480 gcgcagccg cggttgtgca gggtgaccag gtccacgctg gtggcgacct cgccgcgcag    6540
gcgctcgttg gtccagcaga gacggccgcc cttgcgcgag cagaagggg gcaggggggtc    6600 gagctgggtc tcgtccgggg ggtccgcgtc cacggtgaaa ccccggggc gcaggcgcgc    6660 gtcgaagtag tctatcttgc aaccttgcat gtccagcgcc tgctgccagt cgcggggcgg    6720
gagcgcgcgc tcgtagggggt tgagcggcgg gccccagggc atgggggtggg tgagtgcgga    6780 ggcgtacatg ccgcagatgt catagacgta gaggggctcc cgcaggaccc cgatgtaggt    6840 gggggtagcag cggccgccgc ggatgctggc gcgcacgtag tcatacagct cgtgcgaggg    6900
ggcgaggagg tcggggccca ggttggtgcg ggcggggcgc tccgcgcgga agacgatctg    6960
```

```
cctgaagatg gcatgcgagt tggaagagat ggtggggcgc tggaagacgt tgaagctggc  7020
gtcctgcagg ccgacggcgt cgcgcacgaa ggaggcgtag gagtcgcgca gcttgtgtac  7080
cagctcggcg gtgacctgca cgtcgagcgc gcagtagtcg agggtctcgc ggatgatgtc  7140
atatttagcc tgccccttct ttttccacag ctcgcggttg aggacaaact cttcgcggtc  7200
tttccagtac tcttggatcg ggaaaccgtc cggttccgaa cggtaagagc ctagcatgta  7260
gaactggttg acggcctggt aggcgcagca gcccttctcc acggggaggg cgtaggcctg  7320
cgcggccttg cggagcgagg tgtgggtcag ggcgaaggtg tccctgacca tgactttgag  7380
gtactggtgc ttgaagtcgg agtcgtcgca gccgccccgc tcccagagcg agaagtcggt  7440
gcgcttcttg gagcggggt tgggcagagc gaaggtgaca tcgttgaaga ggattttgcc  7500
cgcgcggggc atgaagttgc gggtgatgcg gaagggcccc ggcacttcag gcggttgtt  7560 gatgacctgg gcggcgagca cgatctcgtc gaagccgttg atgttgtggc ccacgatgta  7620
gagttccagg aagcggggcc ggccctttac ggtgggcagc ttctttagct cttcgtaggt  7680
gagctcctcg ggcgaggcga ggccgtgctc ggccagggcc cagtccgcga ggtgcgggtt  7740
gtctctgagg aaggacttcc agaggtcgcg ggccaggagg tctgcaggc ggtctctgaa  7800 ggtcctgaac tggcggccca cggccatttt tcggggtg atgcagtaga aggtgagggg  7860
gtcttgctgc cagcggtccc agtcgagctg cagggcgagg tcgcgcgcgg cggtgaccag  7920
gcgctcgtcg cccccgaatt tcatgaccag catgaagggc acgagctgct tccgaaggc  7980 ccccatccaa gtgtaggtct ctacatcgta ggtgacaaag aggcgctccg tgcgaggatg  8040
cgagccgatc gggaagaact ggatctcccg ccaccagttg gaggagtggc tgttgatgtg  8100
gtggaagtag aagtcccgtc gccgggccga acactcgtgc tggcttttgt aaaagcgagc  8160
gcagtactgg cagcgctgca cgggctgtac ctcatgcacg agatgcacct ttcgcccgcg  8220
cacgaggaag ccgaggggaa atctgagccc ccgcctggc tcgcggcatg gctggttctc  8280
ttctactttg gatgcgtgtc cgtctccgtc tggctcctcg agggtgtta cggtggagcg  8340 gaccaccacg ccgcgcgagc cgcaggtcca gatatcggcg cgcggcggtc ggagtttgat  8400
gacgacatcg cgcagctggg agctgtccat ggtctgagc tcccgcggcg gcggcaggtc  8460
agccgggagt tcttgcaggt tcacctcgca gagtcgggcc agggcgcggg gcaggtctag  8520
gtggtacctg atctctaggg gcgtgttggt ggcggcgtcg atggcttgca ggagcccgca  8580
gccccggggg gcgacgacgg tgccccgcgg ggtggtggtg gtggtggcgg tgcagctcag  8640
aagcggtgcc gcgggcgggc ccccggaggt aggggggggct ccggtcccgc gggcagggc  8700 ggcagcggca cgtcggcgtg gagcgcgggc aggagttggt gctgtgcccg gaggttgctg  8760
gcgaaggcga cgacgcggcg gttgatctcc tggatctggc gcctctgcgt gaagacgacg  8820
ggcccggtga gcttgaacct gaaagagagt tcgacagaat caatctcggt gtcattgacc  8880
gcggcctggc gcaggatctc ctgcacgtct cccgagttgt cttggtaggc gatctcggcc  8940
atgaactgct cgatctcttc ctcctggagg tctccgcgtc cggcgcgttc cacggtggcc  9000
gccaggtcgt tggagatgcg ccccatgagc tgcgagaagg cgttgagtcc gccctcgttc  9060
cagactcggc tgtagaccac gccccctgg tcatcgcggg cgcgcatgac cacctgcgcg  9120
aggttgagct ccacgtgccg cgcgaagacg gcgtagttgc gcagacgctg gaagaggtag  9180
ttgagggtgg tggcggtgtg ctcggccacg aagaagttca tgacccagcg gcgcaacgtg  9240
gattcgttga tgtcccccaa ggcctccagc cgttccatgg cctcgtagaa gtccacggcg  9300
```

```
aagttgaaaa actgggagtt gcgcgccgac acggtcaact cctcctccag aagacggatg      9360
agctcggcga cggtgtcgcg cacctcgcgc tcgaaggcta tggggatctc ttcctccgct      9420
agcatcacca cctcctcctc ttcctcctct tctggcactt ccatgatggc ttcctcctct      9480 tcgggggggtg gcggcggcgg cggtggggga ggggggcgctc tgcgccggcg gcggcgcacc    9540
gggaggcggt ccacgaagcg cgcgatcatc tccccgcggc ggcggcgcat ggtctcggtg      9600
acggcgcggc cgttctcccg ggggcgcagt tggaagacgc cgccggacat ctggtgctgg      9660
ggcgggtggc cgtgaggcag cgagacggcg ctgacgatgc atctcaacaa ttgctgcgta      9720
ggtacgccgc cgagggacct gagggagtcc atatccaccg gatccgaaaa cctttcgagg      9780
aaggcgtcta accagtcgca gtcgcaaggt aggctgagca ccgtggcggg cggcgggggg      9840 tgggggagt gtctggcgga ggtgctgctg atgatgtaat tgaagtaggc ggacttgaca      9900
cggcggatgg tcgacaggag caccatgtcc ttgggtccgg cctgctggat gcggaggcgg      9960
tcggctatgc cccaggcttc gttctggcat cggcgcaggt ccttgtagta gtcttgcatg     10020
agcctttcca ccggcacctc ttctccttcc tcttctgctt cttccatgtc tgcttcggcc     10080
ctggggcggc gccgcgcccc ctgcccccc atgcgcgtga ccccgaaccc cctgagcggt       10140
tggagcaggg ccaggtcggc gacgacgcgc tcggccagga tggcctgctg cacctgcgtg     10200
agggtggttt ggaagtcatc caagtccacg aagcggtggt aggcgcccgt gttgatggtg     10260
taggtgcagt tggccatgac ggaccagttg acggtctggt ggcccggttg cgacatctcg     10320
gtgtacctga gtcgcgagta ggcgcgggag tcgaagacgt agtcgttgca agtccgcacc     10380
aggtactggt agcccaccag gaagtgcggc ggcggctggc ggtagagggg ccagcgcagg     10440
gtggcggggg ctccgggggc caggtcttcc agcatgaggc ggtggtaggc gtagatgtac     10500
ctggacatcc aggtgatacc cgcggcggtg gtggaggcgc gcgggaagtc gcgcacccgg     10560
ttccagatgt tgcgcagggg cagaaagtgc tccatggtag gcgtgctctg tccagtcaga     10620
cgcgcgcagt cgttgatact ctagaccagg gaaaacgaaa gccggtcagc gggcactctt     10680
ccgtggtctg gtgaatagat cgcaagggta tcatggcgga gggcctcggt tcgagccccg     10740
ggtccgggcc ggacggtccg ccatgatcca cgcggttacc gcccgcgtgt cgaacccagg     10800
tgtgcgacgt cagacaacgg tggagtgttc cttttggcgt ttttctggcc gggcgccggc     10860
gccgcgtaag agactaagcc gcgaaagcga aagcagtaag tggctcgctc cccgtagccg     10920
gagggatcct tgctaagggt tgcgttgcgg cgaacccgg ttcgaatccc gtactcgggc      10980
cggccggacc cgcggctaag gtgttggatt ggcctccccc tcgtataaag accccgcttg    11040
cggattgact ccggacacgg ggacgagccc cttttatttt tgctttcccc agatgcatcc    11100
ggtgctgcgg cagatgcgcc ccccgcccca gcagcagcaa caacaccagc aagagcggca    11160
gcaacagcag cgggagtcat gcagggcccc ctcacccacc ctcggcgggc cggccacctc    11220
ggcgtccgcg gccgtgtctg gcgcctgcgg cggcggcggg gggccggctg acgaccccga    11280
ggagcccccg cggcgcaggg ccagacacta cctggacctg gaggagggcg agggcctggc    11340
gcggctgggg gcgccgtctc ccgagcgcca cccgcgggtg cagctgaagc gcgactcgcg    11400
cgaggcgtac gtgcctcggc agaacctgtt cagggaccgc gcgggcgagg agcccgagga    11460
gatgcgggac aggaggttca gcgcagggcg ggagctgcgg caggggctga accgcgagcg    11520
gctgctgcgc gaggaggact ttgagcccga cgcgcggacg gggatcagcc ccgcgcgcgc    11580
gcacgtggcg gccgccgacc tggtgacggc gtacgagcag acggtgaacc aggagatcaa    11640
cttccaaaag agtttcaaca accacgtgcg cacgctggtg gcgcgcgagg aggtgaccat    11700
```

```
cgggctgatg cacctgtggg actttgtaag cgcgctggtg cagaacccca acagcaagcc   11760
tctgacggcg cagctgttcc tgatagtgca gcacagcagg acaacgagg cgtttaggga    11820 cgcgctgctg aacatcaccg agcccgaggg tcggtggctg ctggacctga ttaacatcct   11880
gcagagcata gtggtgcagg agcgcagcct gagcctggcc gacaaggtgg cggccatcaa   11940
ctactcgatg ctgagcctgg gcaagtttta cgcgcgcaag atctaccaga cgccgtacgt   12000
gcccatagac aaggaggtga agatcgacgg ttttttacatg cgcatggcgc tgaaggtgct   12060
caccctgagc gacgacctgg gcgtgtaccg caacgagcgc atccacaagg ccgtgagcgt   12120
gagccggcgg cgcgagctga gcgaccgcga gctgatgcac agcctgcagc gggcgctggc   12180
gggcgccggc agcggcgaca gggaggcgga gtcctacttc gatgcggggg cggacctgcg   12240
ctgggcgccc agccggcggg ccctggaggc gcgggggtc cgcgaggact atgacgagga    12300
cggcgaggag gatgaggagt acgagctaga ggagggcgag tacctggact aaaccgcggg   12360
tggtgtttcc ggtagatgca agacccgaac gtggtggacc cggcgctgcg ggcggctctg   12420
cagagccagc cgtccggcct taactcctca gacgactggc gacaggtcat ggaccgcatc   12480
atgtcgctga cggcgcgtaa cccggacgcg ttccggcagc agccgcaggc caacaggctc   12540
tccgccatcc tggaggcggt ggtgcctgcg cgctcgaacc ccacgcacga aaggtgctg    12600 gccatagtga acgcgctggc cgagaacagg gccatccgcc cggacgaggc cgggctggtg   12660
tacgacgcgc tgctgcagcg cgtggcccgc tacaacagcg gcaacgtgca gaccaacctg   12720
gaccggctgg tggggacgt gcgcgaggcg tggcgcagc gcgagcgcgc ggatcggcag     12780
ggcaacctgg gctccatggt ggcgctgaat gccttcctga gcacgcagcc ggccaacgtg   12840
ccgcgggggc aggaagacta caccaacttt gtgagcgcgc tgcggctgat ggtgaccgag   12900 acccccaga gcgaggtgta ccagtcgggc ccggactact tcttccagac cagcagacag    12960
ggcctgcaga cggtgaacct gagccaggct ttcaagaacc tgcgggggct gtgggcgtg    13020 aaggcgccca ccggcgaccg ggcgacggtg tccagcctgc tgacgcccaa ctcgcgcctg   13080
ctgctgctgc tgatcgcgcc gttcacggac agcggcagcg tgtcccggga cacctacctg   13140
gggcacctgc tgaccctgta ccgcgaggcc atcgggcagg cgcaggtgga cgagcacacc   13200
ttccaggaga tcaccagcgt gagccgcgcg ctggggcagg aggacacgag cagcctggag   13260
gcgactctga actacctgct gaccaaccgg cggcagaaga ttccctcgct gcacagcctg   13320
acctccgagg aggagcgcat cttgcgctac gtgcagcaga gcgtgagcct gaacctgatg   13380
cgcgacgggg tgacgcccag cgtggcgctg gacatgaccg cgcgcaacat ggaaccgggc   13440
atgtacgccg cgcaccggcc ttacatcaac cgcctgatgg actacctgca tcgcgcggcg   13500
gccgtgaacc ccgagtactt taccaacgcc atcctgaacc cgcactggct cccgccgccc   13560
gggttctaca gcggggcttc gaggtcccg gagaccaacg atggcttcct gtgggacgac    13620
atggacgaca gcgtgttctc cccgcggccg caggcgctgg cggaagcgtc cctgctgcgt   13680
cccaagaagg aggaggagga ggaggcgagt cgccgccgcg gcagcagcgg cgtggcttct   13740
ctgtccgagc tggggcggc agccgccgcg cgccccgggt ccctgggcgg cagccccttt   13800
ccgagcctgg tggggtctct gcacagcgag cgcaccaccc gccctcggct gctgggcgag   13860
gacgagtacc tgaataactc cctgctgcag ccggtgcggg agaaaaacct gcctcccgcc   13920
ttccccaaca acgggataga gagcctggtg gacaagatga gcagatggaa gacctatgcg   13980
caggagcaca gggacgcgcc tgcgctccgg ccgcccacgc ggcgccagcg ccacgaccgg   14040
```

```
cagcggggc  tggtgtggga  tgacgaggac  tccgcggacg  atagcagcgt  gctggacctg   14100
ggagggagcg  gcaacccgtt  cgcgcacctg  cgccccgcc   tggggaggat  gttttaaaaa   14160
aaaaaaaaaa  aagcaagaag  catgatgcaa  aaattaaata  aaactcacca  aggccatggc   14220
gaccgagcgt  tggtttcttg  tgttcccttc  agtatgcggc  gcgcggcgat  gtaccaggag   14280
ggacctcctc  cctcttacga  gagcgtggtg  ggcgcggcgg  cggcggcgcc  ctcttctccc   14340
tttgcgtcgc  agctgctgga  gccgccgtac  gtgcctccgc  gctacctgcg  gcctacgggg   14400
gggagaaaca  gcatccgtta  ctcggagctg  gcgcccctgt  tcgacaccac  ccgggtgtac   14460
ctggtggaca  caagtcggc   ggacgtggcc  tccctgaact  accagaacga  ccacagcaat   14520
tttttgacca  cggtcatcca  gaacaatgac  tacagcccga  gcgaggccag  cacccagacc   14580
atcaatctgg  atgaccggtc  gcactggggc  ggcgacctga  aaccatcct   gcacaccaac   14640 atgcccaacg  tgaacgagtt  catgttcacc  aataagttca  aggcgcgggt  gatggtgtcg   14700
cgctcgcaca  ccaaggaaga  ccgggtggag  ctgaagtacg  agtgggtgga  gttcgagctg   14760
ccagagggca  actactccga  gaccatgacc  attgacctga  tgaacaacgc  gatcgtggag   14820
cactatctga  aagtgggcag  gcagaacggg  gtcctggaga  gcgacatcgg  ggtcaagttc   14880
gacaccagga  acttccgcct  ggggctggac  cccgtgaccg  ggctggttat  gcccggggtg   14940
tacaccaacg  aggccttcca  tcccgacatc  atcctgctgc  ccggctgcgg  ggtggacttc   15000
acttacagcc  gctgagcaa   cctcctgggc  atccgcaagc  ggcagcccct  tccaggagggc  15060 ttcaggatca  cctacgagga  cctggagggg  ggcaacatcc  ccgcgctcct  cgatgtggag   15120
gcctaccagg  atagcttgaa  ggaaaatgag  gcgggacagg  aggataccgc  ccccgccgcc   15180
tccgccgccg  ccgagcaggg  cgaggatgct  gctgacaccg  cggccgcgga  cggggcagag   15240
gccgaccccg  ctatggtggt  ggaggctccc  gagcaggagg  aggacatgaa  tgacagtgcg   15300
gtgcgcggag  acaccttcgt  cacccggggg  gaggaaaagc  aagcggaggc  cgaggccgcg   15360
gccgaggaaa  agcaactggc  ggcagcagcg  cggcggcgg   cgttggccgc  ggcggaggct   15420
gagtctgagg  ggaccaagcc  cgccaaggag  cccgtgatta  agcccctgac  cgaagatagc   15480
aagaagcgca  gttacaacct  gctcaaggac  agcaccaaca  ccgcgtaccg  cagctggtac   15540
ctggcctaca  actacggcga  cccgtcgacg  ggggtgcgct  cctggaccct  gctgtgcacg   15600
ccggacgtga  cctgcggctc  ggagcaggtg  tactggtcgc  tgcccgacat  gatgcaagac   15660
cccgtgacct  tccgctccac  gcggcaggtc  agcaacttcc  cggtggtggg  cgccgagctg   15720
ctgcccgtgc  actccaagag  cttctacaac  gaccaggccg  tctactccca  gctcatccgc   15780
cagttcacct  ctctgaccca  cgtgttcaat  cgctttcctg  agaaccagat  tctggcgcgc   15840
ccgcccgccc  ccaccatcac  caccgtcagt  gaaaacgttc  ctgctctcac  agatcacggg   15900
acgctaccgc  tgcgcaacag  catcggagga  gtccagcgag  tgaccgttac  tgacgccaga   15960
cgccgcacct  gccctacgt   ttacaaggcc  ttgggcatag  tctcgccgcg  cgtcctttcc   16020
agccgcactt  tttgagcaac  accaccatca  tgtccatcct  gatctcaccc  agcaataact   16080
ccggctgggg  actgctgcgc  gcgcccagca  agatgttcgg  aggggcgagg  aagcgttccg   16140
agcagcaccc  cgtgcgcgtg  cgcgggcact  tccgcgcccc  ctgggagcg   cacaaacgcg   16200 gccgcgcggg  gcgcaccacc  gtggacgacg  ccatcgactc  ggtggtggag  caggcgcgca   16260
actacaggcc  cgcggtctct  accgtgacg   cggccatcca  gaccgtggtg  cggggcgcgc   16320
ggcggtacgc  caagctgaag  agccgccgga  agcgcgtggc  ccgccgccac  cgccgccgac   16380
ccggggccgc  cgccaaacgc  gccgccgcgg  ccctgcttcg  ccgggccaag  cgcacgggcc   16440
```

```
gccgcgccgc catgagggcc gcgcgccgct tggccgccgg catcaccgcc gccaccatgg    16500 cccccgtac ccgaagacgc gcggccgccg ccgccgccgc cgccatcagt gacatggcca     16560
gcaggcgccg gggcaacgtg tactgggtgc gcgactcggt gaccggcacg cgcgtgcccg    16620
tgcgcttccg ccccccgcgg acttgagatg atgtgaaaaa acaacactga gtctcctgct    16680
gttgtgtgta cccagcggc ggcggcgcgc gcagcgtcat gtccaagcgc aaaatcaaag     16740
aagagatgct ccaggtcgtc gcgccggaga tctatgggcc cccgaagaag gaagagcagg    16800
attcgaagcc ccgcaagata aagcgggtca aaagaaaaa gaaagatgat gacgatgccg     16860
atggggaggt ggagttcctg cgcgccacgg cgcccaggcg cccggtgcag tggaagggcc    16920
ggcgcgtaaa gcgcgtcctg cgccccggca ccgcggtggt cttcacgccc ggcgagcgct    16980
ccacccggac tttcaagcgc gtctatgacg aggtgtacgg cgacgaagac ctgctggagc    17040
aggccaacga gcgcttcgga gagtttgctt acgggaagcg tcagcgggcg ctggggaagg    17100
aggacctgct ggcgctgccg ctggaccagg gcaaccccac ccccagtctg aagcccgtga    17160
ccctgcagca ggtgctgccg agcagcgcac cctccgaggc gaagcggggt ctgaagcgcg    17220
agggcggcga cctggcgccc accgtgcagc tcatggtgcc caagcggcag aggctggagg    17280
atgtgctgga gaaaatgaaa gtagaccccg gtctgcagcc ggacatcagg gtccgcccca    17340
tcaagcaggt ggcgccgggc ctcggcgtgc agaccgtgga cgtggtcatc cccaccggca    17400
actcccccgc cgccgccacc actaccgctg cctccacgga catggagaca cagaccgatc    17460
ccgccgcagc cgcagccgca gccgccgccg cgacctcctc ggcggaggtg cagacggacc    17520
cctggctgcc gccggcgatg tcagctcccc gcgcgcgtcg cgggcgcagg aagtacggcg    17580
ccgccaacgc gctcctgccc gagtacgcct tgcatccttc catcgcgccc accccggct    17640 accgaggcta tacctaccgc ccgcgaagag ccaagggttc caccccgccgt ccccgccgac    17700 gcgccgccgc caccacccgc cgccgccgcc gcagacgcca gccgcactg gctccagtct    17760 ccgtgaggaa agtggcgcgc gacggacaca ccctggtgct gcccagggcg cgctaccacc    17820
ccagcatcgt ttaaaagcct gttgtggttc ttgcagatat ggccctcact tgccgcctcc    17880
gtttcccggt gccgggatac cgaggaggaa gatcgcgccg caggagggt ctggccggcc     17940 gcggcctgag cggaggcagc cgccgcgcgc accggcggcg acgcgccacc agccgacgca    18000
tgcgcggcgg ggtgctgccc ctgttaatcc ccctgatcgc cgcggcgatc ggcgccgtgc    18060
ccgggatcgc ctccgtggcc ttgcaagcgt cccagaggca ttgacagact tgcaaacttg    18120
caaatatgga aaaaaaacc ccaataaaaa agtctagact ctcacgctcg cttggtcctg     18180
tgactatttt gtagaatgga agacatcaac tttgcgtcgc tggccccgcg tcacggctcg    18240
cgcccgttcc tgggacactg gaacgatatc ggcaccagca acatgagcgg tggcgccttc    18300
agttggggct ctctgtggag cggcattaaa agtatcgggt ctgccgttaa aaattacggc    18360
tcccgggcct ggaacagcag cacgggccag atgttgagag acaagttgaa agagcagaac    18420
ttccagcaga aggtggtgga gggcctggcc tccggcatca acggggtggt ggacctggcc    18480
aaccaggccg tgcagaataa gatcaacagc agactggacc cccggccgcc ggtggaggag    18540
gtgccgccgg cgctggagac ggtgtccccc gatgggcgtg gcgagaagcg cccgcggccc    18600
gatagggaag agaccactct ggtcacgcag accgatgagc cgcccccgta tgaggaggcc    18660
ctgaagcaag gtctgcccac cacgcggccc atcgcgccca tggccaccgg ggtggtgggc    18720
cgccacaccc ccgccacgct ggacttgcct ccgcccgccg atgtgccgca gcagcagaag    18780
```

-continued

```
gcggcacagc cgggcccgcc cgcgaccgcc tcccgttcct ccgccggtcc tctgcgccgc    18840
gcggccagcg gccccccgcgg gggggtcgcg aggcacggca actggcagag cacgctgaac    18900
agcatcgtgg gtctgggggt gcggtccgtg aagcgccgcc gatgctactg aatagcttag    18960
ctaacgtgtt gtatgtgtgt atgcgcccta tgtcgccgcc agaggagctg ctgagtcgcc    19020
gccgttcgcg cgcccaccac caccgccact ccgcccctca agatggcgac cccatcgatg    19080
atgccgcagt ggtcgtacat gcacatctcg ggccaggacg cctcggagta cctgagcccc    19140
gggctggtgc agttcgcccg cgccaccgag agctacttca gcctgagtaa caagtttagg    19200
aaccccacgg tggcgcccac gcacgatgtg accaccgacc ggtctcagcg cctgacgctg    19260
cggttcattc ccgtggaccg cgaggacacc gcgtactcgt acaaggcgcg gttcaccctg    19320
gccgtgggcg acaaccgcgt gctggacatg gcctccacct actttgacat ccgcggggtg    19380
ctggaccggg gtcccacttt caagccctac tctggcaccg cctacaactc cctggccccc    19440
aagggcgctc ccaactcctg cgagtgggag caagaggaaa ctcaggcagt tgaagaagca    19500
gcagaagagg aagaagaaga tgctgacggt caagctgagg aagagcaagc agctaccaaa    19560
aagactcatg tatatgctca ggctccccctt tctggcgaaa aaattagtaa agatggtctg    19620
caaataggaa cggacgctac agctacagaa caaaaaccta tttatgcaga ccctacattc    19680
cagcccgaac cccaaatcgg ggagtcccag tggaatgagg cagatgctac agtcgccggc    19740
ggtagagtgc taaagaaatc tactcccatg aaaccatgct atggttccta tgcaagaccc    19800
acaaatgcta atggaggtca gggtgtacta acggcaaatg cccagggaca gctagaatct    19860
caggttgaaa tgcaattctt ttcaacttct gaaaacgccc gtaacgaggc taacaacatt    19920
cagcccaaat tggtgctgta tagtgaggat gtgcacatgg agaccccgga tacgcacctt    19980
tcttacaagc ccgcaaaaag cgatgacaat tcaaaaatca tgctgggtca gcagtccatg    20040
cccaacagac ctaattacat cggcttcaga gacaacttta tcggcctcat gtattacaat    20100
agcactggca acatgggagt gcttgcaggt caggcctctc agttgaatgc agtggtggac    20160
ttgcaagaca gaaacacaga actgtcctac cagctcttgc ttgattccat gggtgacaga    20220
accagatact tttccatgtg gaatcaggca gtggacagtt atgacccaga tgttagaatt    20280
attgaaaatc atggaactga agacgagctc cccaactatt gtttccctct gggtggcata    20340
ggggtaactg acacttacca ggctgttaaa accaacaatg gcaataacgg gggccaggtg    20400
acttggacaa aagatgaaac ttttgcagat cgcaatgaaa taggggtggg aaacaatttc    20460
gctatggaga tcaaccctcag tgccaacctg tggagaaact tcctgtactc caacgtggcg    20520
ctgtacctac cagacaagct taagtacaac ccctccaatg tggacatctc tgacaacccc    20580
aacacctacg attacatgaa caagcgagtg gtggccccgg ggctggtgga ctgctacatc    20640
aacctgggcg cgcgctggtc gctggactac atggacaacg tcaaccccctt caaccaccac    20700 cgcaatgcgg gcctgcgcta ccgctccatg ctcctgggca cgggcgcta cgtgcccttc    20760 cacatccagg tgcccagaa gttctttgcc atcaagaacc tcctcctcct gccgggctcc    20820
tacacctacg agtggaactt caggaaggat gtcaacatgg tcctccagag ctctctgggt    20880
aacgatctca gggtggacgg ggccagcatc aagttcgaga gcatctgcct ctacgccacc    20940
ttcttcccca tggcccacaa cacggcctcc acgctcgagg ccatgctcag gaacgacacc    21000
aacgaccagt ccttcaatga ctacctctcc gccgccaaca tgctctaccc catacccgcc    21060
aacgccacca acgtccccat ctccatcccc tcgcgcaact gggcggcctt ccgcggctgg    21120
gccttcaccc gcctcaagac caaggagacc ccctcccctgg gctcgggatt cgacccctac    21180
```

```
tacacctact cgggctccat tccctacctg gacggcacct tctacctcaa ccacactttc   21240
aagaaggtct cggtcacctt cgactcctcg gtcagctggc cgggcaacga ccgtctgctc   21300 accccccaacg agttcgagat caagcgctcg gtcgacgggg agggctacaa cgtggcccag   21360
tgcaacatga ccaaggactg gttcctggtc cagatgctgg ccaactacaa catcggctac   21420
cagggcttct acatcccaga gagctacaag gacaggatgt actccttctt caggaacttc   21480
cagcccatga gccggcaggt ggtggaccag accaagtaca aggactacca ggaggtgggc   21540
atcatccacc agcacaacaa ctcgggcttc gtgggctacc tcgcccccac catgcgcgag   21600
ggacaggcct accccgccaa cttcccctat ccgctcatag gcaagaccgc ggtcgacagc   21660
atcacccaga aaaagttcct ctgcgaccgc accctctggc gcatccccett ctccagcaac   21720 ttcatgtcca tgggtgcgct ctcggacctg ggccagaact tgctctacgc caactccgcc   21780
cacgccctcg acatgaccett cgaggtcgac cccatggacg agcccaccct tctctatgtt   21840
ctgttcgaag tctttgacgt ggtccgggtc caccagccgc accgcggcgt catcgagacc   21900
gtgtacctgc gtacgcccett ctcggccggc aacgccacca cctaaagaag caagccgcag   21960
tcatcgccgc ctgcatgccg tcgggttcca ccgagcaaga gctcagggcc atcgtcagag   22020
acctgggatg cgggccctat tttttgggca ccttcgacaa gcgcttccct ggctttgtct   22080
ccccacacaa gctggcctgc gccatcgtca acacggccgg ccgcgagacc ggggcgtgc   22140 actggctggc cttcgcctgg aacccgcgct ccaaaacatg cttcctcttt gaccccttcg   22200
gcttttcgga ccagcggctc aagcaaatct acgagttcga gtacgagggc ttgctgcgtc   22260
gcagcgccat cgcctcctcg cccgaccgct gcgtcaccct cgaaaagtcc acccagaccg   22320
tgcaggggcc cgactcggcc gcctgcggtc tcttctgctg catgtttctg cacgcctttg   22380
tgcactggcc tcagagtccc atggaccgca accccaccat gaacttgctg acggggggtgc   22440 ccaactccat gctccagagc ccccaggtcg agcccaccct gcgccgcaac caggagcagc   22500
tctacagctt cctggagcgc cactcgcctt acttccgccg ccacagcgca cagatcagga   22560
gggccacctc cttctgccac ttgcaagaga tgcaagaagg gtaataacga tgtacacact   22620
ttttttctca ataaatggca tcttttttatt tatacaagct ctctgggggta ttcattccc   22680 accaccaccc gccgttgtcg ccatctggct ctatttagaa atcgaaaggg ttctgccggg   22740
agtcgccgtg cgccacgggc agggacacgt tgcgatactg gtagcgggtg ccccacttga   22800
actcgggcac caccaggcga ggcagctcgg ggaagttttc gctccacagg ctgcgggtca   22860
gcaccagcgc gttcatcagg tcgggcgccg agatcttgaa gtcgcagttg ggccgccgc   22920 cctgcgcgcg cgagttgcgg tacaccgggt tgcagcactg gaacaccaac agcgccgggt   22980
gcttcacgct ggccagcacg ctgcggtcgg agatcagctc ggcgtccagg tcctccgcgt   23040
tgctcagcgc gaacggggtc atcttgggca cttgccgccc caggaagggc gcgtgccccg   23100
gtttcgagtt gcagtcgcag cgcagcggga tcagcaggtg cccgtgcccg gactcggcgt   23160
tggggtacag cgcgcgcatg aaggcctgca tctggcggaa ggccatctgg gccttggcgc   23220
cctccgagaa gaacatgccg caggacttgc ccgagaactg gtttgcgggg cagctggcgt   23280
cgtgcaggca gcagcgcgcg tcggtgttgg cgatctgcac cacgttgcgc ccccaccggt   23340
tcttcacgat cttggccttg gacgattgct ccttcagcgc gcgctgcccg ttctcgctgg   23400
tcacatccat ctcgatcaca tgttcccttgt tcaccatgct gctgccgtgc agacacttca   23460
gctcgccctc cgtctcggtg cagcggtgct gccacagcgc gcagcccgtg ggctcgaaag   23520
```

```
acttgtaggt cacctccgcg aaggactgca ggtacccctg caaaaagcgg cccatcatgg    23580
tcacgaaggt cttgttgctg ctgaaggtca gctgcagccc gcggtgctcc tcgttcagcc    23640
aggtcttgca cacggccgcc agcgcctcca cctggtcggg cagcatcttg aagttcacct    23700
tcagctcatt ctccacgtgg tacttgtcca tcagcgtgcg cgccgcctcc atgcccttct    23760
cccaggccga caccagcggc aggctcacgg ggttcttcac catcaccgtg gccgccgcct    23820
ccgccgcgct ttcgctttcc gccccgctgt tctcttcctc ttcctcctct tcctcgccgc    23880
cgcccactcg cagcccccgc accacggggt cgtcttcctg caggcgctgc accttgcgct    23940
tgccgttgcg cccctgcttg atgcgcacgg gcggggttgct gaagcccacc atcaccagcg    24000
cggcctcttc ttgctcgtcc tcgctgtcca gaatgacctc cggggagggg gggttggtca    24060
tcctcagtac cgaggcacgc ttcttttttct tcctgggggc gttcgccagc tccgcggctg    24120
cggccgctgc cgaggtcgaa ggccgagggc tgggcgtgcg cggcaccagc gcgtcctgcg    24180
agccgtcctc gtcctcctcg gactcgagac ggaggcgggc ccgcttcttc ggggcgcgc     24240 ggggcggcgg aggcggcggc ggcgacgag acggggacga gacatcgtcc agggtgggtg     24300
gacggcgggc cgcgccgcgt ccgcgctcgg gggtggtctc gcgctggtcc tcttcccgac    24360
tggccatctc ccactgctcc ttctcctata ggcagaaaga gatcatggag tctctcatgc    24420
gagtcgagaa ggaggaggac agcctaaccg ccccctctga gccctccacc accgccgcca    24480
ccaccgccaa tgccgccgcg gacgacgcgc ccaccgagac caccgccagt accaccctcc    24540
ccagcgacgc acccccgctc gagaatgaag tgctgatcga gcaggacccg ggttttgtga    24600
gcggagagga ggatgaggtg gatgagaagg agaaggagga ggtcgccgcc tcagtgccaa    24660
aagaggataa aaagcaagac caggacgacg cagataagga tgagacagca gtcgggcggg    24720
ggaacggaag ccatgatgct gatgacggct acctagacgt gggagacgac gtgctgctta    24780
agcacctgca ccgccagtgc gtcatcgtct gcgacgcgct gcaggagcgc tgcgaagtgc    24840
ccctggacgt ggcggaggtc agccgcgcct acgagcggca cctcttcgcg ccgcacgtgc    24900
cccccaagcg ccgggagaac ggcacctgcg agcccaaccc gcgtctcaac ttctacccgg    24960
tcttcgcggt acccgaggtg ctggccacct accacatctt tttccaaaac tgcaagatcc    25020
ccctctcctg ccgcgccaac cgcacccgcg ccgacaaaac cctgaccctg cggcagggcg    25080
cccacatacc tgatatcgcc tctctggagg aagtgcccaa gatcttcgag ggtctcggtc    25140
gcgacgagaa acgggcggcg aacgctctgc acggagacag cgaaaacgag agtcactcgg    25200
gggtgctggt ggagctcgag ggcgacaacg cgcgcctggc cgtactcaag cgcagcatag    25260
aggtcaccca ctttgcctac ccggcgctca acctgccccc caaggtcatg agtgtggtca    25320
tgggcgagct catcatgcgc cgcgcccagc ccctggccgc ggatgcaaac ttgcaagagt    25380
cctccgagga aggcctgccc gcggtcagcg acagcagct ggcgcgctgg ctggagaccc      25440
gcgaccccgc gcagctggag gagcggcgca agctcatgat ggccgcggtg ctggtcaccg    25500
tggagctcga gtgtctgcag cgcttcttcg cggaccccga gatgcagcgc aagctcgagg    25560
agaccctgca ctacaccttc cgccagggct acgtgcgcca ggcctgcaag atctccaacg    25620
tggagctctg caacctggtc tcctacctgg gcatcctgca cgagaaccgc ctcgggcaga    25680
acgtcctgca ctccacccatc aaaggggagg cgcgccgcga ctacatccgc gactgcgcct   25740
acctcttcct ctgctacacc tggcagacgg ccatggggt ctggcagcag tgcctggagg    25800
agcgcaacct caaggagctg aaaagctcc tcaagcgcac cctcagggac ctctggacgg    25860
gcttcaacga gcgctcggtg gccgccgcgc tggcggacat catctttccc gagcgcctgc    25920
```

```
tcaagaccct gcagcagggc ctgcccgact tcaccagcca gagcatgctg cagaacttca  25980
ggactttcat cctggagcgc tcgggcatcc tgccggccac ttgctgcgcg ctgcccagcg  26040
acttcgtgcc catcaagtac agggagtgcc cgccgccgct ctggggccac tgctacctct  26100
tccagctggc caactacctc gcctaccact cggacctcat ggaagacgtg agcggcgagg  26160
gcctgctcga gtgccactgc cgctgcaacc tctgcacgcc ccaccgctct ctagtctgca  26220
acccgcagct gctcagcgag agtcagatta tcggtacctt cgagctgcag ggtccctcgc  26280
ctgacgagaa gtccgcgggct ccagggctga aactcactcc ggggctgtgg acttccgcct  26340
acctacgcaa atttgtacct gaggactacc acgcccacga gatcaggttc tacgaagacc  26400
aatcccgccc gcccaaggcg gagctcaccg cctgcgtcat cacccagggg cacatcctgg  26460
gccaattgca agccatcaac aaagcccgcc gagagttctt gctgaaaaag ggtcgggggg  26520
tgtacctgga cccccagtcc ggcgaggagc taaacccgct accccgcccg ccgccccagc  26580
agcgggacct tgcttcccag gatggcaccc agaaagaagc agcagccgcc gccgccgccg  26640
cagccataca tgcttctgga ggaagaggag gaggactggg acagtcaggc agaggaggtt  26700
tcggacgagg agcaggagga gatgatggaa gactgggagg aggacagcag cctagacgag  26760
gaagcttcag aggccgaaga ggtggcagac gcaacaccat cgccctcggt cgcagccccc  26820
tcgccggggc ccctgaaatc ctccgaaccc agcaccagcg ctataacctc cgctcctccg  26880
gcgccggcgc cacccgcccg cagacccaac cgtagatggg acaccacagg aaccggggtc  26940
ggtaagtcca agtgcccgcc gccgccaccg cagcagcagc agcagcagcg ccagggctac  27000
cgctcgtggc gcgggcacaa gaacgccata gtcgcctgct gcaagactg cgggggcaac  27060 atctctttcg cccgccgctt cctgctattc caccacgggg tcgcctttcc ccgcaatgtc  27120
ctgcattact accgtcatct ctacagcccc tactgcagcg gcgacccaga ggcggcagcg  27180
gcagccacag cggcgaccac cacctaggaa gatatcctcc gcgggcaaga cagcggcagc  27240
agcggccagg agacccgcgg cagcagcggc gggagcggtg ggcgcactgc gcctctcgcc  27300
caacgaaccc ctctcgaccc gggagctcag acacaggatc ttccccactt tgtatgccat  27360
cttccaacag agcagaggcc aggagcagga gctgaaaata aaaaacagat ctctgcgctc  27420
cctcacccgc agctgtctgt atcacaaaag cgaagatcag cttcggcgca cgctggagga  27480
cgcggaggca ctcttcagca atactgcgc gctcactctt aaagactagc tccgcgccct  27540
tctcgaattt aggcgggaga aaactacgtc atcgccggcc gccgcccagc ccgcccagcc  27600
gagatgagca aagagattcc cacgccatac atgtggagct accagccgca gatgggactc  27660
gcggcgggag cggcccagga ctactccacc cgcatgaact acatgagcgc gggaccccac  27720
atgatctcac aggtcaacgg gatccgcgcc cagcgaaacc aaatactgct ggaacaggcg  27780
gccatcaccg ccacgccccg ccataatctc aaccccgaa attggcccgc cgccctcgtg  27840
taccaggaaa ccccctccgc caccaccgta ctacttccgc gtgacgccca ggccgaagtc  27900
cagatgacta actcaggggc gcagctcgcg ggcggctttc gtcacggggc gcggccgctc  27960
cgaccaggta taagacacct gatgatcaga ggccgaggta tccagctcaa cgacgagtcg  28020
gtgagctctt cgctcggtct ccgtccggac ggaactttcc agctcgccgg atccggccgc  28080
tcttcgttca cgcccgcca ggcgtacctg actctgcaga cctcgtcctc ggagccccgc  28140
tccggcggca tcgaacccct ccagttcgtg gaggagttcg tgcctcggt ctacttcaac  28200 cccttctcgg gacctcccgg acgctacccc gaccagttca ttccgaactt tgacgcggtg  28260
```

```
aaggactcgg cggacggcta cgactgaatg tcaggtgtcg aggcagagca gcttcgcctg    28320
agacacctcg agcactgccg ccgccacaag tgcttcgccc gcggttctgg tgagttctgc    28380
tactttcagc tacccgagga gcataccgag gggccggcgc acggcgtccg cctgaccacc    28440
cagggcgagg ttacctgttc cctcatccgg gagtttaccc tccgtcccct gctagtggag    28500
cgggagcggg gtccctgtgt cctaactatc gcctgcaact gccctaaccc tggattacat    28560
caagatcttt gctgtcatct ctgtgctgag tttaataaac gctgagatca gaatctactg    28620
gggctcctgt cgccatcctg tgaacgccac cgtcttcacc caccccgacc aggcccaggc    28680
gaacctcacc tgcggtctgc atcggagggc aagaagtac ctcacctggt acttcaacgg    28740
cacccccttt gtggtttaca acagcttcga cggggacgga gtctccctga agaccagct    28800 ctccggtctc agctactcca tccacaagaa caccaccctc caactcttcc ctccctacct    28860
gccgggaacc tacgagtgcg tcaccggccg ctgcacccac ctcacccgcc tgatcgtaaa    28920
ccagagcttt ccgggaacag ataactccct cttcccaga acaggagtg agctcaggaa    28980 actccccggg gaccagggcg gagacgtacc ttcgacccctt gtggggttag gattttttat    29040
taccgggttg ctggctcttt taatcaaagt ttccttgaga tttgttcttt ccttctacgt    29100
gtatgaacac ctcaacctcc aataactcta cccttcttc ggaatcaggt gacttctctg    29160
aaatcgggct tggtgtgctg cttactctgt tgattttttt ccttatcata ctcagccttc    29220
tgtgcctcag gctcgccgcc tgctgcgcac acatctatat ctactgctgg ttgctcaagt    29280
gcaggggtcg ccacccaaga tgaacaggta catggtccta tcgatcctag gcctgctggc    29340
cctggcggcc tgcagcgccg ccaaaaaaga gattaccttt gaggagcccg cttgcaatgt    29400
aactttcaag cccgaggggt gaccaatgcac caccctcgtc aaatgcgtta ccaatcatga    29460
gaggctgcgc atcgactaca aaaacaaaac tggccagttt gcggtctata gtgtgtttac    29520 gccccggagac ccctctaact actctgtcac cgtcttccag ggcggacagt ctaagatatt    29580
caattacact ttccctttt atgagttatg cgatgcggtc atgtacatgt caaaacagta    29640
caacctgtgg cctccctctc cccaggcgtg tgtggaaaat actgggtctt actgctgtat    29700
ggctttcgca atcactacgc tcgctctaat ctgcacggtg ctatacataa aattcaggca    29760
gaggcgaatc tttatcgatg aaaagaaaat gccttgatcg ctaacaccgg cttttctatct    29820 gcagaatgaa tgcaatcacc tccctactaa tcaccaccac cctccttgcg attgcccatg    29880
ggttgacacg aatcgaagtg ccagtggggt ccaatgtcac catggtgggc cccgccggca    29940
attccaccct catgtgggaa aaatttgtcc gcaatcaatg ggttcatttc tgctctaacc    30000
gaatcagtat caagcccaga gccatctgcg atgggcaaaa tctaactctg atcaatgtgc    30060
aaatgatgga tgctgggtac tattacgggc agcggggaga atcattaat tactggcgac    30120 cccacaagga ctacatgctg catgtagtcg aggcacttcc cactaccacc cccactacca    30180
cctctcccac caccaccacc actactacta ctactactac tactactact actaccacta    30240
ccgctgcccg ccatacccgc aaaagcacca tgattagcac aaagcccct cgtgctcact    30300 cccacgccgg cgggcccatc ggtgcgacct cagaaccac cgagctttgc ttctgccaat    30360
gcactaacgc cagcgctcat gaactgttcg acctggagaa tgaggatgtc cagcagagct    30420
ccgcttgcct gacccaggag gctgtggagc ccgttgccct gaagcagatc ggtgattcaa    30480
taattgactc ttcttctttt gccactcccg aataccctcc cgattctact ttccacatca    30540
cgggtaccaa agaccctaac ctctcttct acctgatgct gctgctctgt atctctgtgg    30600
tctcttccgc gctgatgtta ctggggatgt tctgctgcct gatctgccgc agaaagagaa    30660
```

```
aagctcgctc tcagggccaa ccactgatgc ccttcccta cccccggat tttgcagata   30720
acaagatatg agctcgctgc tgacactaac cgctttacta gcctgcgctc taaccctgt   30780
cgcttgcgac tcgagattcc acaatgtcac agctgtggca ggagaaaatg ttactttcaa   30840
ctccacggcc gatacccagt ggtcgtggag tggctcaggt agctacttaa ctatctgcaa   30900
tagctccact tcccccggca tatcccaac caagtaccaa tgcaatgcca gcctgttcac   30960
cctcatcaac gcttccaccc tggacaatgg actctatgta ggctatgtac cctttggtgg   31020
gcaaggaaag acccacgctt acaacctgga agttcgccag cccagaacca ctacccaagc   31080
ttctcccacc accaccacca ccaccaccat caccagcagc agcagcagca gcagccacag   31140
cagcagcagc agattattga ctttggtttt ggccagctca tctgccgcta cccaggccat   31200
ctacagctct gtgcccgaaa ccactcagat ccaccgccca gaaacgacca ccgccaccac   31260
cctacacacc tccagcgatc agatgccgac caacatcacc cccttggctc ttcaaatggg   31320
acttacaagc cccactccaa aaccagtgga tgcggccgag gtctccgccc tcgtcaatga   31380
ctgggcgggg ctgggaatgt ggtggttcgc cataggcatg atggcgctct gcctgcttct   31440
gctctggctc atctgctgcc tccaccgcag gcgagccaga cccccatct atagacccat   31500
cattgtcctg aaccccgata atgatgggat ccatagattg gatggcctga aaaacctact   31560
ttttcttt acagtatgat aaattgagac atgcctcgca ttttcttgta catgttcctt   31620
ctcccacctt ttctggggtg ttctacgctg ccgctgtgt ctcacctgga ggtagactgc   31680
ctctcaccct tcactgtcta cctgctttac ggattggtca ccctcactct catctgcagc   31740
ctaatcacag taatcatcgc cttcatccag tgcattgatt acatctgtgt gcgcctcgca   31800
tacttcagac accaccgca gtaccgagac aggaacattg cccaacttct aagactgctc   31860
taatcatgca taagactgtg atctgccttc tgatcctctg catcctgccc accctcacct   31920
cctgccagta caccacaaaa tctccgcgca aaagacatgc ctcctgccgc ttcacccaac   31980
tgtggaatat acccaaatgc tacaacgaaa agagcgagct ctccgaagct tggctgtatg   32040
gggtcatctg tgtcttagtt ttctgcagca ctgtctttgc cctcataatc taccctact   32100
ttgatttggg atggaacgcg atcgatgcca tgaattaccc cacctttccc gcacccgaga   32160
taattccact gcgacaagtt gtacccgttg tcgttaatca acgcccccca tcccctacgc   32220
ccactgaaat cagctacttt aacctaacag gcggagatga ctgacgccct agatctaaa   32280
atggacggca tcagtaccga gcagcgtctc ctagagaggc gcaggcaggc ggctgagcaa   32340
gagcgcctca atcaggagct ccgagatctc gttaacctgc accagtgcaa aagaggcatc   32400
ttttgtctgg taaagcaggc caaagtcacc tacgagaaga ccggcaacag ccaccgcctc   32460
agttacaaat tgcccaccca gcgccagaag ctggtgctca tggtgggtga aatccatc   32520
accgtcaccc agcactcggt agagaccgag gggtgtctgc actcccctg tcggggtcca   32580
gaagacctct gcaccctggt aaagaccctg tgcggtctca gagatttagt cccctttaac   32640
taatcaaaca ctggaatcaa taaaaagaat cacttactta aaatcagaca gcaggtctct   32700
gtccagttta ttcagcagca cctccttccc ctcctcccaa ctctggtact ccaaacgcct   32760
tctggcggca aacttcctcc acaccctgaa gggaatgtca gattcttgct cctgtccctc   32820
cgcacccact atcttcatgt tgttgcagat gaagcgcacc aaaacgtctg acgagagctt   32880
caaccccgtg taccctatg acacggaaag cggcctcc tcgtccctt tcctcacccc   32940
tcccttcgtg tctcccgatg gattccaaga aagtccccc ggggtcctgt ctctgaacct   33000
```

```
ggccgagccc ctggtcactt cccacggcat gctcgccctg aaaatgggaa gtggcctctc    33060
cctggacgac gctggcaacc tcacctctca agatatcacc accgctagcc ctcccctcaa    33120
aaaaaccaag accaacctca gcctagaaac ctcatccccc ctaactgtga gcacctcagg    33180
cgccctcacc gtagcagccg ccgctcccct ggcggtggcc ggcacctccc tcaccatgca    33240
atcagaggcc cccctgacag tacaggatgc aaaactcacc ctggccacca aaggcccct    33300 gaccgtgtct gaaggcaaac tggccttgca acatcggcc ccgctgacgg ccgctgacag    33360
cagcaccctc acagtcagtg ccacaccacc ccttagcaca agcaatggca gcttgggtat    33420
tgacatgcaa gcccccattt acaccaccaa tggaaaacta ggacttaact ttggcgctcc    33480
cctgcatgtg gtagacagcc taaatgcact gactgtagtt actggccaag gtcttacgat    33540
aaacggaaca gccctacaaa ctagagtctc aggtgccctc aactatgaca catcaggaaa    33600
cctagaattg agagctgcag ggggtatgcg agttgatgca aatggtcaac ttatccttga    33660
tgtagcttac ccatttgatg cacaaaacaa tctcagcctt aggcttggac agggaccct    33720 gtttgttaac tctgcccaca acttggatgt taactacaac agaggcctct acctgttcac    33780
atctggaaat accaaaaagc tagaagttaa tatcaaaaca gccaagggtc tcatttatga    33840
tgacactgct atagcaatca atgcgggtga tgggctacag tttgactcag gctcagatac    33900
aaatccatta aaaactaaac ttggattagg actggattat gactccagca gagccataat    33960
tgctaaactg ggaactggcc taagctttga caacacaggt gccatcacag taggcaacaa    34020
aaatgatgac aagcttacct tgtggaccac accagaccca tcccctaact gtagaatcta    34080
ttcagagaaa gatgctaaat tcacacttgt tttgactaaa tgcggcagtc aggtgttggc    34140
cagcgttcct gttttatctg taaaaggtag ccttgcgccc atcagtggca cagtaactag    34200
tgctcagatt gtcctcagat ttgatgaaaa tggagttcta ctaagcaatt cttcccttga    34260
ccctcaatac tggaactaca gaaaaggtga ccttacagag ggcactgcat ataccaacgc    34320
agtgggattt atgcccaacc tcacagcata cccaaaaaca cagagccaaa ctgctaaaag    34380
caacattgta agtcaggttt acttgaatgg ggacaaatcc aaacccatga ccctcaccat    34440
taccctcaat ggaactaatg aaacaggaga tgccacagta agcacttact ccatgtcatt    34500
ctcatggaac tggaatggaa gtaattacat taatgaaacg ttccaaacca actccttcac    34560
cttctcctac atcgcccaag aataaaaagc atgacgctgt tgatttgatt caatgtgttt    34620
ctgttttatt ttcaagcaca acaaaatcat tcaagtcatt cttccatctt agcttaatag    34680
acacagtagc ttaatagacc cagtagtgca aagcccatt ctagcttata gatcagacag    34740
tgataattaa ccaccaccac caccatacct tttgattcag gaaatcatga tcatcacagg    34800
atcctagtct tcaggccgcc ccctccctcc caagacacag aatacacagt cctctccccc    34860
cgactggctt taaataacac catctggttg gtcacagaca tgttcttagg ggttatattc    34920
cacacggtct cctgccgcgc caggcgctcg tcggtgatgt tgataaactc tcccggcagc    34980
tcgctcaagt tcacgtcgct gtccagcggc tgaacctccg gctgacgcga taactgtgcg    35040
accggctgct ggacgaacgg aggccgcgcc tacaaggggg tagagtcata atcctcggtc    35100
aggatagggc ggtgatgcag cagcagcgag cgaaacatct gctgccgccg ccgctccgtc    35160
cggcaggaaa acaacacgcc ggtggtctcc tccgcgataa tccgcaccgc ccgcagcatc    35220
agcttcctcg ttctccgcgc gcagcacctc accttatctc gctcaaatc ggcgcagtag    35280 gtacagcaca gcaccacgat gttattcatg atcccacagt gcagggcgct gtatccaaag    35340
ctcatgccgg gaaccaccgc ccccacgtgg ccatcgtacc acaagcgcac gtaaatcaag    35400
```

```
tgtcgacccc tcatgaacgc gctggacaca acattactt ccttgggcat gttgtaattc    35460
accacctccc ggtaccagat aaacctctgg ttgaacaggg caccttccac caccatcctg    35520
aaccaagagg ccagaacctg cccaccggct atgcactgca gggaacccgg gttggaacaa    35580
tgacaatgca gactccaagg ctcgtaaccg tggatcatcc ggctgctgaa ggcatcgatg    35640
ttggcacaac acagacacac gtgcatgcac tttctcatga ttagcagctc ttccctcgtc    35700
aggatcatat cccaaggaat aacccattct tgaatcaacg taaaacccac acagcaggga    35760
aggcctcgca cataactcac gttgtgcatg gtcagcgtgt tgcattccgg aaacagcgga    35820
tgatcctcca gtatcgaggc gcgggtctcc ttctcacagg gaggtaaagg gtccctgctg    35880
tacggactgc gccgggacga ccgagatcgt gttgagcgta gtgtcatgga aagggaacg     35940
ccggacgtgg tcatacttct tgaagcagaa ccaggttcgc gcgtggcagg cctccttgcg    36000
tctgcggtct cgccgtctag ctcgctccgt gtgatagttg tagtacagcc actcccgcag    36060
agcgtcgagg cgcaccctgg cttccggatc tatgtagact ccgtcttgca ccgcggccct    36120
gataatatcc accaccgtag aataagcaac acccagccaa gcaatacact cgctctgcga    36180
gcggcagaca ggaggagcgg gcagagatgg gagaaccatg ataaaaaact ttttttaaag    36240
aatattttcc aattcttcga agtaagatc tatcaagtgg cagcgctccc ctccactggc     36300
gcggtcaaac tctacggcca aagcacagac aacggcattt ctaagatgtt ccttaatggc    36360
gtccaaaaga cacaccgctc tcaagttgca gtaaactatg aatgaaaacc catccggctg    36420
attttccaat atagacgcgc cggcagcgtc caccaaaccc agataatttt cttctctcca    36480
gcggtttacg atctgtctaa gcaaatccct tatatcaagt ccgaccatgc caaaaatctg    36540
ctcaagagcg ccctccacct tcatgtacaa gcagcgcatc atgattgcaa aaattcaggt    36600
tcttcagaga cctgtataag attcaaaatg gaacattaa caaaaattcc tctgtcgcgc     36660
agatcccttc gcagggcaag ctgaacataa tcagacaggt ccgaacggac cagtgaggcc    36720
aaatccccac caggaaccag atccagagac cctatactga ttatgacgcg catactcggg    36780
gctatgctga ccagcgtagc gccgatgtag gcgtgctgca tgggcggcga gataaaatgc    36840
aaagtgctgg ttaaaaaatc aggcaaagcc tcgcgcaaaa aagctaacac atcataatca    36900
tgctcatgca ggtagttgca ggtaagctca ggaaccaaaa cggaataaca cacgattttc    36960
ctctcaaaca tgacttcgcg gatactgcgt aaaacaaaaa attataaata aaaaattaat    37020
taaataactt aaacattgga agcctgtctc acaacaggaa aaaccacttt aatcaacata    37080
agacgggcca cgggcatgcc ggcatagccg taaaaaaatt ggtccccgtg attaacaagt    37140
accacagaca gctccccggt catgtcgggg gtcatcatgt gagactctgt atacacgtct    37200
ggattgtgaa catcagacaa acaaagaaat cgagccacgt agcccggagg tataatcacc    37260
cgcaggcgga ggtacagcaa aacgaccccc ataggaggaa tcacaaaatt agtaggagaa    37320
aaaaatacat aaacaccaga aaaacccctgt tgctgaggca aaatagcgcc ctcccgatcc    37380
aaaacaacat aaagcgcttc cacaggagca gccataacaa agacccgagt cttaccagta    37440
aaagaaaaaa gatctctcaa cgcagcacca gcaccaacac ttcgcagtgt aaaaggccaa    37500
gtgccgagag agtatatata ggaataaaaa gtgacgtaaa cgggcaaagt ccaaaaaacg    37560
cccagaaaaa ccgcacgcga acctacgccc cgaaacgaaa gccaaaaaac actagacact    37620
cccttccggc gtcaacttcc gctttcccac gctacgtcac ttccccggt caaacaaact    37680
acatatcccg aacttccaag tcgccacgcc caaaacaccg cctacacctc cccgcccgcc    37740
```

```
ggcccgcccc cggacccgcc tcccgccccg cgccgcccat ctcattatca tattggcttc    37800
aatccaaaat aagtatatt attgatgatg                                      37830
```

<210> SEQ ID NO 2
<211> LENGTH: 1109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2

```
ggagttccgc gttacataac ttacggtaaa tggcccgcct ggctgaccgc ccaacgaccc      60
ccgcccattg acgtcaataa tgacgtatgt tcccatagta acgccaatag ggactttcca     120
ttgacgtcaa tgggtggagt atttacggta aactgcccac ttggcagtac atcaagtgta     180
tcatatgcca agtacgcccc ctattgacgt caatgacggt aaatggcccg cctggcatta     240
tgcccagtac atgaccttat gggactttcc tacttggcag tacatctacg tattagtcat     300
cgctattacc atggtcgagg tgagcccac gttctgcttc actctcccca tctcccccc      360 ctccccaccc ccaattttgt atttatttat ttttaatta ttttgtgcag cgatggggc      420 gggggggggg ggggcgcgc gccaggcggg gcggggcggg gcgaggggcg gggcggggcg     480
aggcggagag gtgcggcggc agccaatcag agcggcgcgc tccgaaagtt tccttttatg     540
gcgaggcggc ggcggcggcg gccctataaa aagcgaagcg ctccctatca gtgatagaga     600
tctccctatc agtgatagag atcgtcgacg agctcgcggc gggcgggagt cgctgcgcgc     660
tgccttcgcc ccgtgccccg ctccgccgcc gcctcgcgcc gcccgccccg gctctgactg     720
accgcgttac taaacaggt aagtccggcc tccgcgccgg gttttggcgc ctcccgcggg     780
cgcccccctc ctcacggcga gcgctgccac gtcagacgaa gggcgcagcg agcgtcctga     840
tccttccgcc cggacgctca ggacagcggc ccgctgctca taagactcgg ccttagaacc     900
ccagtatcag cagaaggaca ttttaggacg ggacttgggt gactctaggg cactggtttt     960 cttttccagag agcggaacag gcgaggaaaa gtagtccctt ctcggcgatt ctgcggaggg    1020
atctccgtgg ggcggtgaac gccgatgatg cctctactaa ccatgttcat gttttctttt    1080
tttttctaca ggtcctgggt gacgaacag                                     1109
```

<210> SEQ ID NO 3
<211> LENGTH: 1187
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3

```
ccattgcata cgttgtatcc atatcataat atgtacattt atattggctc atgtccaaca      60
ttaccgccat gttgacattg attattgact agttattaat agtaatcaat tacggggtca     120
ttagttcata gcccatatat ggagttccgc gttacataac ttacggtaaa tggcccgcct     180
ggctgaccgc ccaacgaccc ccgcccattg acgtcaataa tgacgtatgt tcccatagta     240
acgccaatag ggactttcca ttgacgtcaa tgggtggagt atttacggta aactgcccac     300
ttggcagtac atcaagtgta tcatatgcca agtacgcccc ctattgacgt caatgacggt     360
aaatggcccg cctggcatta tgcccagtac atgaccttat gggactttcc tacttggcag     420
```

```
tacatctacg tattagtcat cgctattacc atggtgatgc ggttttggca gtacatcaat      480
gggcgtggat agcggtttga ctcacgggga tttccaagtc tccacccat tgacgtcaat       540 gggagtttgt tttggcacca aaatcaacgg gactttccaa aatgtcgtaa caactccgcc      600
ccattgacgc aaatgggcgg taggcgtgta cggtgggagg tctatataag cgaagcgct      660 ccctatcagt gatagagatc tccctatcag tgatagagat cgtcgacgag ctcgcggcgg      720
gcgggagtcg ctgcgcgctg ccttcgcccc gtgccccgct ccgccgccgc ctcgcgccgc      780
ccgccccggc tctgactgac cgcgttacta aaacaggtaa gtccggcctc cgcgccgggt      840
tttggcgcct cccgcgggcg ccccctcct cacggcgagc gctgccacgt cagacgaagg       900
gcgcagcgag cgtcctgatc cttccgcccg gacgctcagg acagcggccc gctgctcata      960
agactcggcc ttagaacccc agtatcagca gaaggacatt taggacggg acttgggtga      1020 ctctagggca ctggtttct tccagagag cggaacaggc gaggaaaagt agtcccttct       1080
cggcgattct gcggagggat ctccgtgggg cggtgaacgc cgatgatgcc tctactaacc     1140
atgttcatgt tttcttttt tttctacagg tcctgggtga cgaacag                    1187
```

<210> SEQ ID NO 4
<211> LENGTH: 2908
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4

```
ccattgcata cgttgtatcc atatcataat atgtacattt atattggctc atgtccaaca       60
ttaccgccat gttgacattg attattgact agttattaat agtaatcaat tacggggtca      120
ttagttcata gcccatatat ggagttccgc gttacataac ttacggtaaa tggcccgcct      180
ggctgaccgc ccaacgaccc ccgcccattg acgtcaataa tgacgtatgt tcccatagta      240
acgccaatag ggactttcca ttgacgtcaa tgggtggagt atttacgta aactgcccac       300 ttggcagtac atcaagtgta tcatatgcca agtacgcccc ctattgacgt caatgacggt      360
aaatggcccg cctggcatta tgcccagtac atgaccttat gggactttcc tacttggcag      420
tacatctacg tattagtcat cgctattacc atggtgatgc ggttttggca gtacatcaat      480
gggcgtggat agcggtttga ctcacgggga tttccaagtc tccacccat tgacgtcaat       540 gggagtttgt tttggcacca aaatcaacgg gactttccaa aatgtcgtaa caactccgcc      600
ccattgacgc aaatgggcgg taggcgtgta cggtgggagg tctatataag cagagctctc      660
cctatcagtg atagagatct ccctatcagt gatagagatc gtcgacgagc tcgtttagtg      720
aaccgtcaga tcgcctggag acgccatcca cgctgttttg acctccatag aagacaccgg      780
gaccgatcca gcctccgcgg ccgggaacg tgcattggaa cgcggattcc ccgtgccaag       840
agtgagatct tccgtttatc taggtaccag atatcgccac catggccctg agcaaagtga      900
aactgaacga tacactgaac aaggaccagc tgctgtccag cagcaagtac accatccagc      960
ggagcaccgg cgacagcatc gatacccca actacgacgt gcagaagcac atcaacaagc     1020
tgtgcggcat gctgctgatc acagaggacg ccaaccacaa gttcaccggc ctgatcggca     1080
tgctgtacgc catgagccgg ctgggccggg aggacaccat caagatcctg cgggacgccg     1140
gctaccacgt gaaggccaat ggcgtggacg tgaccacaca ccggcaggac atcaacggca     1200
```

-continued

```
aagaaatgaa gttcgaggtg ctgaccctgg ccagcctgac caccgagatc cagatcaata    1260
tcgagatcga gagccggaag tcctacaaga aaatgctgaa agaaatgggc gaggtggccc    1320
ccgagtacag acacgacagc cccgactgcg gcatgatcat cctgtgtatc gccgccctgg    1380
tgatcacaaa gctggccgct ggcgacagat ctggcctgac agccgtgatc agacgggcca    1440
acaatgtgct gaagaacgag atgaagcggt acaagggcct gctgcccaag gacattgcca    1500
acagcttcta cgaggtgttc gagaagtacc cccacttcat cgacgtgttc gtgcacttcg    1560
gcattgccca gagcagcacc agaggcggct ccagagtgga gggcatcttc gccggcctgt    1620
tcatgaacgc ctacggcgct ggccaggtga tgctgagatg gggcgtgctg ccaagagcg     1680 tgaagaacat catgctgggc cacgccagcg tgcaggccga gatggaacag gtggtggagg    1740
tgtacgagta cgcccagaag ctgggcggag aggccggctt ctaccacatc ctgaacaacc    1800
ctaaggcctc cctgctgtcc ctgacccagt tcccccactt ctccagcgtg gtgctgggaa    1860
atgccgccgg actgggcatc atgggcgagt accggggcac ccccagaaac caggacctgt    1920
acgacgccgc caaggcctac gccgagcagc tgaaagaaaa cggcgtgatc aactacagcg    1980
tgctggacct gaccgctgag gaactggaag ccatcaagca ccagctgaac cccaaggaca    2040
acgacgtgga gctgggaggc ggaggatctg cggcggagg catgagcaga cggaaccccT    2100
gcaagttcga gatccggggc cactgcctga acggcaagcg tgccacttc agccacaact    2160 acttcgagtg gcccctcat gctctgctgg tgcggcagaa cttcatgctg aaccggatcc    2220
tgaagtccat ggacaagagc atcgacaccc tgagcgagat cagcggagcc gccgagctgg    2280
acagaaccga ggaatatgcc ctgggcgtgg tgggagtgct ggaaagctac atcggctcca    2340
tcaacaacat cacaaagcag agcgcctgcg tggccatgag caagctgctg acagagctga    2400
acagcgacga catcaagaag ctgagggaca acgaggaact gaacagcccc aagatccggg    2460
tgtacaacac cgtgatcagc tacattgaga gcaaccgcaa gaacaacaag cagaccatcc    2520
atctgctgaa gcggctgccc gccgacgtgc tgaaaaagac catcaagaac ccctggaca    2580 tccacaagtc catcaccatc aacaatccca agaaagcac cgtgtctgac accaacgatc    2640
acgccaagaa caacgacacc acctgatgag cggccgcgat ctgctgtgcc ttctagttgc    2700
cagccatctg ttgtttgccc ctcccccgtg ccttccttga ccctggaagg tgccactccc    2760
actgtccttt cctaataaaa tgaggaaatt gcatcgcatt gtctgagtag gtgtcattct    2820
attctggggg gtggggtggg gcaggacagc aagggggagg attgggaaga caatagcagg    2880
catgctgggg atgcggtggg ctctatgg                                       2908
```

<210> SEQ ID NO 5
<211> LENGTH: 594
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
                20                  25                  30

Ile Asp Thr Pro Asn Tyr Asp Val Gln Lys His Ile Asn Lys Leu Cys
            35                  40                  45
```

-continued

```
Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
 65                  70                  75                  80

Lys Ile Leu Arg Asp Ala Gly Tyr His Val Lys Ala Asn Gly Val Asp
                 85                  90                  95

Val Thr Thr His Arg Gln Asp Ile Asn Gly Lys Glu Met Lys Phe Glu
                100                 105                 110

Val Leu Thr Leu Ala Ser Leu Thr Thr Glu Ile Gln Ile Asn Ile Glu
                115                 120                 125

Ile Glu Ser Arg Lys Ser Tyr Lys Lys Met Leu Lys Glu Met Gly Glu
130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
                180                 185                 190

Glu Met Lys Arg Tyr Lys Gly Leu Leu Pro Lys Asp Ile Ala Asn Ser
                195                 200                 205

Phe Tyr Glu Val Phe Glu Lys Tyr Pro His Phe Ile Asp Val Phe Val
                210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
                260                 265                 270

Gly His Ala Ser Val Gln Ala Glu Met Glu Gln Val Glu Val Tyr
                275                 280                 285

Glu Tyr Ala Gln Lys Leu Gly Gly Glu Ala Gly Phe Tyr His Ile Leu
                290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
                340                 345                 350

Tyr Ala Glu Gln Leu Lys Glu Asn Gly Val Ile Asn Tyr Ser Val Leu
                355                 360                 365

Asp Leu Thr Ala Glu Glu Leu Glu Ala Ile Lys His Gln Leu Asn Pro
                370                 375                 380

Lys Asp Asn Asp Val Glu Leu Gly Gly Gly Ser Gly Gly Gly Gly
385                 390                 395                 400

Met Ser Arg Arg Asn Pro Cys Lys Phe Glu Ile Arg Gly His Cys Leu
                405                 410                 415

Asn Gly Lys Arg Cys His Phe Ser His Asn Tyr Phe Glu Trp Pro Pro
                420                 425                 430

His Ala Leu Leu Val Arg Gln Asn Phe Met Leu Asn Arg Ile Leu Lys
                435                 440                 445

Ser Met Asp Lys Ser Ile Asp Thr Leu Ser Glu Ile Ser Gly Ala Ala
450                 455                 460

Glu Leu Asp Arg Thr Glu Glu Tyr Ala Leu Gly Val Val Gly Val Leu
```

| | | | | 465 | | | | 470 | | | | 475 | | | | 480 | |
|---|---|---|---|---|---|---|---|---|---|---|---|---|---|---|---|---|---|
| Glu | Ser | Tyr | Ile | Gly | Ser | Ile | Asn | Asn | Ile | Thr | Lys | Gln | Ser | Ala | Cys |
| | | | | | 485 | | | | | 490 | | | | | 495 | | |
| Val | Ala | Met | Ser | Lys | Leu | Leu | Thr | Glu | Leu | Asn | Ser | Asp | Asp | Ile | Lys |
| | | | | 500 | | | | | 505 | | | | 510 | | |
| Lys | Leu | Arg | Asp | Asn | Glu | Glu | Leu | Asn | Ser | Pro | Lys | Ile | Arg | Val | Tyr |
| | | | 515 | | | | | 520 | | | | | 525 | | |
| Asn | Thr | Val | Ile | Ser | Tyr | Ile | Glu | Ser | Asn | Arg | Lys | Asn | Asn | Lys | Gln |
| | | 530 | | | | | 535 | | | | | 540 | | | |
| Thr | Ile | His | Leu | Leu | Lys | Arg | Leu | Pro | Ala | Asp | Val | Leu | Lys | Lys | Thr |
| 545 | | | | | 550 | | | | | 555 | | | | | 560 |
| Ile | Lys | Asn | Thr | Leu | Asp | Ile | His | Lys | Ser | Ile | Thr | Ile | Asn | Asn | Pro |
| | | | | 565 | | | | | 570 | | | | | 575 | |
| Lys | Glu | Ser | Thr | Val | Ser | Asp | Thr | Asn | Asp | His | Ala | Lys | Asn | Asn | Asp |
| | | | 580 | | | | | 585 | | | | | 590 | | |
| Thr | Thr |

<210> SEQ ID NO 6
<211> LENGTH: 3617
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
ccattgcata cgttgtatcc atatcataat atgtacattt atattggctc atgtccaaca      60
ttaccgccat gttgacattg attattgact agttattaat agtaatcaat tacggggtca     120
ttagttcata gcccatatat ggagttccgc gttacataac ttacggtaaa tggcccgcct     180
ggctgaccgc ccaacgaccc ccgcccattg acgtcaataa tgacgtatgt tcccatagta     240
acgccaatag ggactttcca ttgacgtcaa tgggtggagt atttacggta aactgcccac     300
ttggcagtac atcaagtgta tcatatgcca gtacgccccc tattgacgtc aatgacggt      360
aaatggcccg cctggcatta tgcccagtac atgaccttat gggactttcc tacttggcag     420
tacatctacg tattagtcat cgctattacc atggtgatgc ggttttggca gtacatcaat     480
gggcgtggat agcggtttga ctcacgggga tttccaagtc tccaccccat tgacgtcaat     540
gggagtttgt tttggcacca aaatcaacgg gactttccaa aatgtcgtaa caactccgcc     600
ccattgacgc aaatgggcgg taggcgtgta cggtgggagg tctatataag cgaagcgct      660
ccctatcagt gatagagatc tccctatcag tgatagagat cgtcgacgag ctcgcggcgg     720
gcgggagtcg ctgcgcgctg ccttcgcccc gtgccccgct ccgccgccgc ctcgcgccgc     780
ccgccccggc tctgactgac cgcgttacta aaacaggtaa gtccggcctc gcgccgggt      840
tttggcgcct cccgcgggcg cccccctcct cacggcgagc gctgccacgt cagacgaagg     900
gcgcagcgag cgtcctgatc cttccgcccg gacgctcagg acagcggccc gctgctcata     960
agactcggcc ttagaacccc agtatcagca gaaggacatt ttaggacggg acttgggtga    1020
ctctagggca ctggttttct ttccagagag cggaacaggc gaggaaaagt agtcccttct    1080
cggcgattct gcggagggat ctccgtgggg cggtgaacgc cgatgatgcc tctactaacc    1140
atgttcatgt tttcttttt ttctacagg tcctgggtga cgaacaggat atcgccacca    1200
tggaactgct gatcctgaag gccaacgcca tcaccaccat cctgaccgcc gtgacctttc    1260
```

```
gcttcgccag cggccagaac atcaccgagg aattctacca gagcacctgt agcgccgtga     1320
gcaagggcta cctgagcgcc ctgagaaccg gctggtacac cagcgtgatc accatcgagc     1380
tgagcaacat caaagaaaac aagtgcaacg caccgacgc caaagtgaag ctgatcaagc     1440
aggaactgga caagtacaag aacgccgtga ccgagctgca gctgctgatg cagagcaccc     1500
ccgccaccaa caaccgggcc agacgggagc tgccccggtt catgaactac accctgaaca     1560
acgccaaaaa gaccaacgtg accctgagca agaagcggaa gcggcggttc ctgggctttc     1620
tgctgggcgt gggcagcgcc attgccagcg gcgtggccgt gtctaaggtg ctgcacctgg     1680
aaggcgaagt gaacaagatc aagagcgccc tgctgagcac caacaaggcc gtggtgtccc     1740
tgagcaacgg cgtgagcgtg ctgaccagca aggtgctgga tctgaagaac tacatcgaca     1800
agcagctgct gcccatcgtg aacaagcaga gctgcagcat cagcaacatc gagacagtga     1860
tcgagttcca gcagaagaac aaccggctgc tggaaatcac ccgggagttc agcgtgaacg     1920
ccggcgtgac caccccctgtg tccacctaca tgctgaccaa cagcgagctg ctgagcctga     1980
tcaacgacat gcccatcacc aacgaccaga aaaagctgat gagcaacaac gtgcagatcg     2040
tgcggcagca gagctactcc atcatgtcca tcatcaaaga agaggtgctg gcctacgtgg     2100
tgcagctgcc cctgtacggc gtgatcgaca ccccctgctg gaagctgcac accagccccc     2160
tgtgcaccac caacaccaaa gagggcagca acatctgcct gacccggacc gacagaggct     2220
ggtactgcga caacgccggc agcgtgtcat tctttccaca ggccgagaca tgcaaggtgc     2280
agagcaaccg ggtgttctgc gacaccatga acagcctgac cctgcccctcc gaagtgaacc     2340 tgtgcaacgt ggacatcttc aaccccaagt acgactgcaa gatcatgacc tccaagaccg     2400
acgtgtccag ctccgtgatc acctccctgg gcgccatcgt gtcctgctac ggcaagacca     2460
agtgcaccgc cagcaacaag aaccggggca tcatcaagac cttcagcaac ggctgcgact     2520
acgtgtccaa caagggggtg gacaccgtgt ccgtgggcaa caccctgtac tacgtgaaca     2580
aacaggaagg caagagcctg tacgtgaagg gcgagcccat catcaacttc tacgaccccc     2640
tggtgttccc cagcgacgag ttcgacgcca gcatcagcca ggtgaacgag aagatcaacc     2700
agagcctggc cttcatccgg aagtccgacg agctgctgca caatgtgaat gccggcaagt     2760
ccaccaccaa ctgatgagcg gccatctaat caacctctgg attacaaaat ttgtgaaaga     2820
ttgactggta ttcttaacta tgttgctcct tttacgctat gtggatacgc tgctttaatg     2880
cctttgtatc atgctattgc ttcccgtatg gctttcattt tctcctcctt gtataaatcc     2940
tggttgctgt ctctttatga ggagttgtgg cccgttgtca ggcaacgtgg cgtggtgtgc     3000
actgtgtttg ctgacgcaac ccccactggt tggggcattg ccaccacctg tcagctcctt     3060
tccgggactt tcgctttccc cctccctatt gccacggcgg aactcatcgc cgcctgcctt     3120
gcccgctgct ggacaggggc tcggctgttg gcactgacaa attccgtggt gttgtcgggg     3180
aaatcatcgt cctttccttg gctgctcgcc tgtgttgcca cctggattct gcgcgggacg     3240
tccttctgct acgtccctcc ggccctcaat ccagcggacc ttccttcccg cggcctgctg     3300
ccggctctgc ggcctcttcc gcgtcttcgc cttcgccctc agacgagtcg gatctccctt     3360
tgggccgcct ccccgcctgc ggccgcgatc tgctgtgcct tctagttgcc agccatctgt     3420
tgtttgcccc tcccccgtgc cttccttgac cctggaaggt gccactccca ctgtcctttc     3480
ctaataaaat gaggaaattg catcgcattg tctgagtagg tgtcattcta ttctgggggg     3540
tggggtgggg caggacagca agggggagga ttgggaagac aatagcaggc atgctgggga     3600
tgcggtgggc tctatgg                                                   3617
```

<210> SEQ ID NO 7
<211> LENGTH: 524
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

```
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu His Asn Val Asn Ala Gly Lys Ser Thr Thr Asn
        515                 520
```

<210> SEQ ID NO 8
<211> LENGTH: 650
<212> TYPE: DNA
<213> ORGANISM: Human cytomegalovirus

<400> SEQUENCE: 8

```
ccattgcata cgttgtatcc atatcataat atgtacattt atattggctc atgtccaaca      60
ttaccgccat gttgacattg attattgact agttattaat agtaatcaat tacggggtca     120
ttagttcata gcccatatat ggagttccgc gttacataac ttacggtaaa tggcccgcct     180
ggctgaccgc ccaacgaccc ccgcccattg acgtcaataa tgacgtatgt tcccatagta     240
acgccaatag ggactttcca ttgacgtcaa tgggtggagt atttacggta aactgcccac     300
ttggcagtac atcaagtgta tcatatgcca gtacgcccc ctattgacgt caatgacggt      360
aaatggcccg cctggcatta tgcccagtac atgaccttat gggactttcc tacttggcag     420
tacatctacg tattagtcat cgctattacc atggtgatgc ggttttggca gtacatcaat     480
gggcgtggat agcggtttga ctcacgggga tttccaagtc tccacccat tgacgtcaat      540
gggagtttgt tttggcacca aaatcaacgg gactttccaa aatgtcgtaa caactccgcc     600
ccattgacgc aaatgggcgg taggcgtgta cggtgggagg tctatataag                650
```

<210> SEQ ID NO 9
<211> LENGTH: 159
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9

```
gcgaagcgct ccctatcagt gatagagatc tccctatcag tgatagagat cgtcgacgag      60
ctcgcggcgg gcgggagtcg ctgcgcgctg ccttcgcccc gtgccccgct ccgccgccgc     120
```
ctcgcgccgc ccgccccggc tctgactgac cgcgttact            159

<210> SEQ ID NO 10
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
aaaacaggta agtcc            15

<210> SEQ ID NO 11
<211> LENGTH: 303
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
ggcctccgcg ccgggttttg gcgcctcccg cgggcgcccc cctcctcacg gcgagcgctg            60
ccacgtcaga cgaagggcgc agcgagcgtc ctgatccttc cgcccggacg ctcaggacag           120
cggcccgctg ctcataagac tcggccttag aaccccagta tcagcagaag gacattttag           180
gacgggactt gggtgactct agggcactgg ttttctttcc agagagcgga acaggcgagg           240
aaaagtagtc ccttctcggc gattctgcgg agggatctcc gtggggcggt gaacgccgat           300
gat           303

<210> SEQ ID NO 12
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gcctctacta accatgttca tgttttcttt ttttttctac aggtcctggg tgacgaacag            60

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Gly Gly Ser Gly Gly Gly
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 14

Gly Gly Gly Gly Ser Gly Gly Gly Gly
1               5
```

ENHANCED PROMOTER

CROSS-REFERENCE TO RELATED APPLICATIONS

This application is filed pursuant to 35 U.S.C. § 371 as a United States National Phase Application of International Application No. PCT/EP2018/078242 filed 16 October 2018, which claims priority to U.S. Provisional Patent Application Nos. 62/572,944, 62/572,951 and 62/572,927, all filed respectively on 16 Oct. 2017, the complete contents of each of which are hereby incorporated by reference for all purposes.

FIELD OF THE INVENTION

This invention is in the field of promoters for use in vectors such as plasmids or viruses, particularly viral vectors such as adenoviral vectors. In particular, the present invention is directed towards an enhanced human CMV promoter.

BACKGROUND OF THE INVENTION

The term "vector" refers to an agent (such as a plasmid or virus) that contains or carries genetic material and can be used to introduce exogenous genes into an organism. An adenoviral vector is one example of a type of vector.

When a vector has delivered the genetic material to the cells of an organism, RNA can be transcribed from the delivered DNA using an RNA polymerase. An RNA polymerase can recognize specific promoter elements, enabling the transcription of the DNA sequence linked to that promoter element.

A promoter is a nucleotide sequence that permits the binding of RNA polymerase and directs the transcription of the DNA. Typically, a promoter is located in a non-coding region of the DNA, proximal to the transcriptional start site. Sequence elements within promoters that function in the initiation of transcription are often characterized by consensus nucleotide sequences.

Vectors are often said to comprise an "expression cassette". The expression cassette comprises the genetic material of interest operatively linked to regulatory components in a manner which permits transgene transcription, translation, and/or expression of the DNA of interest in the host cell. The promoter is one of these regulatory components. If the DNA sequence of interest (e.g. a gene) is heterologous to the vector sequences flanking the gene, it can be referred to as a "transgene".

Examples of promoters include, but are not limited to, promoters from bacteria, yeast, plants, viruses, and mammals, including simians and humans. A great number of expression control sequences, including promoters which are internal, native, constitutive, inducible and/or tissue-specific, are known in the art.

Examples of available promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter, the SV40 promoter, the dihydrofolate reductase promoter, the β-actin promoter, the phosphoglycerol kinase (PGK) promoter, and the EF1a promoter (Invitrogen).

The CMV promoter is strong and ubiquitously active. It has the ability to drive high levels of transgene expression in many tissue types and is well known in the art.

The CASI promoter is a synthetic promoter described as a combination of the CMV enhancer, the chicken beta-actin promoter, and a splice donor and splice acceptor flanking the ubiquitin (UBC) enhancer (U.S. Pat. No. 8,865,881). SEQ ID NO: 2 is a polynucleotide sequence encoding the CASI promoter There is a need in the art for new promoters.

SUMMARY OF THE INVENTION

The invention relates to a new promoter. More particularly, the invention relates to a new human CMV promoter.

The present invention provides a promoter comprising:
(i) an hCMV enhancer sequence;
(ii) an hCMV promoter sequence;
(ii) a splice donor region;
(iv) a cell-derived enhancer sequence; and
(v) a splice acceptor region The term "cell-derived" means that the promoter is obtained from a eukaryotic (for example, human) cell.

In a preferred embodiment, the cell-derived enhancer sequence is an ubitquitin (UBC) enhancer sequence.

In another preferred embodiment, the components (i) to (v) of the promoter are provided in the order listed above, i.e. component (i) is first, (ii) is second, (iii) is third, (iv) is forth and (v) is fifth. In another embodiment, the order of the two enhancers (i.e. components (i) and (iv)) could be swapped.

In one embodiment, the promoter comprises one or more of the following sequences:
(i) the hCMV enhancer; and
(ii) the hCMV promoter sequences; of SEQ ID NO: 8; and/or
(iii) the splice donor region of SEQ ID NO:10; and/or
(iv) the UBC enhancer sequence of SEQ ID NO:11; and/or
(v) the splice acceptor region of SEQ ID NO: 12

In some embodiments, the promoter comprises at least about 50%, at least about 60%, at least about 70%, at least about 80%, at least about 85%, at least about 90%, at least about 95%, at least about 96%, at least about 97%, at least about 98%, at least about 99%, or more, sequence identity to SEQ ID NO: 8, SEQ ID NO:10, SEQ ID NO:11 and/or SEQ ID NO:12. In some embodiments, the parts (i) to (v) of the promoter consist of the relevant sequence.

In an embodiment, the promoter comprises:
(i) the hCMV enhancer; and
(ii) the hCMV promoter sequences; of SEQ ID NO: 8; and
(iii) the splice donor region of SEQ ID NO:10;
(iv) the UBC enhancer sequence of SEQ ID NO:11; and
(v) the splice acceptor region of SEQ ID NO: 12

In one embodiment, the promoter further comprises:
(vi) a fragment of the beta-actin sequence In this embodiment comprising a fragment of the beta-actin sequence, the fragment of the chicken beta-actin sequence preferably comprises a 5' untranslated region of the chicken beta actin sequence and does not contain the promter sequence. In one embodiment, the chicken beta actin sequence may have at least about 50%, at least about 60%, at least about 70%, at least about 80%, at least about 85%, at least about 90%, at least about 95%, at least about 96%, at least about 97%, at least about 98%, at least about 99%, or more, sequence identity to SEQ ID NO: 9. In an embodiment comprising (vi) a fragment of the beta-actin sequence, this fragment is preferably found between the hCMV promoter region (ii) and the splice donor region (iii).

In another aspect, the present invention relates to a new promoter having at least about 84.1%, or more, identity to SEQ ID NO: 3. In some embodiments, the promoter can include a nucleic acid sequence having at least about 84.5%, at least about 85%, at least about 86%, at least about 87%, at least about 88%, at least about 89%, or more, sequence identity to SEQ ID NO: 3

In some embodiments, the promoter can include a nucleic acid sequence having at least about 90%, at least about 95%, at least about 96%, at least about 97%, at least about 98%, at least about 99%, or more, sequence identity to SEQ ID NO: 3. In some embodiments, the promoter comprises or consists of a nucleic acid sequence of SEQ ID NO: 3.

In another aspect, the invention relates to a vector, such as an adenoviral vector or a plasmid, containing the new promoter described above. All of the features described above in relation to the promoter may be incorporated into the vector. For example, in one embodiment, the invention provides an adenoviral vector of the invention, the adenoviral vector comprises an expression cassette, wherein the expression cassette comprises a transgene and a promoter, wherein the promoter comprises:
  (i) an hCMV enhancer sequence;
  (ii) an hCMV promoter sequence;
  (iii) a splice donor region;
  (iv) a cell-dervied enhancer sequence; and
  (v) a splice acceptor region.

Another example of a vector of the invention is an adenoviral vector comprising an expression cassette, wherein the expression cassette comprises a transgene and a promoter, wherein the promoter comprises a nucleic acid sequence having at least 84.1% identity to SEQ ID NO: 3.

In a further example, a vector (e.g. an adenoviral vector) comprises a first and a second expression cassette, wherein each expression cassette comprises a transgene and a promoter, wherein the promoter of the first expression cassette and/or the second expression cassette is the new promoter described above. In one embodiment, the first expression cassette comprises the promoter. In another embodiment, the second expression cassette comprises the promoter.

For example, in one embodiment, an adenoviral vector of the invention comprises a first and a second expression cassette, wherein each expression cassette comprises a transgene and a promoter, wherein the promoter of the first expression cassette and/or the second expression cassette is a promoter comprising:
  (i) an hCMV enhancer sequence;
  (ii) an hCMV promoter sequence;
  (iii) a splice donor region;
  (iv) a cell-dervived sequence; and
  (v) a splice acceptor region.

In an additional example, an adenoviral vector comprises a first and a second expression cassette, wherein each expression cassette comprises a transgene and a promoter, wherein the promoter of the first expression cassette and/or the second expression cassette is a promoter having at least 84.1% identity to SEQ ID NO: 3.

The vectors (e.g. adenoviral vectors) of the invention are useful as components of immunogenic compostions for the induction of an immune response in a subject, methods for their use in treatment and processes for manufacture. The adenoviral vector of the present invention is preferably derived from a non-human simian adenovirus, also referred to as a "simian adenovirus". Preferably, the simian adenoviral vector of the present invention is a chimp adenovirus (for example ChAd155 or ChAd83).

The present invention also provides a composition comprising the above-mentioned adenoviral vector and a pharmaceutically acceptable excipient. In addition, the present invention provides the above-mentioned adenoviral vector or composition comprising such an adenoviral vector for use as a medicament, a vaccine, and/or for the therapy or prophylaxis of a disease.

The invention also provides a method of inducing an immune response in a subject comprising administering the the above-mentioned adenoviral vector or composition described above to the subject. A vector or composition of the invention can be used in the manufacture of a medicament for the prevention or treatment of a disease

Figure 1:
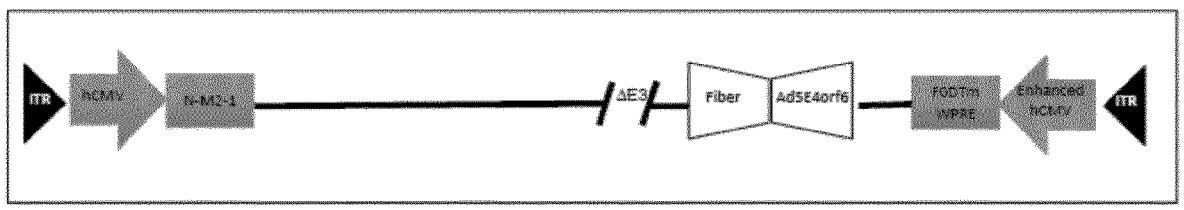
FIG. 1: A simian adenoviral construct according to the invention with a dual expression cassette. Inverted terminal repeats (ITR) flank the 3' and 5' ends; human CMV (hCMV) is the cytomegalovirus promoter; Enchanced hCMV is the enhanced cytomegalovirus promoter; N-M2-1 and FΔTM are the RSV antigens; WPRE is the Woodchuck Hepatitis Postranscriptional Regulatory Element; ΔE3 denotes that the early gene 3 is deleted; fiber denotes the adenoviral gene encoding the fiber protein; and Ad5E4orf6 in a substitute in the early gene 4 (E4) region.

The vector of FIG. 1 was constructed by inserting a first transgene expression cassette in place of the E1 region of the adenoviral genome, and a second transgene expression cassette in the HE2 region, i.e., downstream of the right ITR.

Figure 2:
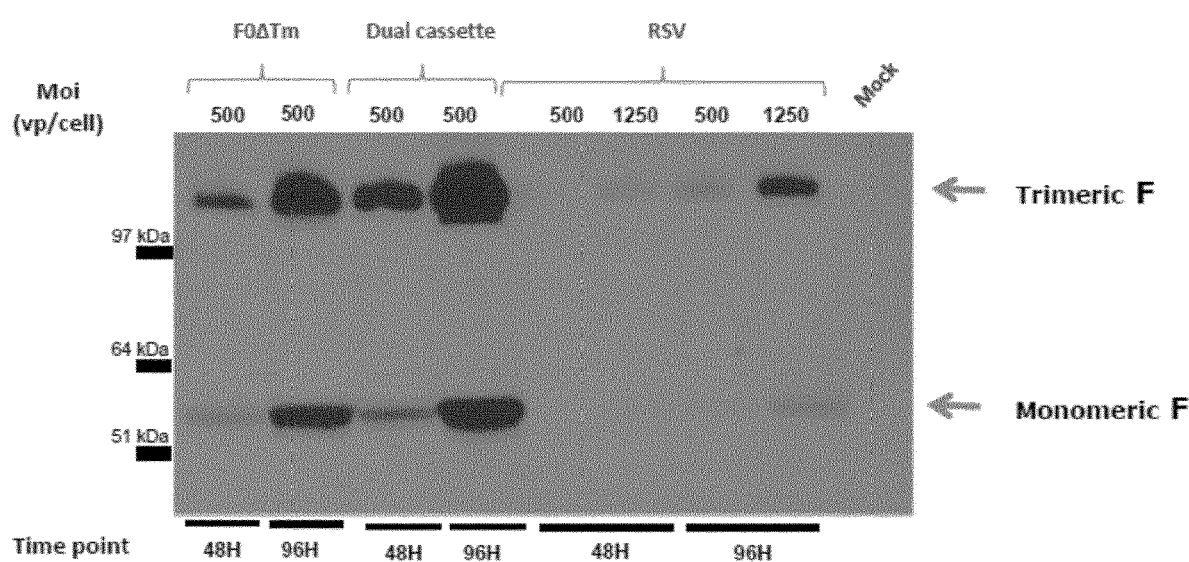

FIG. 2: Comparison of the expression levels of vectors expressing FΔTM transgene in a MRC5 cell line, demonstrated by western blot at 48 hours and 96 hours post-infection under non-reducing conditions. Cells were infected at multiplicities of infection of 500 and 1250.

Figure 3:
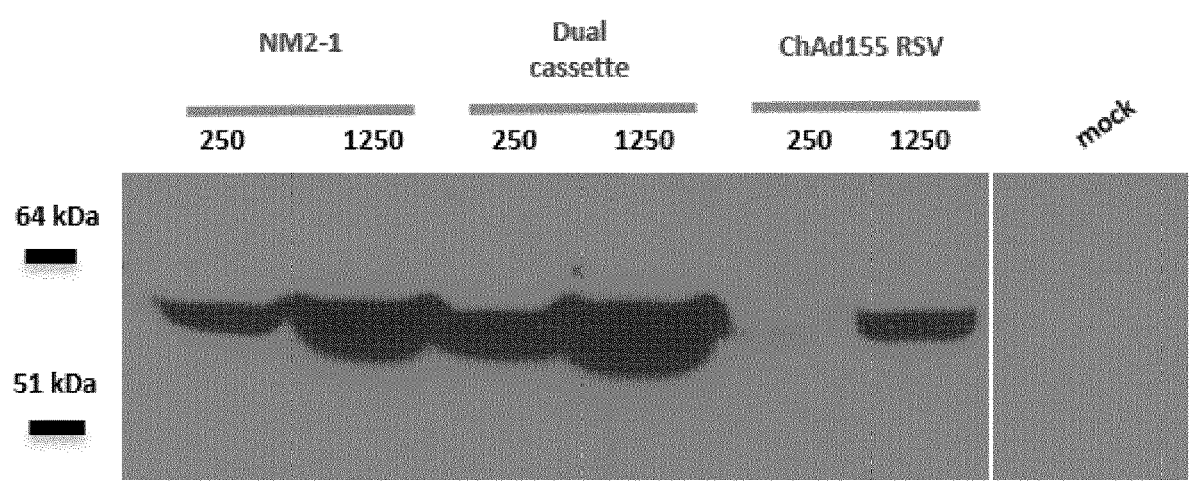

FIG. 3: Comparison of the expression levels of vectors expressing NM2-1 transgene in a MRC5 cell line, demonstrated by western blot at 48 hours post-infection under reducing conditions.

Cells were infected at multiplicities of infection of 250 and 1250.

Figure 4:
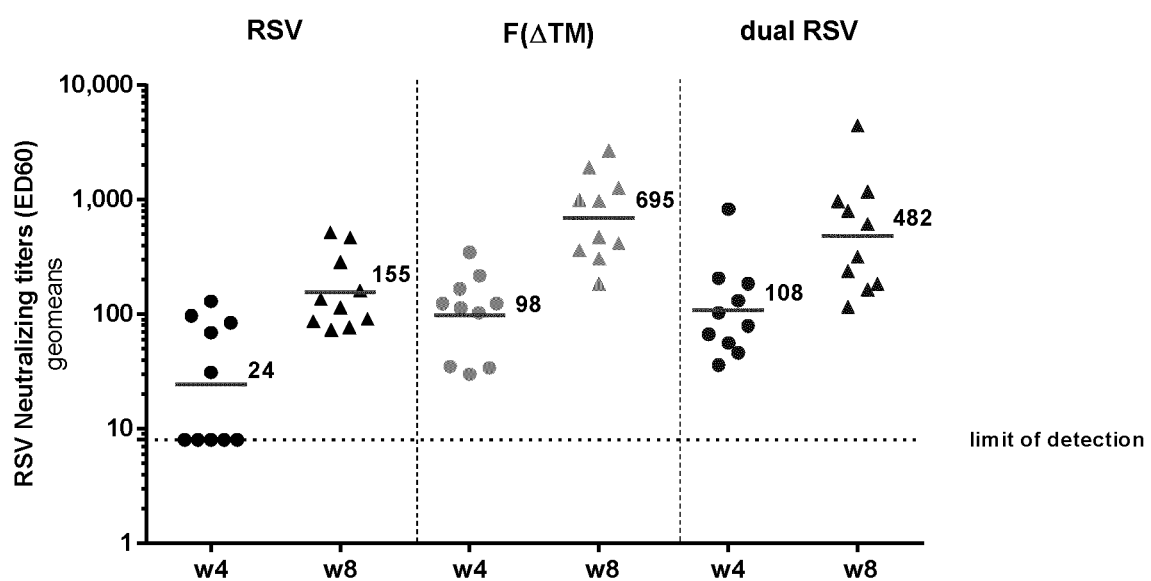

FIG. 4: Comparison of the immunogencity from ChAd155 vectors expressing the RSV antigen FΔTm. The data was collected at 4 weeks and 8 weeks after vaccination with a dose of $5 \times 10^8$ virus particles.

Figure 5:
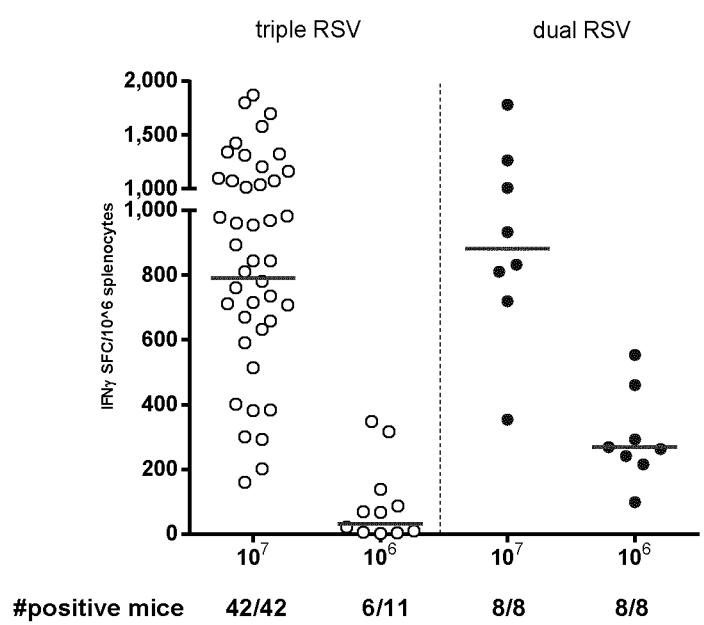

FIG. 5: Comparison of the immunogencity from ChAd155 vectors expressing the M2 RSV antigen. The data was collected at 3 weeks after vaccination with a dose of either $10^7$ or $10^6$ virus particles.

Figure 6:
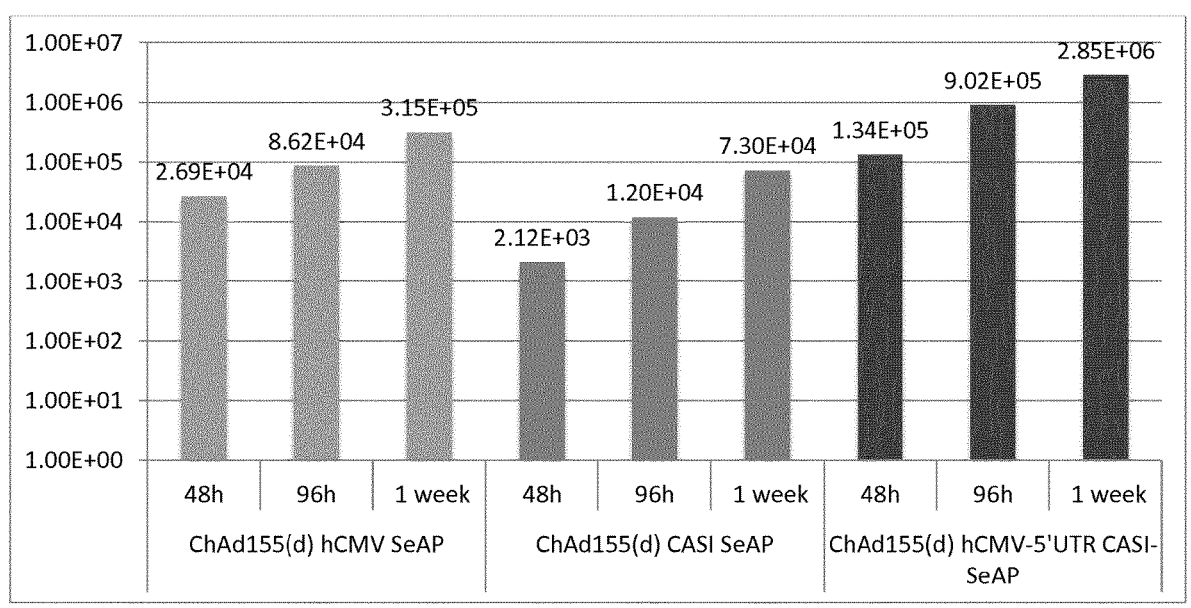

FIG. 6: SeAP expression in MRC5 cells by ChAd155 with different promoters.

Figure 7:
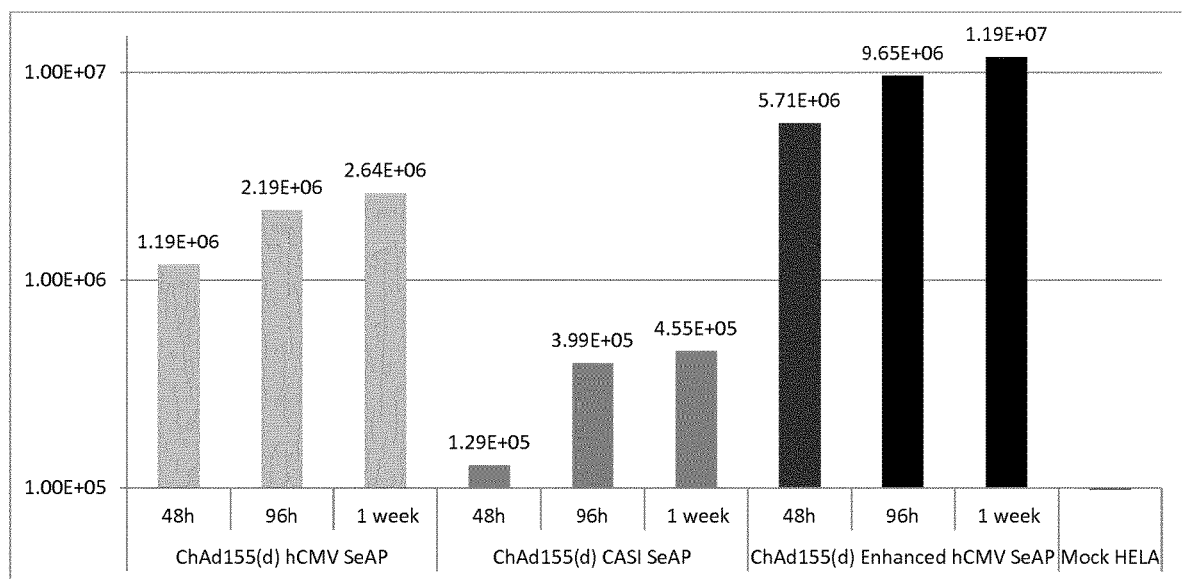

FIG. 7: SeAP expression in HeLa cells by ChAd155 with different promoters.

ANNOTATION OF THE SEQUENCES

SEQ ID NO: 1—Polynucleotide sequence encoding wild type ChAd155
SEQ ID NO: 2—Polynucleotide sequence encoding the CASI promoter
SEQ ID NO: 3—Polynucleotide sequence encoding the enhanced hCMV promoter
SEQ ID NO: 4—Polynucleotide sequence encoding the hCMV NM2 bghpolyA cassette
SEQ ID NO: 5—NM2 protein sequence
SEQ ID NO: 6—Polynucleotide sequence encoding the hCMV F0 WPRE bghpolyA cassette
SEQ ID NO: 7—F0 protein sequence SEQ ID NO: 8—Polynucleotide sequence encoding the hCMV promoter and enhancer sequence (nucleotides 1-650 of SEQ ID NO: 3).

SEQ ID NO: 9—Polynucleotide sequence encoding a Chicken Beta-Actin Fragment (nucleotides 651-809 of SEQ ID NO: 3).

SEQ ID NO: 10—Polynucleotide sequence encoding the Splice Donor Region (nucleotides 810-824 of SEQ ID NO: 3).

SEQ ID NO: 11—Polynucleotide sequence encoding the ubiquitin (UBC) enhancer (nucleotides 825-1127 of SEQ ID NO: 3).

SEQ ID NO: 12—Polynucleotide sequence encoding the Splice Acceptor Region (nucleotides 1128-1187 of SEQ ID NO: 3).

DETAILED DESCRIPTION OF THE INVENTION

Adenoviruses

Adenoviruses are nonenveloped icosahedral viruses with a linear double stranded DNA genome of approximately 36 kb. Adenoviruses can transduce numerous cell types of several mammalian species, including both dividing and nondividing cells, without integrating into the genome of the host cell. They have been widely used for gene transfer applications due to their proven safety, ability to achieve highly efficient gene transfer in a variety of target tissues, and large transgene capacity. Human adenoviral vectors are currently used in gene therapy and vaccines but have the drawback of a high worldwide prevalence of pre-existing immunity, following previous exposure to common human adenoviruses.

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The hexon accounts for the majority of the structural components of the capsid, which consists of 240 trimeric hexon capsomeres and 12 penton bases. The hexon has three conserved double barrels and the top has three towers, each tower containing a loop from each subunit that forms most of the capsid. The base of the hexon is highly conserved between adenoviral serotypes, while the surface loops are variable. The penton is another adenoviral capsid protein; it forms a pentameric base to which the fiber attaches. The trimeric fiber protein protrudes from the penton base at each of the 12 vertices of the capsid and is a knobbed rod-like structure. The primary role of the fiber protein is to tether the viral capsid to the cell surface via the interaction of the knob region with a cellular receptor. Variations in the flexible shaft, as well as knob regions of fiber, are characteristic of the different adenovral serotypes.

The adenoviral genome has been well characterized. The linear, double-stranded DNA is associated with the highly basic protein VII and a small peptide pX (also termed mu). Another protein, V, is packaged with this DNA-protein complex and provides a structural link to the capsid via protein VI. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The 5' end of the adenoviral genome contains the 5' cis-elements necessary for packaging and replication; i.e., the 5' ITR sequences (which can function as origins of replication) and the native 5' packaging enhancer domains, which contain sequences necessary for packaging linear adenoviral genomes and enhancer elements for the E1 promoter. The 3' end of the adenoviral genome includes 3' cis-elements, including the ITRs, necessary for packaging and encapsidation. The virus also comprises a virus-encoded protease, which is necessary for processing some of the structural proteins required to produce infectious virions.

The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. The E1 gene is considered a master switch, it acts as a transcription activator and is involved in both early and late gene transcription. E2 is involved in DNA replication; E3 is involved in immune modulation and E4 regulates viral mRNA metabolism. During the late phase of infection, expression of the late genes L1-L5, which encode the structural components of the viral particles, is activated. Late genes are transcribed from the Major Late Promoter (MLP) with alternative splicing.

HE1 and HE2 sites were identified as potential insertion sites for a transgene since the insertion in these specific points does not interrupt the coding sequences or important regulatory sequences of a chimp adenovirus, such as a Type C or E chimp adenovirus, for example, ChAd155 and ChAd83. The HE1 and HE2 sites can be identified by sequence alignment in any chimp adenovirus. Therefore, cloning of expression cassettes in the HE1 and HE2 sites of the ChAd genomes doesn't impact the virus replication cycle.

Adenoviral Replication

Historically, adenovirus vaccine development has focused on defective, non-replicating vectors. They are rendered replication defective by deletion of the E1 region genes, which are essential for replication. Typically, non-essential E3 region genes are also deleted to make room for exogenous transgenes. An expression cassette comprising the transgene under the control of an exogenous promoter is then inserted. These replication-defective viruses are then produced in E1-complementing cells.

The term "replication-defective" or "replication-incompetent" adenovirus refers to an adenovirus that is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Suitably, E1 and optionally E3 and/or E4 are deleted. If deleted, the aforementioned deleted gene region will suitably not be considered in the alignment when determining percent identity with respect to another sequence.

In some embodiments of the invention, the adenoviral vector is a replication defective adenovirus. For example, in the embodiments of an adenoviral vector with two expression cassettes, the first expression cassette is inserted in the deleted E1 region and so these adenoviruses will be replication defective.

In other embodiments, the adenoviral vector is a replication competent adenovirus. The term "replication-competent" adenovirus refers to an adenovirus which can replicate in a host cell in the absence of any recombinant helper proteins comprised in the cell. Suitably, a "replication-competent" adenovirus comprises intact structural genes and the following intact or functionally essential early genes: E1A, E1B, E2A, E2B and E4. Wild type adenoviruses isolated from a particular animal will be replication competent in that animal.

Vectors of the Invention

Viral vectors based on non-human simian adenovirus represent an alternative to the use of human derived vectors for gene therapy and genetic vaccines. Certain adenoviruses isolated from non-human simians are closely related to adenoviruses isolated from humans, as demonstrated by their efficient propagation in cells of human origin. As humans typically do not develop immunity to simian adenoviruses, they promise to provide an improved alternative to human adenoviral uses.

"Low seroprevalence" may mean having a reduced pre-existing neutralizing antibody level as compared to human adenovirus 5 (Ad5). Similarly or alternatively, "low seroprevalence" may mean less than about 40% seroprevalence, less than about 30% seroprevalence, less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titer (defined as a 50% neutralisation titer >200) using methods as described in Hum. Gene Ther. (2004) 15:293.

In one embodiment, the adenoviral vector of the present invention is derived from a nonhuman simian adenovirus, also referred to as a "simian adenovirus." Numerous adenoviruses have been isolated from nonhuman simians such as chimpanzees, bonobos, rhesus macaques, orangutans and gorillas. Vectors derived from these adenoviruses can induce strong immune responses to transgenes encoded by these vectors. Certain advantages of vectors based on nonhuman simian adenoviruses include a relative lack of cross-neutralizing antibodies to these adenoviruses in the human target population, thus their use overcomes the pre-existing immunity to human adenoviruses. For example, some simian adenoviruses have no cross reactivity with preexisting human neutralizing antibodies and cross-reaction of certain chimpanzee adenoviruses with pre-existing human neutralizing antibodies is only present in 2% of the target population, compared with 35% in the case of certain candidate human adenovirus vectors (Sci. Transl. Med. (2012) 4:1).

Adenoviral vectors of the invention may be derived from a non-human adenovirus, such as a simian adenovirus, e.g., from chimpanzees (*Pan troglodytes*), bonobos (*Pan paniscus*), gorillas (Gorilla gorilla) and orangutans (*Pongo abelii* and *Pongo pygnaeus*). They include adenoviruses from Group B, Group C, Group D, Group E and Group G. Chimpanzee adenoviruses include, but are not limited to ChAd3, ChAd19, ChAd25.2, ChAd26, ChAd27, ChAd29, ChAd30, ChAd31, ChAd32, ChAd33, ChAd34, ChAd35, ChAd37, ChAd38, ChAd39, ChAd40, ChAd63, ChAd83, ChAd155, ChAd15, SadV41 and ChAd157. Alternatively, adenoviral vectors may be derived from nonhuman simian adenoviruses isolated from bonobos, such as PanAd1, PanAd2, PanAd3, Pan 5, Pan 6, Pan 7 (also referred to as C7) and Pan 9. Vectors may include, in whole or in part, a nucleotide encoding the fiber, penton or hexon of a nonhuman adenovirus.

In an embodiment of the adenoviral vectors of the invention, the adenoviral vector has a seroprevalence of less than 40%, less than 30%, less than 20%, less than 10% or less than 5% in human subjects, preferably no seroprevalence in human subjects and more preferably no seroprevalence in human subjects that have not previously been in contact with a chimpanzee adenovirus.

In embodiments of the adenoviral vectors of the invention, the adenoviral DNA is capable of entering a mammalian target cell, i.e. it is infectious. An infectious recombinant adenoviral vector of the invention can be used as a prophylactic or therapeutic vaccine and for gene therapy. Thus, in an embodiment, the recombinant adenoviral vector comprises an endogenous molecule for delivery into a target cell. The target cell is a mammalian cell, e.g. a bovine cell, a canine cell, a caprine cell, a *cervine* cell, a chimpanzee cell, a chiroptera cell, an equine cell, a feline cell, a human cell, a lupine cell, an ovine cell, a porcine cell, a rodent cell, an ursine cell or a vulpine cell. Theendogenous molecule for delivery into a target cell is an expression cassette.

In an embodiment of the invention, the vector comprises a left ITR region, a deleted E1 region, then a deleted E3 region, and, optionally, additional enhancer elements; these are followed by a fiber region, an E4 region and a right ITR. Translation occurs in the rightward and leftward directions. In this embodiment, the first expression cassette is inserted in the deleted E1 region, and the second expression cassette is insertion in the deleted E3 region. In a further embodiment, the promoters of the two expression cassettes are CMV promoters. In a yet further embodiment, the enhancer element is the Hepatitis B Postranslational Regulatory Element (HPRE) or the Woodchuck Hepatitis Postranslational Element (WPRE).

In one embodiment of the invention, the vector comprises left and right ITR regions; a deleted E1 region; at least a partially deleted E3 region; a fiber region; an E4 region; two expression cassettes, each comprising: a promoter and at least one an antigen of interest and, optionally, one or more enhancer elements. The first expression cassette is inserted in the deleted E1 region, and the second expression cassette is inserted at the HE1 site, i.e., between the stop codons of the fiber gene and an E4 region ("the HE1 site"). The ChAd155 HE1 insertion site is between bp 34611 and 34612 of the wild type ChAd155 sequence. The ChAd83 HE1 insertion site is between bp 33535 and 33536 of the wild type ChAd83 sequence. Translation occurs in the rightward and leftward directions. In a further embodiment, the promoters are CMV promoters. In a preferred embodiment, one promoter is a CMV promoter and the other is a eCMV promoter. In a yet further embodiment, the enhancer element is HPRE or WPRE.

In a further embodiment, the vector comprises left and right ITR regions; a deleted E1 region; at least a partially deleted E3 region; a fiber region; an E4 region; two expression cassettes, each comprising: a promoter, at least one antigen of interest and, optionally, one or more enhancer elements. The first expression cassette is inserted in the deleted E1 region, and the second expression cassette is inserted at the HE2 site, i.e., between the end of the left ITR and the cap site of the E4 mRNA ("the HE2 site"). The ChAd155 HE2 insertion site is between bp 37662 and 37663 of the wild type ChAd155 sequence. The ChAd83 HE2 insertion site is between bp 36387 and 36388 of the wild type ChAd83 sequence. Translation occurs in the rightward and leftward directions. In a further embodiment, the promoters are CMV promoters. In a preferred embodiment, one promoter is a CMV promoter and the other is a eCMV promoter. In a yet further embodiment, the enhancer element is HPRE or WPRE (the enhancer element increases expression of the transgene).

The HE1 and HE2 sites were identified as insertion sites for a transgene, as the insertion in these specific points does not interrupt the coding sequences or regulatory sequences of ChAd155 and ChAd83. Therefore, inserting expression cassettes in the HE1 or HE2 sites of the ChAd genome does not affect the viral replication cycle.

In an embodiment of the invention, the vector is a functional or an immunogenic derivative of an adenoviral vector. By "derivative of an adenoviral vector" is meant a modified version of the vector, e.g., one or more nucleotides of the vector are deleted, inserted, modified or substituted.

Further Regulatory Elements

Regulatory elements, i.e., expression control sequences, in addition to promoter sequences, include appropriate transcription initiation, termination and enhancer sequences; efficient RNA processing signals such as splicing and polyadenylation (poly A) signals including rabbit beta-globin polyA; tetracycline regulatable systems, microRNAs, post-transcriptional regulatory elements e.g., WPRE, posttranscriptional regulatory element of woodchuck hepatitis virus); sequences that stabilize cytoplasmic mRNA; sequences that enhance translation efficiency (e.g., Kozak consensus sequence); sequences that enhance protein stability; and when desired, sequences that enhance secretion of an encoded product.

Optionally, vectors carrying transgenes encoding therapeutically useful or immunogenic products may also include selectable markers or reporter genes. The reporter gene may be chosen from those known in the art. Suitable reporter genes include, but are not limited to enhanced green fluorescent protein, red fluorescent protein, luciferase and secreted embryonic alkaline phosphatase (seAP), which may include sequences encoding geneticin, hygromicin or purimycin resistance, among others. Such selectable reporters or marker genes (whaich may or may not be located outside the viral genome to be packaged into a viral particle) can be used to signal the presence of the plasmids in bacterial cells, such as ampicillin resistance. Other components of the vector may include an origin of replication.

A "posttranscriptional regulatory element," as used herein, is a DNA sequence that, when transcribed, enhances the expression of the transgene(s) or fragments thereof that are delivered by viral vectors of the invention. Postranscriptional regulatory elements include, but are not limited to the Hepatitis B Virus Postranscriptional Regulatory Element (HPRE) and the Woodchuck Hepatitis Postranscriptional Regulatory Element (WPRE). The WPRE is a tripartite cis-acting element that has been demonstrated to enhance transgene expression driven by certain, but not all promoters In embodiments of the invention, a ChAd155 vector may comprise one or more of a promoter, an enhancer, and a reporter gene. For example, vectors of the invention may comprise ChAd155-enhanced hCMV-SeAP ChAd155-CASI-seAP and ChAd155-hCMV-seAP, optionally with a tetracycline on/off transcriptional control and ChAd155-CMV-hFerL-chEF1-seAP with a tetracycline on/off transcriptional control.

In embodiments of the invention, a ChAd83 vector may comprise one or more of a promoter, an enhancer, and a reporter gene. For example, vectors of the invention may comprise ChAd155 enhanced hCMV SeAP, ChAd83 enhanced hCMV SeAP, ChAd155-CASI-seAP and ChAd83-hCMV-seAP, optionally with a tetracycline on/off transcriptional control and ChAd83-CMV-hFerL-chEF1-seAP with a tetracycline on/off transcriptional control.

Vectors of the invention are generated using techniques provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Transgenes

A "transgene" is a nucleic acid sequence, heterologous to the vector sequences flanking the transgene, which encodes a polypeptide of interest. The nucleic acid coding sequence is operatively linked to regulatory components in a manner which permits transgene transcription, translation, and/or expression in a host cell. In embodiments of the invention, the vectors express transgenes at a therapeutic or a prophylactic level. A "functional derivative" of a transgenic polypeptide is a modified version of a polypeptide, e.g., wherein one or more amino acids are deleted, inserted, modified or substituted.

The transgene may be used for prophylaxis or treatment, e.g., as a vaccine for inducing an immune response, to correct genetic deficiencies by correcting or replacing a defective or missing gene, or as a cancer therapeutic. As used herein, induction of an immune response refers to the ability of a protein to induce a T cell and/or a humoral antibody immune response to the protein.

The immune response elicited by the transgene may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing cytokines, e.g. interferon gamma (IFN gamma), tumor necrosis factor alpha (TNF alpha) and/or interleukin 2 (IL2). Alternatively, or additionally, the antigen specific T cell response comprises a CD8+ T cell response, such as a response involving CD8+ T cells expressing cytokines, e.g., IFN gamma, TNF alpha and/or IL2.

The composition of the transgene sequence will depend upon the use to which the resulting vector will be put. In an embodiment, the transgene is a sequence encoding a product which is useful in biology and medicine, such as a prophylactic transgene, a therapeutic transgene or an immunogenic transgene, e.g., protein or RNA. Protein transgenes include antigens. Antigenic transgenes of the invention induce an immunogenic response to a disease causing organism.

Transgenes such rabies virus antigens, e.g., rabies glycoprotein (RG), respiratory syncytial virus (RSV) antigens, human immunodeficiency virus (HIV) antigens, or fragments thereof would be suitable for use with promoters of the invention. However, the invention is not limited to use with such transgenes.

As a result of the redundancy in the genetic code, a polypeptide can be encoded by a variety of different nucleic acid sequences. Coding is biased to use some synonymous codons, i.e., codons that encode the same amino acid, more than others. By "codon optimized," it is meant that modifications in the codon composition of a recombinant nucleic acid are made without altering the amino acid sequence. Codon optimization has been used to improve mRNA expression in different organisms by using organism-specific codon-usage frequencies.

In addition to, and independently from, codon bias, some synonymous codon pairs are used more frequently than others. This codon pair bias means that some codon pairs are overrepresented and others are underrepresented. Codon pair deoptimization has been used to reduce viral virulence. For example, it has been reported that polioviruses modified to contain underrepresented codon pairs demonstrated decreased translation efficiency and were attenuated compared to wild type poliovirus (Science (2008) 320:1784). Engineering a synthetic attenuated virus by codon pair deoptimization can produce viruses that encode the same amino acid sequences as wild type but use different pairwise arrangements of synonymous codons. Viruses attenuated by codon pair deoptimization generated up to 1000-fold fewer plaques compared to wild type, produced fewer viral particles and required about 100 times as many viral particles to form a plaque.

In contrast, polioviruses modified to contain codon pairs that are overrepresented in the human genome acted in a manner similar to wild type RNA and generated plaques identical in size to wild type RNA (Coleman et al. (2008) Science 320:1784). This occurred despite the fact that the virus with overrepresented codon pairs contained a similar number of mutations as the virus with underrepresented codon pairs and demonstrated enhanced translation compared to wild type. This observation suggests that codon pair optimized constructs would be expected to act in a manner similar to their non-codon pair optimized counterparts and would not be expected to provide a functional advantage. Without wishing to be constrained by theory, this may be because natural evolution has optimized codon pairing.

A construct of the invention may comprise a codon optimized nucleic acid sequence. Alternatively or additionally, a vector of the invention comprises a codon optimized sequence of a transgene or an immunogenic derivative or fragment thereof. A construct of the invention may comprise a codon pair optimized nucleic acid sequence. Alternatively or additionally, a vector of the invention comprises or consists of a codon pair optimized sequence of a transgene or an immunogenic derivative or fragment thereof.

Respiratory Syncytial Virus (RSV) Transgenes

Infection with RSV does not confer full protective immunity. Infection in infancy is followed by symptomatic RSV re-infections which continue throughout adulthood. These re-infections generally go undiagnosed because they usually present as common acute upper respiratory tract infections. In more vulnerable persons (e.g., immunocompromised adults or elderly), re infections can however also lead to severe disease. Both arms of the immune system (humoral and cellular immunity) are involved in protection from severe disease [Guvenel, 2014].

The humoral immune response is capable of neutralizing the virus and inhibiting viral replication, thereby playing a major role in protection against lower respiratory RSV infection and severe disease [Piedra, 2003]. Passive immunization, in the form of Immunoglobulin G (IgG) RSV-neutralizing monoclonal antibodies (Synagis) given prophylactically, has been shown to prevent RSV disease to some extent in premature infants and newborns with bronchopulmonary dysplasia or underlying cardiopulmonary disease [Cardenas, 2005].

T cells are also involved in the control of RSV disease. Lethal RSV infections have been described in patients with low CD8 T cells counts, as in the case of severe combined immunodeficiency, bone marrow and lung transplant recipients [Hertz, 1989]. The histopathology of fatal cases of RSV infection of newborns shows that there is a relative paucity of CD8 T cells in the lung infiltrate [Welliver, 2007]. Moreover, the presence of CD8 T cells producing Interferon-gamma (IFN-γ) has been associated with diminished Th2 responses and reduced eosinophilia in animal models of RSV [Castilow, 2008; Stevens, 2009].

Suitable antigens of RSV which are useful as immunogens to immunize a human or non-human animal can be selected from: the fusion protein (F), the attachment protein (G), the matrix protein (M2) and the nucleoprotein (N). The term "F protein" or "fusion protein" or "F protein polypeptide" or "fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. The term "M protein" or "matrix protein" or "M protein polypeptide" refers to a polypeptide or protein having all or part of an amino acid sequence of an RSV Matrix protein and may include either or both of the M2-1 (which may be written herein as M2.1) and M2-2 gene products. Likewise, the term "N protein" or "Nucleocapsid protein" or "N protein polypeptide" refers to a polypeptide or protein having all or part of an amino acid sequence of an RSV Nucleoprotein.

Two groups of human RSV strains have been described, the A and B groups, based mainly on differences in the antigenicity of the G glycoprotein. Numerous strains of RSV have been isolated to date, any of which are suitable in the context of the antigens of the immunogenic combinations disclosed herein. Exemplary strains indicated by GenBank and/or EMBL Accession number can be found in US published application number 2010/0203071 (WO2008114149), which is incorporated herein by reference for the purpose of disclosing the nucleic acid and polypeptide sequences of RSV F and G proteins suitable for use in present invention. In an embodiment, the RSV F protein can be an ectodomain of an RSV F Protein (FΔTM).

Exemplary M and N protein nucleic acids and protein sequences can be found, e.g., in US published application number 2014/0141042 (WO2012/089833), which are incorporated herein for purpose of disclosing the nucleic acid and polypeptide sequences of RSV M and N proteins suitable for use in present invention.

Transgene nucleic acids may encode an RSV F antigen and RSV, M and N antigens. More specifically, the nucleic acids may encode an RSV FΔTM antigen (fusion (F) protein deleted of the transmembrane and cytoplasmic regions), and RSV M2-1 (transcription anti-termination) and N (nucleocapsid) antigens.

Fusion (F) Protein Deleted of the Transmembrane and Cytoplasmic Regions (FΔTM)

The RSV F protein is a major surface antigen and mediates viral fusion to target cells. The F protein is an antigen which is highly conserved among RSV subgroups and strains. The F protein is a target for neutralizing antibodies, including the prophylactic RSV-neutralizing monoclonal antibody Synagis. Deletion of the transmembrane region and cytoplasmic tail permits secretion of the FΔTM protein. Neutralizing antibodies including Synagis, that recognize this soluble form of the F protein, inhibit RSV infectivity in vitro [Magro, 2010].

Nucleocapsid (N) Protein

The N protein is an internal (non-exposed) antigen, highly conserved between RSV strains and known to be a source of many T cell epitopes [Townsend, 1984]. The N protein is essential for the replication and transcription of the RSV genome. The primary function of the N protein is to encapsulate the virus genome for the purposes of RNA transcription, replication and packaging and protects it from ribonucleases.

Transcription Anti-Termination (M2-1) Protein

The M2-1 protein is a transcription anti-termination factor that is important for the efficient synthesis of full-length messenger RNAs (mRNAs) as well as for the synthesis of polycistronic readthrough mRNAs, which are characteristic of non-segmented negative-strand RNA viruses. M2-1 is an internal (non-exposed) antigen, which is highly conserved between RSV strains and known to be a source of many T cell epitopes [Townsend, 1984].

N-M2-1 Fusion Protein

A polynucleotide encoding a linker is positioned between the polynucleotide encoding an RSV N antigen, or fragment thereof, and the polynucleotide encoding an RSV M2.1 antigen, or fragment thereof. Thus, in certain preferred examples, an expression cassette contains a transgene which encodes a fused RSV viral protein N-linker-M2.1 It is preferred that the linker is a flexible linker, preferably a flexible linker comprising an amino acid sequence according to SEQ ID NO: 13 (Gly-Gly-Gly-Ser-Gly-Gly-Gly) or SEQ ID NO: 14 (Gly-Gly-Gly-Gly-Ser-Gly-Gly-Gly-Gly).

Delivery of Adenoviral Vectors

In some embodiments, the recombinant adenoviral vector of the invention is administered to a subject by epicutaneous administration, intradermal administration, intramuscular injection, intraperitoneal injection, intravenous injection, nasal administration, oral administration, rectal administration, subcutaneous injection, transdermal administration or intravaginal administration.

In an embodiment of the invention, the vectors can be administered intramuscularly (IM), i.e., injection directly into muscle. Muscles are well vascularized and the uptake is typically rapid.

Adjuvants

Approaches to establishing strong and lasting immunity to specific pathogens include addition of adjuvants to vaccines. By "adjuvant" is meant an agent that augments, stimulates, activates, potentiates or modulates the immune response to an active ingredient of the composition. The adjuvant effect may occur at the cellular or humoral level, or both. Adjuvants stimulate the response of the immune system to the actual antigen but have no immunological effect themselves. Alternatively or additionally, adjuvented compositions of the invention may comprise one or more immunostimulants. By "immunostimulant" it is meant an agent that induces a general, temporary increase in a subject's immune response, whether administered with the antigen or separately.

A composition of the invention may be administered with or without an adjuvant. Alternatively, or additionally, the composition may comprise, or be administered in conjunction with, one or more adjuvants (e.g. vaccine adjuvants), in particular the composition comprises an immunologically effective amount of a vector of the invention encoding a transgene.

Methods of Use/Uses

Methods are provided for inducing an immune response against a disease caused by a pathogen in a subject in need thereof comprising a step of administering an immunologically effective amount of a construct or composition as disclosed herein. In some embodiments are provided the use of the constructs or compositions disclosed herein for inducing an immune response to a transgenic antigen in a subject in need thereof. Vectors of the invention may be applied for the prophylaxis, treatment or amelioration of diseases due to infection.

Methods of the invention include the use of a vector of the invention in medicine. They include the use of a vector of the invention for the treatment of a disease caused by a pathogen. A vector of the invention can be used in the manufacture of a medicament for treating a disease caused by a pathogen.

Effective immunization with adenoviral vectors depends on the intrinsic immnomodulatory capability of the adenoviral vector backbone. Immunologically less potent adenoviruses induce less antigen expression. Effective immunization also depends on the ability of the promoter to drive strong and sustained transgene expression. For example, adenoviral vectors driven by the cytomegalovirus immediate-early (CMV-IE) promoter do not sustain long-term transgene expression because they induce cytokines that dampen expression.

By "subject" is intended a vertebrate, such as a mammal e.g. a human or a veterinary mammal. In some embodiments the subject is human.

General

Vectors of the invention are generated using techniques and sequences provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word or is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%.

The present invention will now be further described by means of the following non-limiting examples.

EXAMPLES

Example 1: Construction of a Chimpanzee Adenovirus

Wild type chimpanzee adenoviruses type 155 (ChAd155) (WO 2016/198621) isolated from healthy chimpanzees using standard procedures and were constructed as replication defective viruses as described in Sci Transl Med (2012) 4:1 and WO 2010/086189.

The ChAd155 is constructed by inserting two transgene expression cassettes into two different locations in the adeno:

(1) The first expression cassette components comprise the classical human CMV (hCMV) promoter and N.M2-1

RSV antigens. This first expression cassette is inserted into the E1 region of the adeno (after the E1 region has been deleted).

(2) The second expression cassette comprises an enhanced classical human CMV (enhanced hCMV) promoter, the FΔTM RSV antigen and a WPRE enhancer. This first expression cassette is inserted into the HE2 region of the adeno (after the HE2 region has been deleted).

This vector comprising a dual expression cassette is shown in FIG. 1.

In the construct of FIG. 1, Ad5E4orf6 has been substituted into the early gene 4 (E4) region. The substitution is necessary to increase the productivity in HEK 293 cells.

Example 2: Transgene Expression from the Chimpanzee Adenovirus of Example 1

Western blot analysis was performed to compare the level of transgene expression in the ChAd155 vector of Example 6 (labelled "Dual" or "Dual cassette" in the figures) in MRC5 cells with:
(i) a vector comprising a single F expression cassette (ChAd155-FΔTM, labelled "F0ΔTm"),
(ii) a vector comprising a single NM2 expression cassette (ChAd155-NM2, labelled "NM2-1"), and
(iii) the vector of Example 5 comprising a single expression cassette containing the F and N-M2 RSV antigens (ChAd155-FΔTM.NM2, also labelled "RSV")

The western blot analysis is shown in FIG. 2 and FIG. 3.

As shown in FIG. 2, the cells were infected with ChAd155-FΔTM, ChAd155-FΔTM.NM2 ("RSV") or the ChAd155 dual cassette at a multiplicity of infection of 500 viral particles per cell. In addition, cells were infected with ChAd155-FΔTM.NM2 ("RSV") at a multiplicity of infection of 1250 viral particles per cell. The cells were harvested at 48 hours and 96 hours post infection, extracts prepared using standard methods and an equivalent amount of total cell extract loaded onto SDS-PAGE gels.

FIG. 2 shows that the ChAd155 dual cassette provides an expression level of the F antigen which is comparable to ChAd155FΔTM and higher than ChAd155-FΔTM.NM2 in MRC5 cells.

As shown in FIG. 3, the cells were infected with ChAd155-NM2, ChAd155-FΔTM.NM2 ("RSV") or the ChAd155 dual cassette of Example 6 at a multiplicity of infection of 250 and 1250 viral particles per cell. The cells were harvested at 48 hours post infection, extracts prepared using standard methods and an equivalent amount of total cell extract loaded onto SDS-PAGE gels.

In FIG. 3, the ChAd155 dual cassette provides NM2-1 expression level comparable to the ChAd155-NM2 single vector and higher than ChAd155-FΔTM.NM2 ("RSV") in MRC5 cells.

Example 3: Immunogencity of the Chimpanzee Adenovirus of Example 1

The immunogenicity of the dual expression cassette of Example 6 was evaluated in CD1 outbred mice (10 per group). The experiment was performed by injecting $5 \times 10^8$ viral particles intramuscularly into the mice. The B-cell response was measured at 4 and 8 weeks after the immunization by measuring the RSV neutralising titres. Each dot represents the response in a single mouse, and the line corresponds to the mean for each dose group. The results of this analysis are shown in FIG. 4.

FIG. 4 shows that the ChAd155 dual cassette provides a B-cell response comparable to ChAd155FΔTM and higher than that produced by ChAd155-FΔTM.NM2 ("RSV").

The immunogenicity of the dual expression cassette of Example 6 was also evaluated in BALB/c inbred mice (48, 11 or 8 per group). The experiment was performed by injecting $10^7$ or $10^8$ viral particles intramuscularly. The T-cell response was measured 3 weeks after the immunization by ex vivo IFN-gamma enzyme-linked immunospot (ELISpot) using a M2 peptide T cell epitope mapped in BALB/c mice. The results are shown in FIG. 11, expressed as IFN-gamma Spot Forming Cells (SFC) per million of splenocytes. Each dot represents the response in a single mouse, and the line corresponds to the mean for each dose group. Injected dose in number of virus particles are shown on the x axis. The results are shown in FIG. 5.

FIG. 5 shows that the ChAd155 dual cassette provides a T-cell response higher than that produced by ChAd155-FΔTM.NM2 ("RSV", the results for which are obtained from historical data). This difference in response is greater for the $10^6$ dose.

FIG. 5 refers to "#positive mice", i.e. the number of mice which responded to the vaccine.

Example 3: SeAP Expression in MRC5 Cells by ChAd155 with Different Promoters

The secreted embryonic alkaline phosphatase (SeAP) system is widely used to study promoter activity. The SeAP reporter gene encodes a truncated for of the human placental alkaline phosphatase gene that lacks the membrane anchoring domain. Therefore, the SeAP protein is secreted into the cell supernatant and allows promoter activity to be determined without disturbing the cells.

FIG. 6 shows the SeAP expression in MRC5 cells from ChAd155 vectors constructed with different promoters. The three different ChAd155 vectors used in this example are as follows:
A ChAd155 with the known human CMV (hCMV) promoter;
A ChAd155 with the known CASI promoter; and
A ChAd155 with the new enhanced hCMV promoter In this experiment, the MRC5 were infected with moi=250 vp/cell, and measurement of the SeAP took place at 2 days (48 hours), 4 days (96 hours) and 7 days (1 week) post-infection with the ChAd155 viruses.

As can be seen from FIG. 6, the vectors constructed with the new enhanced hCMV promoter showed higher SeAP expression than the other two vectors at every time point measured.

Example 4: SeAP Expression in HeLa Cells by ChAd155 with Different Promoters

FIG. 7 shows the SeAP expression in HeLa cells from ChAd155 vectors constructed with different promoters. As with Example 3, the three different ChAd155 vectors used in this experiment were as follows:
A ChAd155 (d) with the known human CMV (hCMV) promoter;
A ChAd155 (d) with the known CASI promoter; and
A ChAd155 (d) with the new enhanced hCMV promoter In this experiment, the HeLa were infected with moi=50 vp/cell, and measurement of the SeAP took place at 2 days (48 hours), 4 days (96 hours) and 7 days (1 week) post-infection with the ChAd155 viruses.

As can be seen from FIG. 7, the vectors constructed with the new enhanced hCMV promoter showed higher SeAP expression than the other two vectors at every time point measured.

DESCRIPTION OF THE SEQUENCES

SEQ ID NO: 1 Polynucleotide sequence encoding wild type ChAd155
CATCATCAATAATATACCTTATTTTGGATTGAAGCCAATATGATAATGAGATGGGCGGCGCGGGGCGGGAG
GCGGGTCCGGGGGCGGGCCGGCGGGCGGGGCGGTGTGGCGGAAGTGGACTTTGTAAGTGTGGCGGATGTGACTTGCT
AGTGCCGGGCGCGGTAAAAGTGACGTTTTCCGTGCGCGACAACGCCCACGGGAAGTGACATTTTTCCCGCGGTTTTT
ACCGGATGTTGTAGTGAATTTGGGCGTAACCAAGTAAGATTTGGCCATTTTCGCGGGAAAACTGAAACGGGGAAGTG
AAATCTGATTAATTTCGCGTTAGTCATACCGCGTAATATTTGTCGAGGGCCGAGGGACTTTGGCCGATTACGTGGAG
GACTCGCCCAGGTGTTTTTTGAGGTGAATTTCCGCGTTCCGGGTCAAAGTCTCCGTTTTATTATTATAGTCAGCTGA
CGCGGAGTGTATTTATACCCTCTGATCTCGTCAAGTGGCCACTCTTGAGTGCCAGCGAGTAGAGTTTTCTCCTCTGC
CGCTCTCCGCTCCGCTCCGCTCGGCTCTGACACCGGGGAAAAAATGAGACATTTCACCTACGATGGCGGTGTGCTCA
CCGGCCAGCTGGCTGCTGAAGTCCTGGACACCCTGATCGAGGAGGTATTGGCCGATAATTATCCTCCCTCGACTCCT
TTTGAGCCACCTACACTTCACGAACTCTACGATCTGGATGTGGTGGGGCCCAGCGATCCGAACGAGCAGGCGGTTTC
CAGTTTTTTTCCAGAGTCCATGTTGTTGGCCAGCCAGGAGGGGGTCGAACTTGAGACCCCTCCTCCGATCGTGGATT
CCCCCGATCCGCCGCAGCTGACTAGGCAGCCCGAGCGCTGTCGGGACCTGAGACTATGCCCCAGCTGCTACCTGAG
GTGATCGATCTCACCTGTAATGAGTCTGGTTTTCCACCCAGCGAGGATGAGGACGAAGAGGGTGAGCAGTTTGTGTT
AGATTCTGTGGAACAACCCGGGCGAGGATGCAGGTCTTGTCAATATCACCGGAAAAACACAGGAGACTCCCAGATTA
TGTGTTCTCTGTGTTATATGAAGATGACCTGTATGTTTATTTACAGTAAGTTTATCATCTGTGGGCAGGTGGGCTAT
AGTGTGGGTGGTGGTCTTTGGGGGTTTTTTAATATATGTCAGGGGTTATGCTGAAGACTTTTTTATTGTGATTTTT
AAAGGTCCAGTGTCTGAGCCCGAGCAAGAACCTGAACCGGAGCCTGAGCCTTCTCGCCCCAGGAGAAAGCCTGTAAT
CTTAACTAGACCCAGCGCACCGGTAGCGAGAGGCCTCAGCAGCGCGGAGACCACCGACTCCGGTGCTTCCTCATCAC
CCCCGGAGATTCACCCCCTGGTGCCCCTGTGTCCCGTTAAGCCCGTTGCCGTGAGAGTCAGTGGGCGGCGGTCTGCT
GTGGAGTGCATTGAGGACTTGCTTTTTGATTCACAGGAACCTTTGGACTTGAGCTTGAAACGCCCCAGGCATTAAAC
CTGGTCACCTGGACTGAATGAGTTGACGCCTATGTTTGCTTTTGAATGACTTAATGTGTATAGATAATAAAGAGTGA
GATAATGTTTTAATTGCATGGTGTGTTTAACTTGGGCGGAGTCTGCTGGGTATATAAGCTTCCCTGGGCTAAACTTG
GTTACACTTGACCTCATGGAGGCCTGGGAGTGTTTGGAGAACTTTGCCGGAGTTCGTGCCTTGCTGGACGAGAGCTC
TAACAATACCTCTTGGTGGTGGAGGTATTTGTGGGGCTCTCCCCAGGGCAAGTTAGTTTGTAGAATCAAGGAGGATT
ACAAGTGGGAATTTGAAGAGCTTTTGAAATCCTGTGGTGAGCTATTGGATTCTTTGAATCTAGGCCACCAGGCTCTC
TTCCAGGAGAAGGTCATCAGGACTTTGGATTTTTCCACACCGGGGCGCATTGCAGCCGCGGTTGCTTTTCTAGCTTT
TTTGAAGGATAGATGGAGCGAAGAGACCCACTTGAGTTCGGGCTACGTCCTGGATTTTCTGGCCATGCAACTGTGGA
GAGCATGGATCAGACACAAGAACAGGCTGCAACTGTTGTCTTCCGTCCGCCCGTTGCTGATTCCGGCGGAGGAGCAA
CAGGCCGGGTCAGAGGACCGGGCCCGTCGGGATCCGGAGGAGAGGGCACCGAGGCCGGGCGAGAGGAGCGCGCTGAA
CCTGGGAACCGGGCTGAGCGGCCATCCACATCGGGAGTGAATGTCGGGCAGGTGGTGGATCTTTTTCCAGAACTGCG
GCGGATTTTGACTATTAGGGAGGATGGGCAATTTGTTAAGGGTCTTAAGAGGGAGAGGGGGGCTTCTGAGCATAACG
AGGAGGCCAGTAATTTAGCTTTTAGCTTGATGACCAGACACCGTCACAGGTGCATCACTTTTCAGCAGATTAAGGAC
AATTGTGCCAATGAGTTGGATCTGTTGGGTCAGAAGTATAGCATAGAGCAGCTGACCACTTACTGGCTGCAGCCGGG
TGATGATCTGGAGGAAGCTATTAGGGTGTATGCTAAGGTGGCCCTGCGGCCCGATTGCAAGTACAAGCTCAAGGGGC
TGGTGAATATCAGGAATTGTTGCTACATTTCTGGCAACGGGCGGAGGTGGAGATAGAGACCGAAGACAGGGTGGCT
TTCAGATGCAGCATGATGAATATGTGGCCGGGGGTGCTGGGCATGACGGGTGGTGATTATGAATGTGAGGTTCAC
GGGGCCCAACTTTAACGGCACGGTGTTTTTGGGGAACACCAACCTGGTCCTGCACGGGGTGAGCTTCTATGGGTTTA
ACAACACCTGTGTGGAGGCCTGGACCGATGTGAAGGTCCGCGGTTGCGCCTTTTATGGATGTTGGAAGGCCATAGTG
AGCCGCCCTAAGAGCAGGAGTTCCATTAAGAAATGCTTGTTTGAGAGGTGCACCTTGGGGATCCTGGCCGAGGGCAA
CTGCAGGGTGCGCCACAATGTGGCCTCCGAGTGCGGTTGCTTCATGCTAGTCAAGAGCGTGGCGGTAATCAAGCATA
ATATGGTGTGCGGCAACAGCGAGGACAAGGCCTCACAGATGCTGACCTGCACGGATGGCAACTGCCACTTGCTGAAG
ACCATCCATGTAACCAGCCACAGCCGGAAGGCCTGGCCCGTGTTCGAGCACAACTTGCTGACCCGCTGCTCCTTGCA
TCTGGGCAACAGGCGGGGGGTGTTCCTGCCCTATCAATGCAACTTTAGTCACACCAAGATCTTGCTAGAGCCCGAGA
GCATGTCCAAGGTGAACTTGAACGGGGTGTTTGACATGACCATGAAGATCTGGAAGGTGCTGAGGTACGACGAGACC
AGGTCCCGGTGCAGACCCTGCGAGTGCGGGGGCAAGCATATGAGGAACCAGCCCGTGATGCTGGATGTGACCGAGGA
GCTGAGGACAGACCACTTGGTTCTGGCCTGCACCAGGGCCGAGTTTGGTTCTAGCGATGAAGACACAGATTGAGGTG
GGTGAGTGGGCGTGGCCTGGGGTGGTCATGAAAATATATAAGTTGGGGGTCTTAGGGTCTCTTTATTTGTGTTGCAG
AGACCGCCGGAGCCATGAGCGGGAGCAGCAGCAGCAGCAGTAGCAGCAGCGCCTTGGATGGCAGCATCGTGAGCCCT
TATTTGACGACGCGGATGCCCCACTGGGCCGGGGTGCGTCAGAATGTGATGGGCTCCAGCATCGACGGCCGACCCGT
CCTGCCCGCAAATTCCGCCACGCTGACCTATGCGACCGTCGCGGGACGCCGTTGGACGCCACCGCCGCCGCCGCCG
CCACCGCAGCCGCCTCGGCCGTGCGCAGCCTGGCCACGGACTTTGCATTCCTGGGACCACTGGCGACAGGGGCTACT
TCTCGGGCCGCTGCTGCCGCCGTTCGCGATGACAAGCTGACCGCCCTGCTGGCGCAGTTGGATGCGCTTACTCGGGA
ACTGGGTGACCTTTCTCAGCAGGTCATGGCCCTGCGCCAGCAGGTTCCTCCCTGCAAGCTGGCGGGAATGCTTCTC
CCACAAATGCCGTTTAAGATAAATAAAACCAGACTCTGTTTGGATTAAAGAAAAGTAGCAAGTGCATTGCTCTCTTT
ATTTCATAATTTTCCGCGCGCGATAGGCCCTAGACCAGCGTTCTCGGTCGTTGAGGGTGCGGTGTATCTTCTCCAGG
ACGTGGTAGAGGTGGCTCTGGACGTTGAGATACATGGGCATGAGCCCGTCCCGGGGTGGAGGTAGCACCACTGCAG
AGCTTCATGCTCCGGGGTGGTGTTGTAGATGATCCAGTCGTAGCAGGAGCGCTGGGCATGGTGCCTAAAAATGTCCT
TCAGCAGCAGGCCGATGGCCAGGGGGAGGCCCTTGGTGTAAGTGTTTACAAAACGGTTAAGTTGGGAAGGGTGCATT
CGGGGAGAGATGATGTGCATCTTGGACTGTATTTTTAGATTGGCGATGTTTCCGCCCAGATCCCTTCTGGGATTCAT
GTTGTGCAGGACCACCAGTACAGTGTATCCGGTGCACTTGGGGAATTTGTCATGCAGCTTAGAGGGAAAAGCGTGGA
AGAACTTGGAGACGCCTTTGTGGCCTCCCAGATTTTCCATGCATTCGTCCATGATGATGGCAATGGGCCCCGCGGGAA
GCAGTTGGGCAAAGATATTTCTGGGGTCGCTGACGTCGTAGTTGTGTTCCAGGGTGAGGTCGTCATAGGCCATTTT
TACAAAGCGCGGGCGGAGGGTGCCCGACTGGGGGATGATGGTCCCCTCTGGCCCTGGGGCGTAGTTGCCCTCGCAGA
TCTGCATTTCCCAGGCCTTAATCTCGGAGGGGGGAATCATATCCACCTGCGGGGCGATGAAGAAAACGGTTTCCGGA
GCCGGGGAGATTAACTGGGATGAGAGCAGGTTTCTAAGCAGCTGTGATTTTCCACAACCGGTGGGCCCATAAATAAC
ACCTATAACCGGTTGCAGCTGGTAGTTTAGAGAGCTGCAGCTGCCGTCGTCCCGGCAGGGGGGCCACCTCGTTGA
GCATGTCCCTGACGCGCATGTTCTCCCCGACCAGATCCGCCAGAAGGCGCTCGCCGCCCAGGGACAGCTCTTGC
AAGGAAGCAAAGTTTTTCAGCGGCTTGAGGCCGTCCGCCGTGGGCATGTTTTTCAGGGTCTGGCTCAGCAGCTCCAG
GCGGTCCCAGAGCTCGGTGACGTGCTCTACGGCATCTCTATCCAGCATATCTCCTGTTTCGCGGGTTGGGCGACT
TTCGCTGTAGGGCACCAAGCGGTGGTCGTCCAGCGGGGCAGAGTCATGTCCTTCCATGGGCGCAGGGTCCTCGTCA
GGGTGGTCTGGGTCACGGTGAAGGGGTGCGCTCCGGGCTGAGCGCTTGCCAAGGTGCGCTTGAGGCTGGTTCTGCTG
GTGCTGAAGCGCTGCCGGTCTTCGCCCTGCGCGTCGGCCAGGTAGCATTTGACCATGGTGTCATAGTCCAGCCCCTC

DESCRIPTION OF THE SEQUENCES

```
CGCGGCGTGTCCCTTGGCGCGCAGCTTGCCCTTGGAGGTGGCGCCGCACGAGGGGCAGAGCAGGCTCTTGAGCGCGT
AGAGCTTGGGGGCGAGGAAGACCGATTCGGGGGAGTAGGCGTCCGCGCCGCAGACCCCGCACACGGTCTCGCACTCC
ACCAGCCAGGTGAGCTCGGGGCGCGCCGGGTCAAAAACCAGGTTTCCCCCATGCTTTTTGATGCGTTTCTTACCTCG
GGTCTCCATGAGGTGGTGTCCCCGCTCGGTGACGAAGAGGCTGTCCGTGTCTCCGTAGACCGACTTGAGGGGTCTTT
TCTCCAGGGGGGTCCCTCGGTCTTCCTCGTAGAGGAACTCGGACCACTCTGAGACGAAGGCCCGCGTCCAGGCCAGG
ACGAAGGAGGCTATGTGGGAGGGGTAGCGGTCGTTGTCCACTAGGGGGTCCACCTTCTCCAAGGTGTGAAGACACAT
GTCGCCTTCCTCGGCGTCCAGGAAGGTGATTGGCTTGTAGGTGTAGGCCACGTGACCGGGGGTTCCTGACGGGGGGG
TATAAAAGGGGGTGGGGGCGCGCTCGTCGTCACTCTCTTCCGCATCGCTGTCTGCGAGGGCCAGCTGCTGGGGTGAG
TATTCCCTCTCGAAGGCGGGCATGACCTCCGCGCTGAGGTTGTCAGTTTCCAAAAACGAGGAGGATTTGATGTTCAC
CTGTCCCGAGGTGATACCTTTGAGGGTACCCGCGTCCATCTGGTCAGAAAACACGATCTTTTTATTGTCCAGCTTGG
TGGCGAACGACCCGTAGAGGGCGTTGGAGAGCAGCTTGGCGATGGAGCGCAGGGTCTGGTTCTTGTCCCTGTCGGCG
CGCTCCTTGGCCGCGATGTTGAGCTGCACGTACTCGCGCGCGACGCAGCGCCACTCGGGGAAGACGGTGGTGCGCTC
GTCGGGCACCAGGCGCACGCGCCAGCCGCGGTTGTGCAGGGTGACCAGGTCCACGCTGGTGGCGACCTCGCCGCGCA
GGCGCTCGTTGGTCCAGCAGAGACGGCCGCCCTTGCGCGAGCAGAAGGGGGGCAGGGGGTCGAGCTGGGTCTCGTCC
GGGGGGTCCGCGTCCACGGTGAAAACCCCGGGGCGCAGGCGCGCGTCGAAGTAGTCTATCTTGCAACCTTGCATGTC
CAGCGCCTGCTGCCAGTCGCGGGCGGCGAGCGCGCGCTCGTAGGGGTTGAGCGGCGGGCCCCAGGGCATGGGGTGGG
TGAGTGCGGAGGCGTACATGCCGCAGATGTCATAGACGTAGAGGGGCTCCCGCAGGACCCCGATGTAGGTGGGGTAG
CAGCGGCCGCCGCGGATGCTGGCGCGCACGTAGTCATACAGCTCGTGCGAGGGGGCGAGGAGGTCGGGGCCCAGGTT
GGTGCGGGCGGGGCGCTCCGCGCGAAGACGATCTGCCTGAAGATGGCATGCGAGTTGGAAGAGATGGTGGGGCGCT
GGAAGACGTTGAAGCTGGCGTCCTGCAGGCCGACGGCGTCGCGCACGAAGGAGGCGTAGGAGTCGCGCAGCTTGTGT
ACCAGCTCGGCGGTGACCTGCACGTCGAGCGCGCAGTAGTCGAGGGTCTCGCGGATGATGTCATATTTAGCTGCCC
CTTCTTTTTCCACAGCTCGCGGTTGAGGACAAACTCTTCGCGGTCTTTTCCAGTACTCTTGGATCGGGAAACCGTCCG
GTTCCGAACGGTAAGAGCCTAGCATGTAGAACTGGTTGACGGCCTGGTAGGCGCAGCAGCCCTTCTCCACGGGGAGG
GCGTAGGCCTGCGCGGCCTTGCGGAGCGAGGTGTGGGTCAGGGCGAAGGTGTCCCTGACCATGACTTTGAGGTACTG
GTGCTTGAAGTCGGAGTCGTCGCAGCCGCCCCGCTCCCAGAGCGAGAAGTCGGTGCGCTTCTTGGAGCGGGGGTTGG
GCAGAGCGAAGGTGACATCGTTGAAGAGGATTTTGCCCGCGCGGGGCATGAAGTTGCGGGTGATGCGGAAGGGCCCC
GGCACTTCAGAGCGGTTGTTGATGACCTGGGCGGCGAGCACGATCTCGTCGAAGCCGTTGATGTTGTGGCCCACGAT
GTAGAGTTCCAGGAAGCGGGGCCGGCCCTTTACGGTGGGCAGCTTCTTTAGCTCTTCGTAGGTGAGCTCCTCGGGCG
AGGCGAGGCCGTGCTCGGCCAGGGCCCAGTCCGCGAGGTGCGGGTTGTCTCTGAGGAAGGACTTCCAGAGGTCGCGG
GCCAGGAGGGTCTGCAGGCGGTCTCTGAAGGTCCTGAACTGGCGGCCCACGGCCATTTTTTCGGGGGTGATGCAGTA
GAAGGTGAGGGGGTCTTGCTGCCAGCGGTCCCAGTCGAGCTGCAGGGCGAGGTCGCGCGCGGCGGTGACCAGGCGCT
CGTCGCCCCCGAATTTCATGACCAGCATGAAGGGCACGAGCTGCTTTCCGAAGGCCCCCATCCAAGTGTAGGTCTCT
ACATCGTAGGTGACAAAGAGGCGCTCCGTGCGAGGATGCGAGCCGATCGGGAAGAACTGGATCTCCCGCCACCAGTT
GGAGGAGTGGCTGTTGATGTGGTGGAAGTAGAAGTCCCGTCGCCGGGCCGAACACTCGTGCTGGCTTTTGTAAAAGC
GAGCGCAGTACTGGCAGCGCTGCACGGGCTGTACCTCATGCACGAGATGCACCTTTCGCCCGCGCACGAGGAAGCCG
AGGGGAAATCTGAGCCCCCCGCCTGGCTCGCGGCATGGCTGGTTCTCTTCTACTTTGGATGCGTGTCCGTCTCCGTC
TGGCTCCTCGAGGGGTGTTACGGTGGAGCGGACCACCACGCGCGCGAGCCGCAGGTCCAGATATCGGCGCGCGGCG
GTCGGAGTTTGATGACGACATCGCGCAGCTGGGAGCTGTCCATGGTCTGGAGCTCCCGCGGCGGCGGCAGGTCAGCC
GGGAGTTCTTGCAGGTTCACCTCGCAGAGTCGGGCCAGGGCGCGGGGCAGGTCTAGGTGGTACCTGATCTCTAGGGG
CGTGTTGGTGGCGGCGTCGATGGCTTGCAGGAGCCCGCAGCCCCGGGGGGCGACGACGGTGCCCCGCGGGGTGGTGG
TGGTGGTGGCGGTGCAGCTCAGAAGCGGTGCCGCGGGCGGGCCCCGGAGGTAGGGGGGGCTCCGGTCCCGCGGGCA
GGGGCGGCAGCGGCACGTCGGCGTGGAGCGCGGGCAGGAGTTGGTGCTGTGCCCGGAGGTTGCTGGCGAAGGCGACG
ACGCGGCGGTTGATCTCCTGGATCTGGCGCCTCTGCGTGAAGACGACGGGCCCGGTGAGCTTGAACCTGAAAGAGAG
TTCGACAGAATCAATCTCGGTGTCATTGACCGCGGCCTGGCGCAGGATCTCCTGCACGTCTCCCGAGTTGTCTTGGT
AGGCGATCTCGGCCATGAACTGCTCGATCTCTTCCTCCTGGAGGTCTCCGCGTCCGGCGCGTTCCACGGTGGCCGCC
AGGTCGTTGGAGATGCGCCCCATGAGCTGCGAGAAGGCGTTGAGTCCGCCCTCGTTCCAGACTCGGCTGTAGACCAC
GCCCCCCTGGTCATCGCGGGCGCGCATGACCACCTGCGCGAGGTTGAGCTCCACGTGCCGCGCGAAGACGGCGTAGT
TGCGCAGACGCTGGAAGAGGTAGTTGAGGGTGGTGGCGGTGTGCTCGGCCACGAAGAAGTTCATGACCCAGCGGCGC
AACGTGGATTCGTTGATGTCCCCCAAGGCCTCCAGCCGTTCCATGGCCTCGTAGAAGTCCACGGCGAAGTTGAAAAA
CTGGAGTTGCGCGCCGACACGGTCAACTCCTCCTCAGAAGACGGATGAGCTCGGCGACGGTGTCGCGCACCTCGC
GCTCGAAGGCTATGGGGATCTCTTCCTCCGCTAGCATCACCACCTCCTCCTCTTCCTCCTCTTCTGGCACTTCCATG
ATGGCTTCCTCCTCTTCGGGGGTGGCGGCGGCGGCGGTGGGGAGGGGGCGCTCTGCGCCGGCGGCGGCGCACCGG
GAGGCGGTCCACGAAGCGCGCGATCATCTCCCCGCGGCGGCGGCATGGTCTCGGTGACGGCGCGGCCGTTCTCCC
GGGGGCGCAGTTGGAAGACGCCGCCGGACATCTGGTGCTGGGGCGGGTGGCCGTGAGGCAGCGAGACGGCGCTGACG
ATGCATCTCAACAATTGCTGCGTAGGTACGCCGCCGAGGGACCTGAGGGAGTCCATATCCACCGGATCCGAAAACCT
TTCGAGGAAGGCGTCTAACCAGTCGCAGTCGCAAGGTAGGCTGAGCACCGTGGCGGGCGGCGGGGGGTGGGGGGAGT
GTCTGGCGGAGGTGCTGCTGATGATGTAATTGAAGTAGGCGGACTTGACACGGCGGATGGTGACAGGAGCACCATG
TCCTTGGGTCCGGCCTGCTGGATGCGGAGGCGGTCGGCTATGCCCCAGGCTTCGTTCTGGCATCGGCGCAGGTCCTT
GTAGTAGTCTTGCATGAGCCTTTCCACCGGCACCTCTTCTCTTCCTCTTCTGCTTCTTCCATGTCTGCTTCGGCCC
TGGGGCGGCGCCGCGCCCCCTGCCCCCATGCGCGTGACCCCGAACCCCTGAGCGGTTGGAGCAGGGCCAGGTCG
GCGACGACGCTCGGCCAGGATGGCCTGCTGCACCTGCGTGAGGGTGGTTTGGAAGTCATCCAAGTCCACGAAGCG
GTGGTAGGCGCCCGTGTTGATGGTGTAGGTGCAGTTGGCCATGACGGACCAGTTGACGGTCTGGTGGCCCGGTTGCG
ACATCTCGGTGTACCTGAGTCGCGAGTAGGCGCGGGAGTCGAAGACGTAGTCGTTGCAAGTCCGCACCAGGTACTGG
TAGCCCACCAGGAAGTGCGGCGGCGGCTGGCGGTAGAGGGGCCAGCGCAGGGTGGCGGGGGCTCCGGGGCAGGTC
TTCCAGCATGAGGCGGTGGTAGGCGTAGATGTACCTGGACATCCAGGTGATACCCGCGGCGGTGGTGGAGGCGCGCG
GGAAGTCGCGCACCCGGTTCCAGATGTGCGCAGGGGCAGAAAGTGCTCATGGTAGGCGTGCTCTGTCCAGTCAGA
CGCGCGCAGTCGTTGATACTCTAGACCAGGGAAAACGAAAGCCGGTCAGCGGGCACTCTTCCGTGGTCTGGTGAATA
GATCGCAAGGGTATCATGGCGAGGGCCTCGGTTCGAGCCCGGGTCCGGGCCGGACGGTCCGCCATGATCCACGCG
GTTACCGCCCGCGTGTCGAACCCAGGTGTGCGACGTCAGACAACGGTGGAGTGTTCCTTTTGGCGTTTTTCTGGCCG
GGCGCCGGCGCCGCGTAAGAGACTAAGCCGCGAAAGCGAAAGCAGTAAGTGGCTCGCTCCCCGTAGCCGGAGGGATC
CTTGCTAAGGGTTGCGTTGCGGCGAACCCCGTTCGAATCCCGTACTCGGGCCGGACCCCGCGGCTAAGGTGTT
GGATTGGCCTCCCCCTCGTATAAAGACCCCGCTTGCGGATTGACTCCGGACACGGGGACGGAGCCCCTTTTATTTTTG
CTTTCCCCAGATGCATCCGGTGCTGCGGCAGATGCGCCCCCGCCCCAGCAGCAGCAACAACACCAGCAAGAGCGGC
AGCAACAGCAGCGGGAGTCATGCAGGGCCCCTCACCCACCCTCGGCGGGCCGGCCACCTCGGCGTCCGCGGCCGTG
TCTGGCGCCTGCGGCGGCGGCGGGGGGCCGGCTGACGACCCCGAGGAGCCCCCGCGGCGCAGGGCCAGACACTACCT
GGACCTGGAGGAGGGCGAGGGCCTGGCGCGGCTGGGGGCGCCGTCTCCCGAGCGCCACCCGCGGGTGCAGCTGAAGC
GCGACTCGCGCGAGGCGTACGTGCCTCGGCAGAACCTGTTCAGGGACCGCGCGGGCGAGGAGCCCGAGGAGATGCGG
```

DESCRIPTION OF THE SEQUENCES

```
GACAGGAGGTTCAGCGCAGGGCGGGAGCTGCGGCAGGGGCTGAACCGCGAGCGGCTGCTGCGCGAGGAGGACTTTGA
GCCCGACGCGCGGACGGGGATCAGCCCCGCGCGCGCACGTGGCGGCCGCCGACCTGGTGACGGCGTACGAGCAGA
CGGTGAACCAGGAGATCAACTTCCAAAAGAGTTTCAACAACCACGTGCGCACGCTGGTGGCGCGCGAGGAGGTGACC
ATCGGGCTGATGCACCTGTGGGACTTTGTAAGCGCGCTGGTGCAGAACCCCAACAGCAAGCCTCTGACGGCGCAGCT
GTTCCTGATAGTGCAGCACAGCAGGGACAACGAGGCGTTTAGGGACGCGCTGCTGAACATCACCGAGCCCGAGGGTC
GGTGGCTGCTGGACCTGATTAACATCCTGCAGAGCATAGTGGTGCAGGAGCGCAGCCTGAGCCTGGCCGACAAGGTG
GCGGCCATCAACTACTCGATGCTGAGCCTGGGCAAGTTTTACGCGCGCAAGATCTACCAGACGCCGTACGTGCCCAT
AGACAAGGAGGTGAAGATCGACGGTTTTTACATGCGCATGGCGCTGAAGGTGCTCACCCTGAGCGACGACCTGGGCG
TGTACCGCAACGAGCGCATCCACAAGGCCGTGAGCGTGAGCCGGCGGCGCGAGCTGAGCGACCGCGAGCTGATGCAC
AGCCTGCAGCGGGCGCTGGCGGGCGCCGGCAGCGGCGACAGGGAGGCGGAGTCCTACTTCGATGCGGGGCGGACCT
GCGCTGGGCGCCCAGCCGGCGGGCCCTGGAGGCGCGGGGGTCCGCGAGGACTATGACGAGGACGGCGAGGAGGATG
AGGAGTACGAGCTAGAGGAGGGCGAGTACCTGGACTAAACCGCGGGTGGTGTTTCCGGTAGATGCAAGACCCGAACG
TGGTGGACCCGGCGCTGCGGGCGGCTCTGCAGAGCCAGCCGTCCGGCCTTAACTCCTCAGACGACTGGCGACAGGTC
ATGGACCGCATCATGTCGCTGACGGCGCGTAACCCGGACGCGTTCCGGCAGCAGCCGCAGGCCAACAGGCTCTCCGC
CATCCTGGAGGCGGTGGTGCCTGCGCGCTCGAACCCCACGCACGAGAAGGTGCTGGCCATAGTGAACGCGCTGGCCG
AGAACAGGGCCATCCGCCCGGACGAGGCCGGGCTGGTGTACGACGCGCTGCTGCAGCGCGTGGCCCGCTACAACAGC
GGCAACGTGCAGACCAACCTGGACCGGCTGGTGGGGGACGTGCGCGAGGCGGTGGCGCAGCGCGAGCGCGCGGATCG
GCAGGGCAACCTGGGCTCCATGGTGGCGCTGAATGCCTTCCTGAGCACGCAGCCGGCCAACGTGCCGCGGGGGCAGG
AAGACTACACCAACTTTGTGAGCGCGCTGCGGCTGATGGTGACCGAGACCCCCAGAGCGAGGTGTACCAGTCGGGC
CCGGACTACTTCTTCCAGACCAGCAGACAGGGCCTGCAGACGGTGAACCTGAACCAGGCTTTCAAGAACCTGCGGGG
GCTGTGGGGCGTGAAGGCGCCCACCGGCGACCGGGCGACGGTGTCCAGCCTGCTGACGCCCAACTCGCGCCTGCTGC
TGCTGCTGATCGCGCCGTTCACGGACAGCGGCAGCGTGTCCGGGACACCTACCTGGGGCACCTGCTGACCCTGTAC
CGCGAGGCCATCGGGCAGGCGCAGGTGGACGAGCACACCTTCCAGGAGATCACCAGCGTGAGCCGCGCGCTGGGGCA
GGAGGACACGAGCAGCCTGGAGGCGACTCTGAACTACCTGCTGACCAACCGGCGGCAGAAGATTCCCTCGCTGCACA
GCCTGACCTCCGAGGAGGAGCGCATCTTGCGCTACGTGCAGCAGAGCGTGAGCCTGAACCTGATGCGCGACGGGGTG
ACGCCCAGCGTGGCGCTGGACATGACCGCGCGCAACATGGAACCGGCATGTACGCCGCGCACCGGCCTTACATCAA
CCGCCTGATGGACTACCTGCATCGCGCGGCGGCCGTGAACCCCGAGTACTTTACCAACGCCATCCTGAACCCGCACT
GGCTCCCGCCGCCCGGGTTCTACAGCGGGGGCTTCGAGGTCCCGGAGACCAACGATGGCTTCCTGTGGGACGACATG
GACGACAGCGTGTTCTCCCCGCGGCCGCAGGCGCTGGCGGAAGCGTCCCTGCTGCGTCCCAAGAAGGAGGAGGAGGA
GGAGGCGAGTCGCCGCCGCGGCAGCAGCGGCGTGGCTTCTCTGTCCGAGCTGGGGGCGGCAGCCGCCGCGCGCCCCG
GGTCCCTGGGCGGCAGCCCCTTTCCGAGCCTGGTGGGGTCTCTGCACAGCGAGCGCACCACCCGCCCTCGGCTGCTG
GGCGAGGACGAGTACCTGAATAACTCCCTGCTGCAGCCGGTGCGGGAGAAAAACCTGCCTCCCGCCTTCCCCAACAA
CGGGATAGAGAGCCTGGTGGACAAGATGAGCAGATGGAAGACCTATGCGCAGGAGCACAGGGACGCGCCTGCGCTCC
GGCCGCCCACGCGGCGCCAGCGCCACGACCGGCAGCGGGGGCTGGTGTGGGATGACGAGGACTCCGCGGACGATAGC
AGCGTGCTGGACCTGGGAGGGAGCGGCAACCCGTTCGCGCACCTGCCCCCCGCCTGGGAGGATGTTTTAAAAAAA
AAAAAAAAAAGCAAGAAGCATGATGCAAAAATTAAATAAAACTCACCAAGGCCATGGCGACCGAGCGTTGGTTTCTT
GTGTTCCCTTCAGTATGCGGCGCGCGGCGATGTACCAGGAGGGACCTCCTCCCTCTTACGAGAGCGTGGTGGGCGCG
GCGGCGGCGGCGCCCTCTTCTCCCTTTGCGTCGCAGCTGCTGGAGCCGCCGTACGTGCCTCCGCGCTACCTGCGGCC
TACGGGGGGGAGAAACAGCATCCGTTACTCGGAGCTGGCGCCCCTGTTCGACACCACCGGGTGTACCTGGTGGACA
ACAAGTCGGCGGACGTGGCCTCCCTGAACTACCAGAACGACCACACGCAATTTTTTGACCACGGTCATCCAGAACAAT
GACTACAGCCCGAGCGAGGCCAGCACCCAGACCATCAATCTGGATGACCGGTCGCACTGGGGCGGCGACCTGAAAAC
CATCCTGCACACCAACATGCCCAACGTGAACGAGTTCATGTTCACCAATAAGTTCAAGGCGCGGGTGATGGTGTCGC
GCTCGCACACCAAGGAAGACCGGGTGGAGCTGAAGTACGAGTGGGTGGAGTTCGAGCTGCCAGAGGGCAACTACTCC
GAGACCATGACCATTGACCTGATGAACAACGCGATCGTGGAGCACTATCTGAAAGTGGGCAGGCAGAACGGGGTCCT
GGAGAGCAGCATCGGGGTCAAGTTCGACACCAGGAACTTCCGCCTGGGGCTGGACCCCGGTGACCGGGCTGGTTATGC
CCGGGGTGTACACCAACGAGGCCTTCCATCCCGACATCATCCTGCTGCCCGGCTGCGGGGTGGACTTCACTTACAGC
CGCCTGAGCAACCTCCTGGGCATCCGCAAGCGGCAGCCCTTCCAGGAGGGCTTCAGGATCACCTACGAGGACCTGGA
GGGGGGCAACATCCCCGCGCTCCTCGATGTGGAGGCCTACCAGGATAGCTTGAAGGAAAATGAGGCGGGACAGGAGG
ATACCGCCCCGCCGCCTCCGCCGCCGCGAGCAGGGCAGGGTGAGGATGCTGCTGACACCGCGCCGCGGACGGGCAGAG
GCCGACCCCGCTATGGTGGTGGAGGCTCCCGAGCAGGAGGAGGACATGAATGACAGTGCGGTGCGCGGAGACACCTT
CGTCACCCGGGGGGAGGAAAAGCAAGCGGAGGCCGAGGCCGCGGCCGAGGAAAAGCAACTGGCGGCAGCAGCGGCGG
CGGCGGCGTTGGCCGCGGCGGAGGCTGAGTCTGAGGGGACCAAGCCCGCCAAGGAGCCCGTGATTAAGCCCCTGACC
GAAGATAGCAAGAAGCGCAGTTACAACCTGCTCAAGGACAGCACCAACAACGCGTACCGCAGCTGGTACCTGGCCTA
CAACTACGGCGACCCGTCGACGGGGGTGCGCTCCTGGACCCTGCTGTGCACGCCGGACGTGACCTGCGCGTCGGAGC
AGGTGTACTGGTCGCTGCCCGACATGATGCAAGACCCCGTGACCTTCCGCTCCACGCGGCAGGTCAGCAACTTCCCG
GTGGTGGGCGCCGAGCTGCTGCCCGTGCACTCCAAGAGCTTCTACAACGACCAGGCCGTCTACTCCCAGCTCATCCG
CCAGTTCACCTCTCTGACCCACGTGTTCAATCGCTTTCCTGAGAACCAGATTCTGGCGCGCCCGCCCGCCCCCACCA
TCACCACCGTCAGTGAAAACGTTCCTGCTCTCACAGATCACGGGACGTACCGCTGCGCAACAGCATCGGAGGAGTC
CAGCGAGTGACCGTTACTGACGCCAGACGCCGCACCTGCCCCTACGTTTACAAGGCCTTGGGCATAGTCTCGCCGCG
CGTCCTTTCCAGCCGCACTTTTTGAGCAACACCACCATCATGTCCATCCTGATCTCACCCAGCAATAACTCCGGCTG
GGGACTGCTGCGCGCGCCCAGCAAGATGTTCGGAGGGGCGAGGAAGCGTTCCGAGCAGCACCCCGTGCGCGTGCGCG
GCACTTCCGCGCCCCTGGGGAGCGCACAAACGCGGCCGCGCGGGGCGCACCACCGTGGACGACGCCATCGACTCG
GTGGTGGAGCAGGCGCGCAACTACAGGCCCGCGGTCTCTACCGTGGACGCGGCCATCCAGACCGTGGTCGGGGCGC
GCGGCGGTACGCCAAGCTGAAGAGCCGCCGGAAGCGCGTGGCCCGCCGCCACCGCCGCCGACCCGGGGCCGCCGCCA
AACGCGCCGCCGCGGCCCTGCTTCGCCGGGCCAAGCGCACGGGCCGCCGCGCCGCCATGAGGGCCGCGCGCCGCTTG
GCCGCCGGCATCACCGCCGCCACCATGGCCCCGCGTACCCGAAGACGCCGCCGCCGCCGCCGCCCATCAG
TGACATGGCCAGCAGGCGCCGGGGCAACGTGTACTGGGTGCGCGACTCGGTGACCGGCACGCGCGTGCCCGTGCGCT
TCCGCCCCCCGCGGACTTGAGATGATGTGAAAAAACAACACTGAGTCTCCTGCTGTTGTGTATCCCAGCGGCGGC
GGCGCGCGCAGCGTCATGTCCAAGCGCAAAATCAAAGAAGAGATGCTCCAGGTCGTCGCGCCGGAGATCTATGGGCC
CCCGAAGAAGGAAGAGCAGGATTCGAAGCCCCGCAAGATAAAGCGGGTCAAAAAGAAAAAGAAAGATGATGACGATG
CCGATGGGAGGTGGAGTTCCTGCGCGCCACGGCGCCCAGGCGCCCAGGCGTCGTGAGTGGAAGGGCCGGCGCGTAAAGCGC
GTCCTGCGCCCCGGCACCGCGGTGGTCTTCACGCCCGGCGAGCGCTCCACCCGGACTTTCAAGCGCGTCTATGACGA
GGTGTACGGCGACGAAGACCTGCTGGAGCAGGCCAACGAGCGCTTCGGAGAGTTTGCTTACGGGAAGCGTCAGCGGG
CGCTGGGGAAGGAGGACCTGCTGGCGCTGCCGCTGGACCAGGGCAACCCCACCCCCAGTCTGAAGCCCGTGACCCTG
CAGCAGGTGCTGCCGAGCAGCGCACCCTCCGAGGCGAAGCGGGTCTGAAGCGCGAGGGCGGCGACCTGGCGCCCAC
CGTGCAGCTCATGGTGCCCAAGCGGCAGAGGCTGGAGGATGTGCTGGAGAAAATGAAAGTAGACCCCGGTCTGCAGC
CGGACATCAGGGTCCGCCCCATCAAGCAGGTGGCGCCGGGCCTCGGCGTGCAGACCGTGGACGTGGTCATCCCCACC
```

-continued

DESCRIPTION OF THE SEQUENCES

```
GGCAACTCCCCCGCCGCCGCCACCACTACCGCTGCCTCCACGGACATGGAGACACAGACCGATCCCGCCGCAGCCGC
AGCCGCAGCCGCCGCCGCGACCTCCTCGGCGGAGGTGCAGACGGACCCCTGGCTGCCGCCGGCGATGTCAGCTCCCC
GCGCGCGTCGCGGGCGCAGGAAGTACGGCGCCGCCAACGCGCTCCTGCCCGAGTACGCCTTGCATCCTTCCATCGCG
CCCACCCCCGGCTACCGAGGCTATACCTACCGCCCGCGAAGAGCCAAGGGTTCCACCCGCCGTCCCCGCCGACGCGC
CGCCGCCACCACCCGCCGCCGCCGCCGCAGACGCCAGCCCGCACTGGCTCCAGTCTCCGTGAGGAAAGTGGCGCGCG
ACGGACACACCCTGGTGCTGCCCAGGGCGCGCTACCACCCCAGCATCGTTTAAAAGCCTGTTGTGGTTCTTGCAGAT
ATGGCCCTCACTTGCCGCCTCCGTTTCCCGGTGCCGGGATACCGAGGAGGAAGATCGCGCCGCAGGAGGGGTCTGGC
CGGCCGCGGCCTGAGCGGAGGCAGCCGCCGCGCGCACCGGCGGCGACGCGCCACCAGCCGACGCATGCGCGGCGGGG
TGCTGCCCCTGTTAATCCCCTGATCGCCGCGGCGATCGGCGCCGTGCCCGGGATCGCCTCCGTGGCCTTGCAAGCG
TCCCAGAGGCATTGACAGACTTGCAAACTTGCAAATATGGAAAAAAAAACCCCAATAAAAAAGTCTAGACTCTCACG
CTCGCTTGGTCCTGTGACTATTTTGTAGAATGGAAGACATCAACTTTGCGTCGCTGGCCCCGCGTCACGGCTCGCGC
CCGTTCCTGGGACACTGGAACGATATCGGCACCAGCAACATGAGCGGTGGCGCCTTCAGTTGGGGCTCTCTGTGGAG
CGGCATTAAAAGTATCGGGTCTGCCGTTAAAAATTACGGCTCCCGGGCCTGGAACAGCAGCACGGGCCAGATGTTGA
GAGACAAGTTGAAAGAGCAGAACTTCCAGCAGAAGGTGGTGGAGGGCCTGGCCTCCGGCATCAACGGGGTGGTGGAC
CTGGCCAACCAGGCCGTGCAGAATAAGATCAACAGCAGACTGGACCCCCGGCCGCCGGTGGAGGGAGGGTGCCGCCGGC
GCTGGAGACGGTGTCCCCCGATGGGCGTGGCGAGAAGCGCCCGCGGCCCGATAGGGAAGAGACCACTCTGGTCACGC
AGACCGATGAGCCGCCCCCGTATGAGGAGGCCCTGAAGCAAGGTCTGCCCACCACGCGGCCCATCGCGCCCATGGCC
ACCGGGGTGGTGGGCCGCCACACCCCCGCCACGCTGGACTTGCCTCCGCCCGCCGATGTGCCGCAGCAGCAGAAGGC
GGCACAGCCGGGCCCGCCCGCGACCGCCTCCCGTTCCTCCGCCGGTCCTCTGCGCCGCGCGGCCAGCGGCCCCCGCG
GGGGGGTCGCGAGGCACGGCAACTGGCAGAGCACGCTGAACAGCATCGTGGGTCTGGGGGTGCGGTCCGTGAAGCGC
CGCCGATGCTACTGAATAGCTTAGCTAACGTGTTGTATGTGTGTATGCGCCCTATGTCGCCGCCAGAGGAGCTGCTG
AGTCGCCGCCGTTCGCGCGCCCACCACCACCGCCACTCCGCCCCTCAAGATGGCGACCCCATCGATGATGCCGCAGT
GGTCGTACATGCACATCTCGGGCCAGGACGCCTCGGAGTACCTGAGCCCCGGGCTGGTGCAGTTCGCCCGCGCCACC
GAGAGCTACTTCAGCCTGAGTAACAAGTTTAGGAACCCCACGGTGGCGCCCACGCACGATGTGACCACCGACCGGTC
TCAGCGCCTGACGCTGCGGTTCATTCCCGTGGACCGCGAGGACACCGCGTACTCGTACAAGGCGCGGTTCACCCTGG
CCGTGGGCGACAACCGCGTGCTGGACATGGCCTCCACCTACTTTGACATCCGCGGGGTGCTGGACCGGGGTCCCACT
TTCAAGCCCTACTCTGGCACCGCCTACAACTCCCTGGCCCCCAAGGGCGCTCCCAACTCCTGCGAGTGGGAGCAAGA
GGAAACTCAGGCAGTTGAAGAAGCAGCAGAAGAGGAAGAAGAAGATGCTGACGGTCAAGCTGAGGAAGAGCAAGCAG
CTACCAAAAAGACTCATGTATATGCTCAGGCTCCCCTTTCTGGCGAAAAAATTAGTAAAGATGGTCTGCAAATAGGA
ACGGACGCTACAGCTACAGAACAAAAACCTATTTATGCAGACCCTACATTCCAGCCCGAACCCCAAATCGGGGAGTC
CCAGTGGAATGAGGCAGATGCTACAGTCGCCGGCGGTAGAGTGCTAAAGAAATCTACTCCCATGAAACCATGCTATG
GTTCCTATGCAAGACCCACAAATGCTAATGAGGTCAGGGTGTACTAACGGCAAATGCCCAGGGACAGCTAGAATCT
CAGGTTGAAATGCAATTCTTTTCAACTTCTGAAAACGCCCGTAACGAGGCTAACAACATTCAGCCCAAATTGGTGCT
GTATAGTGAGGATGTGCACATGGAGACCCCGGATACGCACCTTTCTTACAAGCCCGCAAAAAGCGATGACAATTCAA
AAATCATGCTGGGTCAGCAGTCCATGCCCAACAGACCTAATTACATCGGCTTCAGAGACAACTTTATCGGCCTCATG
TATTACAATAGCACTGGCAACATGGGAGTGCTTGCAGGTCAGGCCTCTCAGTTGAATGCAGTGGTGGACTTGCAAGA
CAGAAACACAGAACTGTCCTACCAGCTCTTGCTTGATTCCATGGGTGACAGAACCAGATACTTTTCCATGTGGAATC
AGGCAGTGGACAGTTATGACCCAGATGTTAGAATTATTGAAAATCATGGAACTGAAGACGAGCTCCCCAACTATTGT
TTCCCTCTGGGTGGCATAGGGGTAACTGACACTTACCAGGCTGTTAAAACCAACAATGGCAATAACGGGGGCCAGGT
GACTTGGACAAAAGATGAAACTTTTGCAGATCGCAATGAAATAGGGGTGGGAAACAATTTCGCTATGGAGATCAACC
TCAGTGCCAACCTGTGGAGAAACTTCCTGTACTCCAACGTGGCGCTGTACCTACCAGACAAGCTTAAGTACAACCCC
TCCAATGTGGACATCTCTGACAACCCCAACACCTACGATTACATGAACAAGCGAGTGGTGGCCCCGGGGCTGGTGGA
CTGCTACATCAACCTGGGCGCGCGCTGGTCGCTGGACTACATGGACAACGTCAACCCCTTCAACCACCACCGCAATG
CGGGCCTGCGCTACCGCTCCATGCTCCTGGGCAACGGGCGCTACGTGCCCTTCCACATCCAGGTGCCCCAGAAGTTC
TTTGCCATCAAGAACCTCCTCCTCCTGCCGGGCTCCTACACCTACGAGTGCCTTCAGGAAGGATGTCAACATGGT
CCTCCAGAGCTCTCTGGGTAACGATCTCAGGGTGGACGGGGCCAGCATCAAGTTCGAGAGCATCTGCCTCTACGCCA
CCTTCTTCCCCATGGCCCACAACACGGCCTCCACGCTCGAGGCCATGCTCAGGAACGACACCAACGACCAGTCCTTC
AATGACTACCTCTCCGCCGCCAACATGCTCTACCCCATACCCGCCAACGCCACCAACGTCCCCATCTCCATCCCCTC
GCGCAACTGGGCGGCCTTCCGCGGCTGGGCCTTCACCCGCCTCAAGACCAAGGAGACCCCCTCCCTGGGCTCGGGAT
TCGACCCCTACTACACCTACTCGGGCTCCATTCCCTACCTGGACGGCACCTTCTACCTCAACCCACACTTTCAAGAAG
GTCTCGGTCACCTTCGACTCCTCGGTCAGCTGGCCGGGCAACGACCGTCTGCTCACCCCCAACGAGTTCGAGATCAA
GCGCTCGGTCGACGGGGAGGGCTACAACGTGGCCCAGTGCAACATGACCAAGGACTGGTTCCTGGTCCAGATGCTGG
CCAACTACAACATCGGCTACCAGGGCTTCTACATCCCAGAGAGCTACAAGGACAGGATGTACTCCTTCTTCAGGAAC
TTCCAGCCCATGAGCCGGCAGGTGGTGGACCAGACCAAGTACAAGGACTACCAGGAGGTGGGCATCATCCACCAGCA
CAACAACTCGGGCTTCGTGGGCTACCTCGCCCCCACCATGCGCGAGGGACAGGCTACCCCGCCAACTTCCCCTATC
CGCTCATAGGCAAGACCGCGGTCGACAGCATCACCCAGAAAAAGTTCCTCTGCGACCGCACCCTCTGGCGCATCCCC
TTCTCCAGCAACTTCATGTCCATGGGTGCGCTCTCGGACCTGGGCCAGACTTGCTACGCCAACTCCGCCCACGC
CCTCGACATGACCTTCGAGGTCGACCCCATGGACGAGCCCACCCTTCTCTATGTTCTGTTCGAAGTCTTTGACGTGG
TCCGGGTCCACCAGCCGCACCGCGGCGTCATCGAGACCGTGTACCTGCGTACGCCCTTCTCGGCCGGCAACGCCACC
ACCTAAAGAAGCAAGCCGCAGTCATCGCCGCCTGCATGCCGTCGGGTTCCACCGAGCAAGAGCTCAGGGCCATCGTC
AGAGACCTGGGATGCGGGCCCTATTTTTTGGGCACCTTCGACAAGCGCTTCCTGGCTTTGTCTCCCCACACAAGCT
GGCCTGCGCCATCGTCAACACGGCCGGCCGCGAGACCGGGGGCGTGCACTGGCTGGCCTTCGCCTGGAACCCGCGCT
CCAAAACATGCTTCCTCTTTGACCCCTTCGGCTTTTCGGACCAGCGGCTCAAGCAAATCTACGAGTTCGAGTACGAG
GGCTTGCTGCGTCGCAGCGCCATCGCCTCCTCGCCCGACCGCTGCGTCACCCTCGAAAAGTCCACCCAGACCGTGCA
GGGGCCCGACTCGGCCGCCTGCGGTCTCTTCTGCTGCATGTTTCTGCACGCCTTTGTGCACTGGCCTCAGAGTCCCA
TGGACCGCAACCCCACCATGAACTTGCTGACGGGGGTGCCCAACTCCATGCTCCAGACCCCCAGGTCGAGCCCACC
CTGCGCCGCAACCAGGAGCAGCTACACGCTTCCTGGAGCGCCACTCGCCTTACTTCCGCCGCCACAGCGCACAGAT
CAGGAGGGCCACCTCCTTCTGCCACTTGCAAGAGATGCAAGAAGGGTAATAACGATGTACACACTTTTTTTCTCAAT
AAATGGCATCTTTTTATTTATACAAGCTCTCTGGGGTATTCATTTCCCACCACCACCCGCCGTTGTCGCCATCTGGC
TCTATTTAGAAATCGAAAGGGTTCTGCCGGGAGTCGCCGTGCGCCACGGGCAGGGACACGTTGCGATACTGGTAGCG
GGTGCCCCACTTGAACTCGGGCACCACCAGGCGAGGCAGCAGCCAGCTCGGGGAAGTTTTCGCTCCACAGGCTGCGGGTCAGCA
CCAGCGCGTTCATCAGGTCGGGCGCCGAGATCTTGAAGTCGCAGTTGGGGCGCCGCCCCCTGCGCGCGAGTTGCGG
TACACCGGGTTGCAGCACTGGAACACCAACAGCGCCGGGTGCTTCACGCTGGCCAGCACGCTGCGGTCGGAGATCAG
CTCGGCGTCCAGGTCCTCCGCGTTGCTCAGCGCGAACGGGGTCATCTTGGGCACTTGCCGCCCAGGAAGGGCGCGT
GCCCCGGTTTCGAGTTGCAGTCGCAGCGCAGCGGGATCAGCAGGTGCCCGTGCCCGGACTCGGCGTTGGGGTACAGC
GCGCGCATGAAGGCCTGCATCTGGCGAAAGGCCATCTGGGCCTTGGCGCCCTCCGAGAAGAACATGCCGCAGGACTT
GCCCGAGAACTGGTTTGCGGGGCAGCTGGCGTCGTGCAGGCAGCAGCGCGCGTCGGTGTTGGCGATCTGCACCACGT
```

| DESCRIPTION OF THE SEQUENCES |
|---|
| TGCGCCCCCACCGGTTCTTCACGATCTTGGCCTTGGACGATTGCTCCTTCAGCGCGCGCTGCCCGTTCTCGCTGGTC |
| ACATCCATCTCGATCACATGTTCCTTGTTCACCATGCTGCTGCCGTGCAGACACTTCAGCTCGCCCTCCGTCTCGGT |
| GCAGCGGTGCTGCCACAGCGCGCAGCCCGTGGGCTCGAAAGACTTGTAGGTCACCTCCGCGAAGGACTGCAGGTACC |
| CCTGCAAAAAGCGGCCCATCATGGTCACGAAGGTCTTGTTGCTGCTGAAGGTCAGCTGCAGCCCGCGGTGCTCCTCG |
| TTCAGCCAGGTCTTGCACACGGCCGCCAGCGCCTCCACCTGGTCGGGCAGCATCTTGAAGTTCACCTTCAGCTCATT |
| CTCCACGTGGTACTTGTCCATCAGCGTGCGCGCCGCCTCCATGCCCTTCTCCCAGGCCGACACCAGCGGCAGGCTCA |
| CGGGGTTCTTCACCATCACCGTGGCCGCCGCCTCCGCCGCGCTTTCGCTTTCCGCCCCGCTGTTCTCTTCCTCTTCC |
| TCCTCTTCCTCGCCGCCGCCCACTCGCAGCCCCGCACCACGGGGTCGTCTTCCTGCAGGCGCTGCACCTTGCGCTT |
| GCCGTTGCGCCCTGCTTGATGCGCACGGGCGGGTTGCTGAAGCCCACCATCACCAGCGCGGCCTCTTCTTGCTCGT |
| CCTCGCTGTCCAGAATGACCTCCGGGGAGGGGGGGTTGGTCATCCTCAGTACCGAGGCACGCTTCTTTTTCTTCCTG |
| GGGGCGTTCGCCAGCTCCGCGGCTGCGGCCGCTGCCGAGGTCGAAGGCCGAGGGCTGGGCGTGCGCGGCACCAGCGC |
| GTCCTGCGAGCCGTCCTCGTCCTCCTCGGACTCGAGACGGAGGCGGGCCCGCTTCTTCGGGGGCGCGCGGGGCGGCG |
| GAGGCGGCGGCGGCGACGGAGACGGGGACGAGACATCGTCCAGGGTGGGTGGACGGCGGGCCGCGCCGCGTCCGCGC |
| TCGGGGGTGGTCTCGCGCTGGTCCTCTTCCCGACTGGCCATCTCCCACTGCTCCTTCTCCTATAGGCAGAAAGAGAT |
| CATGGAGTCTCTCATGCGAGTCGAGAAGGAGGAGGACAGCCTAACCGCCCCCTCTGAGCCCTCCACCACCGCCGCCA |
| CCACCGCCAATGCCGCCGCGGACGACGCGCCCACCGAGACCACCGCCAGTACCACCCTCCCCAGCGACGCACCCCCG |
| CTCGAGAATGAAGTGCTGATCGAGCAGGACCCGGGTTTTGTGAGCGGAGAGGAGGATGAGGTGGATGAGAAGGAGAA |
| GGAGGAGGTCGCCGCCTCAGTGCCAAAAGAGGATAAAAAGCAAGACCAGGACGACGCAGATAAGGATGAGACAGCAG |
| TCGGGCGGGGGAACGGAAGCCATGATGCTGATGACGGCTACCTAGACGTGGGAGACGACGTGCTGCTTAAGCACCTG |
| CACCGCCAGTGCGTCATCGTCTGCGACGGCGTGCAGGAGCGCTGCGAAGTGCCCCTGGACGTGGCGGAGGTCAGCCG |
| CGCCTACGAGCGGCACCTCTTCGCGCCGCACGTGCCCCCCAAGCGCCGGGAGAACGCACCTGCGAGCCCAACCCGC |
| GTCTCAACTTCTACCCGGTCTTCGCGGTACCCGAGGTGCTGGCCACCTACCACATCTTTTTCCAAAACTGCAAGATC |
| CCCCTCTCCTGCCGCGCCAACCGCACCCGCGCCGACAAAACCCTGACCCTGCGGCAGGGCGCCCACATACCTGATAT |
| CGCCTCTCTGGAGGAAGTGCCCAAGATCTTCGAGGGTCTCGGTCGCGACGAGAACGGGCGGCGAACGCTCTGCACG |
| GAGACAGCGAAAACGAGAGTCACTCGGGGGTGCTGGTGGAGCTCGAGGGCGACAACGCCGCCTGGCCGTACTCAAG |
| CGCAGCATAGAGGTCACCCACTTTGCCTACCCGGCGCTCAACCTGCCCCCCAAGGTCATGAGTGTGGTCATGGGCGA |
| GCTCATCATGCGCCGCGCCCAGCCCCTGGCCGCGGATGCAAACTTGCAAGAGTCCTCCGAGGAAGGCCTGCCCGCGG |
| TCAGCGACGAGCAGCTGGCGCGCTGGCTGGAGAACCCGCGACCCCGCGCAGCTGGAGGAGCGGCGCAAGCTCATGATG |
| GCCGCGGTGCTGGTCACCGTGGAGCTCGAGTGTCTGCAGCGCTTCTTCGCGGACCCCGAGATGCAGCGCAAGCTCGA |
| GGGAGACCCTGCACTACACCTTCCGCCAGGGCTACGTGCGCCAGGCCTGCAAGATCTCCAACGTGGAGCTCTGCAACC |
| TGGTCTCCTACCTGGGCATCCTGCACGAGAACCGCCTCGGGCAGAACGTCCTGCACTCCACCCTCAAAGGGGAGGCG |
| CGCCGCGACTACATCCGCGACTGCGCCTACCTCTTCCTCTGCTACACCTGGCAGACGGCCATGGGGGTCTGGCAGCA |
| GTGCCTGGAGGAGCGCAACCTCAAGGAGCTGGAAAAGCTCCTCAAGCGCACCCTCAGGGACCTCTGGACGGGCTTCA |
| ACGAGCGCTCGGTGGCCGCCGCGCTGGCGGACATCATCTTTCCCGAGCGCCTGCTCAAGACCCTGCAGCAGGGCCTG |
| CCCGACTTCACCAGCCAGAGCATGCTGCAGAACTTCAGGACTTTCATCCTGGAGCGCTCGGGCATCCTGCCGGCCAC |
| TTGCTGCGCGCTGCCCAGCGACTTCGTGCCCATCAAGTACAGGGAGTGCCCGCCGCCGCTCTGGGGCCACTGCTACC |
| TCTTCCAGCTGGCCAACTACCTCGCCTACCACTCGGACCTCATGGAAGACGTGAGCGGCGAGGGCCTGCTCGAGTGC |
| CACTGCCGCTGCAACCTCTGCACGCCCCACCGCTCTCTAGTCTGCAACCCGCAGCTGCTCAGCGAGAGTCAGATTAT |
| CGGTACCTTCGAGCTGCAGGGTCCCTCGCCTGACGAGAAGTCCGCGGCTCCAGGGCTGAAACTCACTCCGGGGCTGT |
| GGACTTCCGCCTACCTACGCAAATTTGTACCTGAGGACTACCACGCCCACGAGATCAGGTTCTACGAAGACCAATCC |
| CGCCCGCCAAGGCGGAGCTCACCGCCTGCGTCATCACCCAGGGGCACATCCTGGCCCAATTGCAAGCCATCAACAA |
| AGCCCGCCGAGAGTTCTTGCTGAAAAAGGGTCGGGGGGTGTACCTGGACCCCCAGTCCGGCGAGGAGCTAAACCCGC |
| TACCCCCGCCGCCGCCCCAGCAGCGGGACCTTGCTTCCCAGGATGGCACCCAGAAAGAAGCAGCAGCCGCCGCCGCC |
| GCCGCAGCCCATACATGCTTCTGGAGGAAGAGGAGGAGGACTGGGACAGTCAGGCAGAGGAGGTTTCGGACGAGGAGC |
| AGGAGGAGATGATGGAAGACTGGGAGGAGGACAGCAGCCTAGACGAGGAAGCTTCAGAGGCCGAGGAGGTGGCAGAC |
| GCAACACCATCGCCCTCGGTCGCAGCCCCCTCGCCGGGGCCCCTGAAATCCTCCGAACCCAGCACCAGCGCTATAAC |
| CTCCGCTCCTCCGGCGCCGGCGCCACCCGCCCGCAGACCCAACCGTAGATGGGACACCACAGGAACCGGGGTCGGTA |
| AGTCCAAGTGCCCGCCGCCGCCACCGCAGCAGCAGCAGCAGCAGCGCCAGGGCTACCGCTCGTGGCGCGGGCACAAG |
| AACGCCATAGTCGCCTGCTTGCAAGACTGCGGGGGCAACATCTCTTTCGCCCGCCGCTTCCTGCTATTCCACCACG |
| GGTCGCCTTTCCCCGCAATGTCCTGCATTACTACCGTCATCTCTACAGCCCCTACTGCAGCGGCGACCCAGAGGCGG |
| CAGCGGCAGCCACAGCGGCGACCACCACCTAGGAAGATATCCTCCGCGGGCAAGACAGCGGCAGCAGCGGCCAGGAG |
| ACCCGCGGCAGCAGCGGCGGGAGCGGTGGGCGCACTGCGCCTCTCGCCCAACGAACCCCTCTCGACCCGGGAGCTCA |
| GACACAGGATCTTCCCCACTTTGTATGCCATCTTCCAACAGACGCAGAGGCCAGGAGCAGGAGCTGAAAATAAAAAC |
| AGATCTCTGCGCTCCCTCACCCGCAGCTGTCTGTATCACAAAAGCGAAGATCAGCTTCGGCGCACGCTGGAGGACGC |
| GGAGGCACTCTTCAGCAAATACTGCGCGCTCACTCTTAAAGACTAGCTCCGCGCCCTTCTCGAATTTAGGCGGGAGA |
| AAACTACGTCATCGCCGGCCGCCGCCCAGCCCGCCCAGCCGAGATGAGCAAAGAGATTCCCACGCCATACATGTGGA |
| GCTACCAGCCGCAGATGGGACTCGCGGCGGAGCGGCCAGGACTACTCCACCCGCATGAACTACATGAGCGCGGGA |
| CCCCACATGATCTCACAGGTCAACGGGATCCGCGCCCAGCGAAACCAAATACTGCTGGAACAGGCGGCCATCACCGC |
| CACGCCCCGCCATAATCTCAACCCCCGAAATTGGCCCGCCGCCCTCGTGTACCAGGAAACCCCTCCGCCACCACCG |
| TACTACTTCCGCGTGACGCCCAGGCCGAAGTCCAGATGACTAACTCAGGGGCGCAGCTCGCGGGCGGCTTTCGTCAC |
| GGGGCGCGGCCGGCTCCGACCAGGTATAAGACACCTGATGATCAGAGGCCAGGTATCCAGCTCAACGACGAGTCGGT |
| GAGCTCTTCGCTCGGTCTCCGTCCGGACGGAACTTTCCAGCTCGCCGGATCCGGCCGCTCTTCGTTCACGCCCCGCC |
| AGGCGTACCTGACTCTGCAGACCTCGTCCTCGGAGCCCCGCTCCGCGGCATCGGAACCCTCCAGTTCGTGGAGGAG |
| TTCGTGCCCTCGGTCTACTTCAACCCCTTCTCGGGACCTCCCGGACGCTACCCCGACCAGTTCATTCCGAACTTTGA |
| CGCGGTGAAGGACTCGGCGGACGGCTACGACTGAATGTCAGGTGTCGAGGCAGAGCAGCTTCGCCTGAGACACCTCG |
| AGCACTGCCGCCGCCACAAGTGCTTCGCCCGCGGTTCTGGTGAGTTCTGCTACTTTCAGCTACCCCGAGGAGCATACC |
| GAGGGGCCGGCGCACGCGTCCGCCTGACCACCCAGGGCGAGGTTACCTGTTCCCTCATCCGGGAGTTTACCCTCCG |
| TCCCCTGCTAGTGGAGCGGGAGCGGGGTCCCTGTGTCCTAACTATCGCCTGCAACTGCCCTAACCCTGGATTACATC |
| AAGATCTTTGCTGTCATCTCTGTGCTGAGTTTAATAAACGCTGAGATCAGAATCTACTGGGGCTCCTGTCGCCATCC |
| TGTGAACGCCACCGTCTTCACCCACCCCGACCAGGCCCAGGCGAACCTCACCTGCGGTCTGCATCGGAGGGCCAAGA |
| AGTACCTCACCTGGTACTTCAACGGCACCCCTTTGTGGTTTACAACAGCTTCGACGGGGACGGAGTCTCCCTGAAA |
| GACCAGCTCTCCGGTCTCAGCTACTCCATCCACAAGAACACCACCCTCCAACTCTTCCCTCCCTACCTGCCGGGAAC |
| CTACGAGTGCGTCACCGGCCGCTGCACCCACCTCACCCGCCTGATCGTAAACCAGAGCTTTCCGGGAACAGATAACT |
| CCCTCTTCCCCAGAACAGGAGGTGAGCTCAGGAAACTCCCCGGGGACCAGGGCGGAGACGTACCTTCGACCCTTGTG |
| GGGTTAGGATTTTTTATTACCGGGTTGCTGGCTCTTTTAATCAAAGTTTCCTTGAGATTTGTTCTTTCCTTCTACGT |
| GTATGAACACCTCAACCTCCAATAACTCTACCCTTTCTTCGGAATCAGGTGACTTCTCTGAAATCGGGCTTGGTGTG |
| CTGCTTACTCTGTTGATTTTTTCCTTATCATACTCAGCCTTCTGTGCCTCAGGCTCGCCGCCTGCTGCACACAT |

| DESCRIPTION OF THE SEQUENCES |
|---|
| CTATATCTACTGCTGGTTGCTCAAGTGCAGGGGTCGCCACCCAAGATGAACAGGTACATGGTCCTATCGATCCTAGG |
| CCTGCTGGCCCTGGCGGCCTGCAGCGCCGCCAAAAAAGAGATTACCTTTGAGGAGCCCGCTTGCAATGTAACTTTCA |
| AGCCCGAGGGTGACCAATGCACCACCCTCGTCAAATGCGTTACCAATCATGAGAGGCTGCGCATCGACTACAAAAAC |
| AAAACTGGCCAGTTTGCGGTCTATAGTGTGTTTACGCCCGGAGACCCCTCTAACTACTCTGTCACCGTCTTCCAGGG |
| CGGACAGTCTAAGATATTCAATTACACTTTCCCTTTTTATGAGTTATGCGATGCGGTCATGTACATGTCAAAACAGT |
| ACAACCTGTGGCCTCCCTCTCCCAGGCGTGTGTGGAAAATACTGGGTCTTACTGCTGTATGGCTTTCGCAATCACT |
| ACGCTCGCTCTAATCTGCACGGTGCTATACATAAAATTCAGGCAGAGGCGAATCTTTATCGATGAAAAGAAAATGCC |
| TTGATCGCTAACACCGGCTTTCTATCTGCAGAATGAATGCAATCACCTCCCTACTAATCACCACCACCCTCCTTGCG |
| ATTGCCCATGGGTTGACACGAATCGAAGTGCCAGTGGGGTCCAATGTCACCATGGTGGGCCCCGCCGGCAATTCCAC |
| CCTCATGTGGGAAAAATTTGTCCGCAATCAATGGGTTCATTTCTGCTCTAACCGAATCAGTATCAAGCCCAGAGCCA |
| TCTGCGATGGGCAAAATCTAACTCTGATCAATGTGCAAATGATGGATGCTGGGTACTATTACGGGCAGCGGGGAGAA |
| ATCATTAATTACTGGCGACCCCACAAGGACTACATGCTGCATGTAGTCGAGGCACTTCCCACTACCACCCCCACTAC |
| CACCTCTCCCACCACCACCACCACTACTACTACTACTACTACTACTACTACTACCACTACCGCTGCCCGCCATA |
| CCCGCAAAAGCACCATGATTAGCACAAAGCCCCCTCGTGCTCACTCCCACGCCGGCGGGCCCATCGGTGCGACCTCA |
| GAAACCACCGAGCTTTGCTTCTGCCAATGCACTAACGCCAGCGCTCATGAACTGTTCGACCTGGAGAATGAGGATGT |
| CCAGCAGAGCTCCGCTTGCCTGACCCAGGAGGCTGTGGAGCCCGTTGCCCTGAAGCAGATCGGTGATTCAATAATTG |
| ACTCTTCTTCTTTTGCCACTCCCGAATACCCTCCCGATTCTACTTTCCACATCACGGGTACCAAAGACCCTAACCTC |
| TCTTTCTACCTGATGCTGCTGCTCTGTATCTCTGTGGTCTCTTCCGCGCTGATGTTACTGGGGATGTTCTGCTGCCT |
| GATCTGCCGCAGAAAGAGAAAAGCTCGCTCTCAGGGCCAACCACTGATGCCCTTCCCCTACCCCCCGGATTTTGCAG |
| ATAACAAGATATGAGCTCGCTGCTGACACTAACCGCTTTACTAGCCTGCGCTCTAACCCTTGTCGCTTGCGACTCGA |
| GATTCCACAATGTCACAGCTGTGGCAGGAGAAAATGTTACTTTCAACTCCACGGCCGATACCCAGTGGTCGTGGAGT |
| GGCTCAGGTAGCTACTTAACTATCTGCAATAGCTCCACTTCCCCCGGCATATCCCCAACCAAGTACCAATGCAATGC |
| CAGCCTGTTCACCCTCATCAACGCTTCCACCCTGGACAATGGACTCTATGTAGGCTATGTACCCTTTGGTGGGCAAG |
| GAAAGACCCACGCTTACAACCTGGAAGTTCGCCAGCCCAGAACCACTACCCAAGCTTCTCCCACCACCACCACCACC |
| ACCACCATCACCAGCAGCAGCAGCAGCAGCAGCCACAGCAGCAGCAGCAGATTATTGACTTTGGTTTTGGCCAGCTC |
| ATCTGCCGCTACCCAGGCCATCTACAGCTCTGTGCCCGAAACCACTCAGATCCACCGCCCAGAAACGACCACCGCCA |
| CCACCCTACACACCTCCAGCGATCAGATGCCGACCAACATCACCCCCTTGGCTCTTCAAATGGGACTTACAAGCCCC |
| ACTCCAAAACCAGTGGATGCGGCCGAGGTCTCCGCCCTCGTCAATGACTGGGCGGGGCTGGGAATGTGGTGGTTCGC |
| CATAGGCATGATGGCGCTCTGCCTGCTTCTGCTCTGGCTCATCTGCTGCCTCCACCGCAGGCGAGCCAGACCCCCCA |
| TCTATAGACCCATCATTGTCCTGAACCCCGATAATGATGGGATCCATAGATTGGATGGCCTGAAAAACCTACTTTTT |
| TCTTTTACAGTATGATAAATTGAGACATGCCTCGCATTTTCTTGTACATGTTCCTTCTCCCACCTTTTCTGGGGTGT |
| TCTACGCTGGCCGCTGTGTCTCACCTGGAGGTAGACTGCCTCTCACCCTTCACTGTCTACCTGCTTTACGGATTGGT |
| CACCCTCACTCTCATCTGCAGCCTAATCACAGTAATCATCGCCTTCATCCAGTGCATTGATTACATCTGTGTGCGCC |
| TCGCATACTTCAGACACCACCCGCAGTACCGAGACAGGAACATTGCCCAACTTCTAAGACTGCTCTAATCATGCATA |
| AGACTGTGATCTGCCTTCTGATCCTCTGCATCCTGCCCACCCTCACCTCCTGCCAGTACACCACAAAATCTCCGCGC |
| AAAAGACATGCCTCCTGCCGCTTCACCCAACTGTGGAATATACCCAAATGCTACAACGAAAAGAGCGAGCTCTCCGA |
| AGCTTGGCTGTATGGGGTCATCTGTGTCTTAGTTTTCTGCAGCACTGTCTTTGCCCTCATAATCTACCCCTACTTTG |
| ATTTGGGATGGAACGCGATCGATGCCATGAATTACCCCACCTTTCCCGCACCCGAGATAATTCCACTGCGACAAGTT |
| GTACCCGTTGTCGTTAATCAACGCCCCCATCCCCTACGCCCACTGAAATCAGCTACTTTAACCTAACAGGCGGAGA |
| TGACTGACGCCCTAGATCTAGAAATGGACGGCATCAGTACCGAGCAGCGTCTCCTAGAGAGGCGCAGGCAGGCGGCT |
| GAGCAAGAGCGCCTCAATCAGGAGCTCCGAGATCTCGTTAACCTGCACCAGTGCAAAAGAGGCATCTTTTGTCTGGT |
| AAAGCAGGCCAAAGTCACCTACGAGAAGACCGGCAACAGCCACCGCCTCAGTTACAAATTGCCCACCCAGCGCCAGA |
| AGCTGGTGCTCATGGTGGGTGAGAATCCCATCACCGTCACCCAGCACTCGGTAGAGACCGAGGGGTGTCTGCACTCC |
| CCCTGTCGGGGTCCAGAAGACCTCTGCACCCTGGTAAAGACCCTGTGCGGTCTCAGAGATTTAGTCCCCTTTAACTA |
| ATCAAACACTGGAATCAATAAAAAGAATCACTTACTTAAAATCAACAGCAGGTCTCTGTCCAGTTTATTCAGCAGC |
| ACCTCCTTCCCCTCCTCCCAACTCTGGTACTCCAAACGCCTTCTGGCGGCAAACTTCCTCCACACCCTGAAGGGAAT |
| GTCAGATTCTTGCTCCTGTCCCTCCGCACCCACTATCTTCATGTTGTTGCAGATGAAGCGCACCAAAACGTCTGACG |
| AGAGCTTCAACCCCGTGTACCCCTATGACACGGAAAGCGGCCCTCCCTCCGTCCCTTTCCTCACCCCTCCCTTCGTG |
| TCTCCCGATGGATTCCAAGAAAGTCCCCCCGGGGTCCTGTCTCTGAACCTGGCCGGACCCGTTGGTCACTTCCCACG |
| CATGCTCGCCCTGAAAATGGGAAGTGGCCTCTCCCTGGACGACGCTGGCAACCTCACCTCTCAAGATATCACCACCG |
| CTAGCCCTCCCCTCAAAAAAACCAAGACCAACCTCAGCCTAGAAACCTCATCCCCCCTAACTGTGAGCACCTCAGGC |
| GCCCTCACCGTAGCAGCCGCCGCTCCCCTGGCGGTGGCCGGCACCTCCTCACCATGCAATCAGAGGCCCCCCTGAC |
| AGTACAGGATGCAAAACTCACCCTGGCCACCAAAGGCCCCCTGGCGTGTGAAGGCAAACTGGCCTTGCAAACAT |
| CGGCCCCGCTGACGGCCGCTGACAGCAGCACCCTCACAGTCAGTGCCACACCACCCCTTAGCACAAGCAATGGCAGC |
| TTGGGTATTGACATGCAAGCCCCCATTTACACCACCAATGGAAAACTAGGACTTAACTTTGGCGCTCCCCTGCATGT |
| GGTAGACAGCCTAAATGCACTGACTGTAGTTACTGGCCAAGGTCTTACGATAAACGGAACAGCCCTACAAACTAGAG |
| TCTCAGGTGCCCTCAACTATGACACATCAGGAAACCTAGAATTGAGAGCTGCAGGGGGTATGCGAGTTGATGCAAAT |
| GGTCAACTTATCCTTGATGTAGCTTACCCATTTGATGCACAAAACAATCTCAGCCTTAGGCTTGGACAGGGACCCCT |
| GTTTGTTAACTCTGCCCACAACTTGGATGTTAACTACAACAGAGGCCTCTACCTGTTCACATCTGGAAATACCAAA |
| AGCTAGAAGTTAATATCAAAACAGCCAAGGGTCTCATTTATGATGACACTGCTATAGCAATCAATGCGGGTGATGGG |
| CTACAGTTTGACTCAGGCTCAGATACAAATCCATTAAAAACTAAACTTGGATTAGGACTGGATTATGACTCCAGCAG |
| AGCCATAATTGCTAAACTGGGAACTGGCCTAAGCTTTGACAACACAGGTGCCATCACAGTAGGCAACAAAAATGATG |
| ACAAGCTTACCTTGTGGACCACACCAGACCCATCCCCTAACTGTAGAATCATTCAGAGAAAGATGCTAAATTCACA |
| CTTGTTTTGACTAAATGCGGCAGTCAGGTGTTGGCCAGCGTTTCTGTTTTATCTGTAAAAGGTAGCTTGCGCCCAT |
| CAGTGGCACAGTAACTAGTGCTCAGATTGTCCTCAGATTTGATGAAAATGGAGTTCTACTAAGCAATTCTTCCCTTG |
| ACCCTCAATACTGGAACTACAGAAAAGGTGACCTTACAGAGGGCACTGCATATACCAACGCAGTGGGATTTATGCCC |
| AACCTCACAGCATACCCAAAAACACAGAGCCAAACTGCTAAAAGCAACATTGTAAGTCAGGTTTACTTGAATGGGGA |
| CAAATCCAAACCCATGACCCTCACCATTACCCTCAATGGAACTAATGAAACAGGAGATGCCACAGTAAGCACTTACT |
| CCATGTCATTCTCATGGAACTGGAATGGAAGTAATTACATTAATGAAACGTTCCAAACCAACTCCTTCACCTTCTCC |
| TACATCGCCCAAGAATAAAAAGCATGACGCTGTTGATTTGATTCAATGTGTTTCTGTTTTATTTTCAAGCACAACAA |
| AATCATTCAAGTCATTCTTCCATCTTAGCTTAATAGACACAGTAGTGCCAAGCCCCATTC |
| TAGCTTATAGATCAGACAGTGATAATTAACCACCACCACCACCATACCTTTTGATTCAGGAAATCATGATCATCACA |
| GGATCCTAGTCTTCAGGCCGCCCCCTCCCTCCCAAGACACAGAATACACAGTCCTCTCCCCCCGACTGGCTTTAAAT |
| AACACCATCTGGTTGGTCACAGACATGTTCTTAGGGGTTATATTCCACACGGTTCCTGCCGCGCCAGGCGTCGTC |
| GGTGATGTTGATAAACTCTCCCGGCAGCTCGCTCAAGTTCACGTCGCTGTCCAGCGGCTGAACCTCCGGCTGACGCG |
| ATAACTGTGCGACCGGCTGCTGGACGAACGGAGGCCGCGCCTACAAGGGGTAGAGTCATAATCCTCGGTCAGGATA |
| GGGCGGTGATGCAGCAGCAGCGAGCGAAACATCTGCTGCCGCCGCCGCTCCGTCCGGCAGGAAAACAACACGCCGGT |

DESCRIPTION OF THE SEQUENCES

GGTCTCCTCCGCGATAATCCGCACCGCCCGCAGCATCAGCTTCCTCGTTCTCCGCGCGCAGCACCTCACCCTTATCT
CGCTCAAATCGGCGCAGTAGGTACAGCACAGCACCACGATGTTATTCATGATCCCACAGTGCAGGGCGCTGTATCCA
AAGCTCATGCCGGGAACCACCGCCCCCACGTGGCCATCGTACCACAAGCGCACGTAAATCAAGTGTCGACCCCTCAT
GAACGCGCTGGACACAAACATTACTTCCTTGGGCATGTTGTAATTCACCACCTCCCGGTACCAGATAAACCTCTGGT
TGAACAGGGCACCTTCCACCACCATCCTGAACCAAGAGGCCAGAACCTGCCCACCGGCTATGCACTGCAGGGAACCC
GGGTTGGAACAATGACAATGCAGACTCCAAGGCTCGTAACCGTGGATCATCCGGCTGCTGAAGGCATCGATGTTGGC
ACAACACAGACACACGTGCATGCACTTTCTCATGATTAGCAGCTCTTCCCTCGTCAGGATCATATCCCAAGGAATAA
CCCATTCTTGAATCAACGTAAAACCCACACAGCAGGGAAGGCCTCGCACATAACTCACGTTGTGCATGGTCAGCGTG
TTGCATTCCGGAAACAGCGGATGATCCTCCAGTATCGAGGCGCGGGTCTCCTTCTCACAGGGAGGTAAAGGGTCCCT
GCTGTACGGACTGCGCCGGGACGACCGAGATCGTGTTGAGCGTAGTGTCATGGAAAAGGGAACGCCGGACGTGGTCA
TACTTCTTGAAGCAGAACCAGGTTCGCGCGTGGCAGGCCTCCTTGCGTCTGCGGTCTCGCCGTCTAGCTCGCTCCGT
GTGATAGTTGTAGTACAGCCACTCCCGCAGAGCGTCGAGGCGCACCCTGGCTTCCGGATCTATGTAGACTCCGTCTT
GCACCGCGGCCCTGATAATATCCACCACCGTAGAATAAGCAACACCCAGCCAAGCAATACACTCGCTCTGCGAGCGG
CAGACAGGAGGAGCGGGCAGAGATGGGAGAACCATGATAAAAAACTTTTTTTAAAGAATATTTTCCAATTCTTCGAA
AGTAAGATCTATCAAGTGGCAGCGCTCCCCTCCACTGGCGCGGTCAAACTCTACGGCCAAAGCACAGACAACGGCAT
TTCTAAGATGTTCCTTAATGGCGTCCAAAAGACACACCGCTCTCAAGTTGCAGTAAACTATGAATGAAAACCCATCC
GGCTGATTTTCCAATATAGACGCGCCGGCAGCGTCCACCAAACCCAGATAATTTTCTTCTCTCCAGCGGTTTACGAT
CTGTCTAAGCAAATCCCTTATATCAAGTCCGACCATGCCAAAAATCTGCTCAAGAGCGCCCTCCACCTTCATGTACA
AGCAGCGCATCATGATTGCAAAAATTCAGGTTCTTCAGAGACCTGTATAAGATTCAAAATGGGAACATTAACAAAAA
TTCCTCTGTCGCGCAGATCCCTTCGCAGGGCAAGCTGAACATAATCAGACAGGTCCGAACGGACCAGTGAGGCCAAA
TCCCCACCAGGAACCAGATCCAGAGACCCTATACTGATTATGACGCGCATACTCGGGGCTATGCTGACCAGCGTAGC
GCCGATGTAGGCGTGCTGCATGGGCGGCGAGATAAAATGCAAAGTGCTGGTTAAAAAATCAGGCAAAGCCTCGCGCA
AAAAAGCTAACACATCATAATCATGCTCATGCAGGTAGTTGCAGGTAAGCTCAGGAACCAAAACGGAATAACACACG
ATTTTCCTCTCAAACATGACTTCGCGGATACTGCGTAAAACAAAAAATTATAAAAAATTAATTAAATAACTTA
AACATTGGAAGCCTGTCTCACAACAGGAAAAACCACTTTAATCAACATAAGACGGGCCACGGGCATGCCGGCATAGC
CGTAAAAAAATTGGTCCCCGTGATTAACAAGTACCACAGACAGCTCCCCGGTCATGTCGGGGGTCATCATGTGAGAC
TCTGTATACACGTCTGGATTGTGAACATCAGACAAACAAAGAAATCGAGCCACGTAGCCCGGAGGTATAATCACCCG
CAGGCGGAGGTACAGCAAAACGACCCCCATAGGAGGAATCACAAAATTAGTAGGAGAAAAAAATACATAAACACCAG
AAAAACCCTGTTGCTGAGGCAAAATAGCGCCCTCCCGATCCAAAACAACATAAAGCGCTTCCACAGGAGCAGCCATA
ACAAAGACCCGAGTCTTACCAGTAAAAGAAAAAAGATCTCTCAACGCAGCACCAGCACCAACACTTCGCAGTGTAAA
AGGCCAAGTGCCGAGAGAGTATATATAGGAATAAAAAGTGACGTAAACGGGCAAAGTCCAAAAAACGCCCAGAAAAA
CCGCACGCGAACCTACGCCCCGAAACGAAAGCCAAAAAACACTAGACACTCCCTTCCGGCGTCAACTTCCGCTTTCC
CACGCTACGTCACTTCCCCCGGTCAAACAAACTACATATCCGAACTTCCAAGTCGCCACGCCCAAAACACCGCCTA
CACCTCCCCGCCCGCCGGCCCGCCCCCGGACCCGCCTCCCGCCCCGCCGCCCATCTCATTATCATATTGGCTTCA
ATCCAAAATAAGGTATATTATTGATGATG

SEQ ID NO: 2 Polynucleotide sequence encoding the CASI promoter
GGAGTTCCGCGTTACATAACTTACGGTAAATGGCCCGCCTGGCTGACCGCCCAACGACCCCCGCCCATTGACGTCAA
TAATGACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTCAATGACGGTAAATGGCCCGC
CTGGCATTATGCCCAGTACATGACCTTATGGGACTTTCCTACTTGGCAGTACATCTACGTATTAGTCATCGCTATTA
CCATGGTCGAGGTGAGCCCCACGTTCTGCTTCACTCTCCCCATCTCCCCCCCCTCCCCACCCCCAATTTTGTATTTA
TTTATTTTTTAATTATTTTGTGCAGCGATGGGGGCGGGGGGGGGGGGGCGCGCGCCAGGCGGGCGGGGCGGGGC
GAGGGGCGGGGCGGGCGAGGCGGAGAGGTGCGGCGGCAGCCAATCAGAGCGGCGCGCTCCGAAAGTTTCCTTTTAT
GGCGAGGCGGCGGCGGCGGCCTATAAAAAGCGAAGCGCTCCCTATCAGTGATAGAGATCTCCCTATCAGTGAT
AGAGATCGTCGACGAGCTCGCGGCGGGCGGGAGTCGCTGCGCGCTGCCTTCGCCCCGTGCCCCGCTCCGCCGCCGCC
TCGCGCCGCCCGCCCCGGCTCTGACTGACCGCGTTACTAAAACAGGTAAGTCCGGCTCCCGCGCGGGTTTTGGCGC
CTCCCGCGGGCGCCCCCCTCCTCACGGCGAGCGCTGCCACGTCAGACGAAGGGCGCAGCGAGCGTCCTGATCCTTCC
GCCCGGACGCTCAGGACAGCGGCCCGCTGCTCATAAGACTCGGCCTTAGAACCCCAGTATCAGCAGAAGGACATTTT
AGGACGGGACTTGGGTGACTCTAGGGCACTGGTTTTCTTTCCAGAGAGCGGAACAGGCGAGGAAAAGTAGTCCCTTC
TCGGCGATTCTGCGGAGGGATCTCCGTGGGGCGGTGAACGCCGATGATGCCTCTACTAACCATGTTCATGTTTTCTT
TTTTTTTCTACAGGTCCTGGGTGACGAACAG SEQ ID NO: 3 Polynucleotide sequence encoding the enhanced hCMV promoter
CCATTGCATACGTTGTATCCATATCATAATATGTACATTTATATTGGCTCATGTCCAACATTACCGCCATGTTG
ACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGAGTATTTACGGTAAACTGC
CCACTTGGCAGTACATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACGTATTAGTCATCGCT
ATTACCATGGTGATGCGGTTTTGGCAGTACATCAATGGGCGTGGATAGCGGTTTGACTCACGGGGATTTCCAAG
TCTCCACCCCATTGACGTCAATGGGAGTTTGTTTTGGCACCAAAATCAACGGGACTTTCCAAAATGTCGTAACA
ACTCCGCCCCATTGACGCAAATGGGCGGTAGGCGTGTACGGTGGGAGGTCTATATAAGCGAAGCGCTCCCTAT
CAGTGATAGAGATCTCCCTATCAGTGATAGAGATCGTCGACGAGCTCGCGGCGGGCGGGAGTCGCTGCGCGCTG
CCTTCGCCCCGTGCCCCGCTCCGCCGCCGCCTCGCGCCGCCCGCCCCGGCTCTGACTGACCGCGTTACTAAAAC
AGGTAAGTCCGGCTCCCGCGCGGGTTTTGGCGCCTCCCGCGGGCGCCCCCCTCCTCACGGCGAGCGCTGCCCAC
GTCAGACGAAGGGCGCAGCGAGCGTCCTGATCCTTCCGCCCGGACGCTCAGGACAGCGGCCCGCTGCTCATAAG
ACTCGGCCTTAGAACCCCAGTATCAGCAGAAGGACATTTTAGGACGGGACTTGGGTGACTCTAGGGCACTGGTT
TTCTTTCCAGAGAGCGGAACAGGCGAGGAAAAGTAGTCCCTTCTCGGCGATTCTGCGGAGGGATCTCCGTGGGG
CGGTGAACGCCGATGATGCCTCTACTAACCATGTTCATGTTTTCTTTTTTTTCTACAGGTCCTGGGTGACGAA
CAG SEQ ID NO: 4 Polynucleotide sequence encoding the hCMV NM2 bghpolyA cassette
CCATTGCATACGTTGTATCCATATCATAATATGTACATTTATATTGGCTCATGTCCAACATTACCGCCATGTTG
ACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGAGTATTTACGGTAAACTGC

| DESCRIPTION OF THE SEQUENCES |
|---|
| CCACTTGGCAGTACATCAAGTGTATCATATGCCAAGTACGCCCCTATTGACGTCAATGACGGTAAATGGCCCG
CCTGGCATTATGCCCAGTACATGACCTTATGGGACTTTCCTACTTGGCAGTACATCTACGTATTAGTCATCGCT
ATTACCATGGTGATGCGGTTTTGGCAGTACATCAATGGGCGTGGATAGCGGTTTGACTCACGGGGATTTCCAAG
TCTCCACCCCATTGACGTCAATGGGAGTTTGTTTTGGCACCAAAATCAACGGGACTTTCCAAAATGTCGTAACA
ACTCCGCCCCATTGACGCAAATGGGCGGTAGGCGTGTACGGTGGGAGGTCTATATAAGCAGAGCTCTCCCTATC
AGTGATAGAGATCTCCCTATCAGTGATAGAGATCGTCGACGAGCTCGTTTAGTGAACCGTCAGATCGCCTGGAG
ACGCCATCCACGCTGTTTTGACCTCCATAGAAGACACCGGGACCGATCCAGCCTCCGCGGCCGGGAACGGTGCA
TTGGAACGCGGATTCCCCGTGCCAAGAGTGA*GATCTTCCGTTTATCTAGGTACCAGATATCGCCACCATGGCCC*
*TGAGCAAAGTGAAACTGAACGATACACTGAACAAGGACCAGCTGCTGTCCAGCAGCAAGTACACCATCCAGCGG*
*AGCACCGGCGACAGCATCGATACCCCCAACTACGACGTGCAGAAGCACATCAACAAGCTGTGCGGCATGCTGCT*
*GATCACAGAGGACGCCAACCACAAGTTCACCGGCCTGATCGGCATGCTGTACGCCATGAGCCGGCTGGGCCGGG*
*AGGACACCATCAAGATCCTGCGGGACGCCGGCTACCACGTGAAGGCCAATGGCGTGGACGTGACCACACACCGG*
*CAGGACATCAACGGCAAAGAAATGAAGTTCGAGGTGCTGACCCTGGCCAGCCTGACCACCGAGATCCAGATCAA*
*TATCGAGATCGAGAGCCGGAAGTCCTACAAGAAAATGCTGAAAGAAATGGGCGAGGTGGCCCCCGAGTACAGAC*
*ACGACAGCCCCGACTGCGGCATGATCATCCTGTGTATCGCCGCCCTGGTGATCACAAAGCTGGCCGCTGGCGAC*
*AGATCTGGCCTGACAGCCGTGATCAGACGGGCCAACAATGTGCTGAAGAACGAGATGAAGCGGTACAAGGGCCT*
*GCTGCCCAAGGACATTGCCAACAGCTTCTACGAGGTGTTCGAGAAGTACCCCCACTTCATCGACGTGTTCGTGC*
*ACTTCGGCATTGCCCAGAGCAGCACCAGAGGCGGCTCCAGAGTGGAGGGCATCTTCGCCGGCCTGTTCATGAAC*
*GCCTACGGCGCTGGCCAGGTGATGCTGAGATGGGGCGTGCTGGCCAAGAGCGTGAAGAACATCATGCTGGGCCA*
*CGCCAGCGTGCAGGCCGAGATGGAACAGGTGGTGGAGGTGTACGAGTACGCCCAGAAGCTGGGCGGAGGATCTGG*
*GGCGGAGGCATGAGCAGACGGAACCCCTGCAAGTTCGAGATCCGGGGCCACTGCCTGAACGGCAAGCGGTGCCA*
*CTTCAGCCACAACTACTTCGAGTGGCCCCCTCATGCTCTGCTGGTGCGGCAGAACTTCATGCTGAACCGGATCC*
*TGAAGTCCATGGACAAGAGCATCGACACCCTGAGCGAGATCAGCGGAGCCGCCGAGCTGGACAGAACCGAGGAA*
*TATGCCCTGGGCGTGGTGGGAGTGCTGGAAAGCTACATCGGCTCCATCAACAACATCACAAAGCAGAGCGCCTG*
*CGTGGCCATGAGCAAGCTGCTGACAGAGCTGAACAGCGACGACATCAAGAAGCTGAGGGACAACGAGGAACTGA*
*ACAGCCCCAAGATCCGGGTGTACAACACCGTGATCAGCTACATTGAGAGCAACCGCAAGAACAACAAGCAGACC*
*ATCCATCTGCTGAAGCGGCTGCCCGCCGACGTGCTGAAAAAGACCATCAAGAACACCCTGGACATCCACAAGTC*
*CATCACCATCAACAATCCCAAAGAAAGCACCGTGTCTGACACCAACGACCACGCCAAGAACAACGACACCACCT*
GATGAGCGGCCGCGATCTG<u>*CTGTGCCTTCTAGTTGCCAGCCATCTGTTGTTTGCCCCTCCCCCGTGCCTTCCTT*</u>
<u>*GACCCTGGAAGGTGCCACTCCCACTGTCCTTTCCTAATAAAATGAGGAAATTGCATCGCATTGTCTGAGTAGGT*</u>
<u>*GTCATTCTATTCTGGGGGGTGGGGTGGGGCAGGACAGCAAGGGGGAGGATTGGGAAGACAATAGCAGGCATGCT*</u>
<u>*GGGGATGCGGTGGGCTCTATGG*</u>
CMV Promoter sequence: bold
Transgene sequence NM2: Italic
bghpolyA PolyA signal: italic+ underline SEQ ID NO: 5 NM2 protein sequence
MALSKVKLNDTLNKDQLLSSSKYTIQRSTGDSIDTPNYDVQKHINKLCGMLLITEDANHKFTGLIGMLYAMSRL
GREDTIKILRDAGYHVKANGVDVTTHRQDINGKEMKFEVLTLASLTTEIQINIEIESRKSYKKMLKEMGEVAPE
YRHDSPDCGMIILCIAALVITKLAAGDRSGLTAVIRRANNVLKNEMKRYKGLLPKDIANSFYEVFEKYPHFIDV
FVHFGIAQSSTRGGSRVEGIFAGLFMNAYGAGQVMLRWGVLAKSVKNIMLGHASVQAEMEQVVEVYEYAQKLGG
EAGFYHILNNPKASLLSLTQFPHFSSVVLGNAAGLGIMGEYRGTPRNQDLYDAAKAYAEQLKENGVINYSVLDL
TAEELEAIKHQLNPKDNDVELGGGGSGGGGMSRRNPCKFEIRGHCLNGKRCHFSHNYFEWPPHALLVRQNFMLN
RILKSMDKSIDTLSEISGAAELDRTEEYALGVVGVLESYIGSINNITKQSACVAMSKLLTELNSDDIKKLRDNE
ELNSPKIRVYNTVISYIESNRKNNKQTIHLLKRLPADVLKKTIKNTLDIHKSITINNPKESTVSDTNDHAKNND
TT SEQ ID NO: 6 Polynucleotide sequence encoding the hCMV F0 WPRE bghpolyA
cassette
CCATTGCATACGTTGTATCCATATCATAATATGTACATTTATATTGGCTCATGTCCAACATTACCGCCATGTTG
ACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGAGTATTTACGGTAAACTGC
CCACTTGGCAGTACATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACGTATTAGTCATCGCT
ATTACCATGGTGATGCGGTTTTGGCAGTACATCAATGGGCGTGGATAGCGGTTTGACTCACGGGGATTTCCAAG
TCTCCACCCCATTGACGTCAATGGGAGTTTGTTTTGGCACCAAAATCAACGGGACTTTCCAAAATGTCGTAACA
ACTCCGCCCCATTGACGCAAATGGGCGGTAGGCGTGTACGGTGGGAGGTCTATATAAGCGAAGCGCTCCCTAT
CAGTGATAGAGATCTCCCTATCAGTGATAGAGATCGTCGACGAGCTCGCGGCGGGCGGGAGTCGCTGCGCGCTG
CCTTCGCCCCGTGCCCCGCTCCGCCGCCGCCTCGCGCCGCCCGCCCCGGCTCTGACTGACCGCGTTACTAAAAC
AGGTAAGTCCGGCCTCCGCGCCGGGTTTTGGCGCCTCCCGCGGGCGCCCCCCTCCTCACGGCGAGCGCTGCCAC
GTCAGACGAAGGGCGCAGCGAGCGTCCTGATCCTTCCGCCCGGACGCTCAGGACAGCGGCCCGCTGCTCATAAG
ACTCGGCCTTAGAACCCCAGTATCAGCAGAAGGACATTTTAGGACGGGACTTGGGTGACTCTAGGGCACTGGTT
TTCTTTCCAGAGAGCGGAACAGGCGAGGAAAAGTAGTCCCTTCTCGGCGATTCTGCGGAGGGATCTCCGTGGGG
CGGTGAACGCCGATGATGCCTCTACTAACCATGTTCATGTTTTCTTTTTTTTTCTACAGGTCCTGGGTGACGAA
*CA*GGATATCGCCACCATGGAACTGCTGATCCTGAAGGCCAACGCCATCACCACCATCCTGACCGCCGTGACCTT
*CTGCTTCGCCAGCGGCCAGAACATCACCGAGGAATTCTACCAGAGCACCTGTAGCGCCGTGAGCAAGGGCTACC*
*TGAGCGCCCTGAGAACCGGCTGGTACACCAGCGTGATCACCATCGAGCTGAGCAACATCAAAGAAAACAAGTGC*
*AACGGCACCGACGCCAAAGTGAAGCTGATCAAGCAGGAACTGGACAAGTACAAGAACGCCGTGACCGAGCTGCA*
*GCTGCTGATGCAGAGCACCCCCGCCACCAACAACCGGGCCAGACGGGAGCTGCCCCGGTTCATGAACTACACCC*
*TGAACAACGCCAAAAAGACCAACGTGACCCTGAGCAAGAAGCGGAAGCGGCGGTTCCTGGGCTTTCTGCTGGGC*
*GTGGGCAGCGCCATTGCCAGCGGCGTGGCCGTGTCTAAGGTGCTGCACCTGGAAGGCGAAGTGAACAAGATCAA*
*GAGCGCCCTGCTGAGCACCAACAAGGCCGTGGTGTCCCTGAGCAACGGCGTGAGCGTGCTGACCAGCAAGGTGC*

DESCRIPTION OF THE SEQUENCES

*TGGATCTGAAGAACTACATCGACAAGCAGCTGCTGCCCATCGTGAACAAGCAGAGCTGCAGCATCAGCAACATC*
*GAGACAGTGATCGAGTTCCAGCAGAAGAACAACCGGCTGCTGGAAATCACCCGGGAGTTCAGCGTGAACGCCGG*
*CGTGACCACCCCTGTGTCCACCTACATGCTGACCAACAGCGAGCTGCTGAGCCTGATCAACGACATGCCCATCA*
*CCAACGACCAGAAAAAGCTGATGAGCAACAACGTGCAGATCGTGCGGCAGCAGAGCTACTCCATCATGTCCATC*
*ATCAAAGAAGAGGTGCTGGCCTACGTGGTGCAGCTGCCCCTGTACGGCGTGATCGACACCCCCTGCTGGAAGCT*
*GCACACCAGCCCCCTGTGCACCACCAACACCAAAGAGGGCAGCAACATCTGCCTGACCCGGACCGACAGAGGCT*
*GGTACTGCGACAACGCCGGCAGCGTGTCATTCTTTCCACAGGCCGAGACATGCAAGGTGCAGAGCAACCGGGTG*
*TTCTGCGACACCATGAACAGCCTGACCCTGCCCTCCGAAGTGAACCTGTGCAACGTGGACATCTTCAACCCCAA*
*GTACGACTGCAAGATCATGACCTCCAAGACCGACGTGTCCAGCTCCGTGATCACCTCCCTGGGCGCCATCGTGT*
*CCTGCTACGGCAAGACCAAGTGCACCGCCAGCAACAAGAACCGGGGCATCATCAAGACCTTCAGCAACGGCTGC*
*GACTACGTGTCCAACAAGGGGGTGGACACCGTGTCCGTGGGCAACACCCTGTACTACGTGAACAAACAGGAAGG*
*CAAGAGCCTGTACGTGAAGGGCGAGCCCATCATCAACTTCTACGACCCCCTGGTGTTCCCCAGCGACGAGTTCG*
*ACGCCAGCATCAGCCAGGTGAACGAGAAGATCAACCAGAGCCTGGCCTTCATCCGGAAGTCCGACGAGCTGCTG*
*CACAATGTGAATGCCGGCAAGTCCACCACCAACTGATGAGCGGCCATCTAA*TCAACCTCTGGATTACAAAATTT*
*GTGAAAGATTGACTGGTATTCTTAACTATGTTGCTCCTTTTACGCTATGTGGATACGCTGCTTTAATGCCTTTG*
*TATCATGCTATTGCTTCCCGTATGGCTTTCATTTTCTCCTTGTATAAATCCTGGTTGCTGTCTCTTTATGA*
*GGAGTTGTGGCCCGTTGTCAGGCAACGTGGCGTGGTGTGCACTGTGTTTGCTGACGCAACCCCCACTGGTTGGG*
*GCATTGCCACCACCTGTCAGCTCCTTTCCGGGACTTTCGCTTTCCCCCTCCCTATTGCCACGGCGGAACTCATC*
*GCCGCCTGCCTTGCCCGCTGCTGGACAGGGGCTCGGCTGTTGGGCACTGACAATTCCGTGGTGTTGTCGGGGAA*
*ATCATCGTCCTTTCCTTGGCTGCTCGCCTGTGTTGCCACCTGGATTCTGCGCGGGACGTCCTTCTGCTACGTCC*
*CTTCGGCCCTCAATCCAGCGGACCTTCCTTCCCGCGGCCTGCTGCCGGCTCTGCGGCCTCTTCCGCGTCTTCGC*
*CTTCGCCCTCAGACGAGTCGGATCTCCCTTTGGGCCGCCTCCCCGCCT**GCGCCGCGAT*CTGCTGTGCCTTCTA*
*GTTGCCAGCCATCTGTTGTTTGCCCCTCCCCCGTGCCTTCCTTGACCCTGGAAGGTGCCACTCCCACTGTCCTT*
*TCCTAATAAAATGAGGAAATTGCATCGCATTGTCTGAGTAGGTGTCATTCTATTCTGGGGGGTGGGGTGGGGCA*
*GGACAGCAAGGGGGAGGATTGGGAAGACAATAGCAGGCATGCTGGGGATGCGGTGGGCTCTATGG*
Enhanced CMV Promoter sequence: bold
Transgene sequence F0: Italic
WPRE sequence: underlined bold
bghpolyA PolyA signal: italic+ underline SEQ ID NO: 7 F0 protein sequence
MELLILKANAITTILTAVTFCFASGQNITEEFYQSTCSAVSKGYLSALRTGWYTSVITIELSNIKENKCNGTDA
KVKLIKQELDKYKNAVTELQLLMQSTPATNNRARRELPRFMNYTLNNAKKTNVTLSKKRKRRFLGFLLGVGSAI
ASGVAVSKVLHLEGEVNKIKSALLSTNKAVVSLSNGVSVLTSKVLDLKNYIDKQLLPIVNKQSCSISNIETVIE
FQQKNNRLLEITREFSVNAGVTTPVSTYMLTNSELLSLINDMPITNDQKKLMSNNVQIVRQQSYSIMSIIKEEV
LAYVVQLPLYGVIDTPCWKLHTSPLCTTNTKEGSNICLTRTDRGWYCDNAGSVSFPQAETCKVQSNRVFCDTM
NSLTLPSEVNLCNVDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLAFIRKSDELLHNVNA
GKSTTN SEQ ID NO: 8 Polynucleotide sequence of the hCMV promoter and enhancer sequence
CCATTGCATACGTTGTATCCATATCATAATATGTACATTTATATTGGCTCATGTCCAACATTACCGCCATGTTGACATTGAT
TATTGACTAGTTATTAATAGTAATCAATTACGGGGTCATTAGTTCATAGCCCATATATGGAGTTCCGCGTTACATAACTTA
CGGTAAATGGCCCGCCTGGCTGACCGCCCAACGACCCCCGCCCATTGACGTCAATAATGACGTATGTTCCCATAGTAAC
GCCAATAGGGACTTTCCATTGACGTCAATGGGTGGAGTATTTACGGTAAACTGCCCACTTGGCAGTACATCAAGTGTATC
ATATGCCAAGTACGCCCCCTATTGACGTCAATGACGGTAAATGGCCCGCCTGGCATTATGCCCAGTACATGACCTTATGG
GACTTTCCTACTTGGCAGTACATCTACGTATTAGTCATCGCTATTACCATGGTGATGCGGTTTTGGCAGTACATCAATGG
GCGTGGATAGCGGTTTGACTCACGGGGATTTCCAAGTCTCCACCCCATTGACGTCAATGGGAGTTTGTTTTGGCACCAAA
ATCAACGGGACTTTCCAAAATGTCGTAACAACTCCGCCCCATTGACGCAAATGGGCGGTAGGCGTGTACGGTGGGAGG
TCTATATAAG SEQ ID NO: 9 Polynucleotide sequence of the Chicken Beta-Actin Fragment
GCGAAGCGCTCCCTATCAGTGATAGAGATCTCCCTATCAGTGATAGAGATCGTCGACGAGCTCGCGGCGGGCGGGAGT
CGCTGCGCGCTGCCTTCGCCCCGTGCCCCGCTCCGCCGCCGCCTCGCGCCGCCCGCCCCGGCTCTGACTGACCGCGTTAC
T SEQ ID NO: 10 Polynucleotide sequence of the the Splice Donor Region
AAAACAGGTAAGTCC SEQ ID NO: 11 Polynucleotide sequence of the the ubiquitin (UBC) enhancer
GGCCTCCGCGCCGGGTTTTGGCGCCTCCCGCGGGCGCCCCCCTCCTCACGGCGAGCGCTGCCACGTCAGACGAAGGGC
GCAGCGAGCGTCCTGATCCTTCCGCCCGGACGCTCAGGACAGCGGCCCGCTGCTCATAAGACTCGGCCTTAGAACCCCA
GTATCAGCAGAAGGACATTTTAGGACGGGACTTGGGTGACTCTAGGGCACTGGTTTTCTTTCCAGAGAGCGGAACAGG
CGAGGAAAAGTAGTCCCTTCTCGGCGATTCTGCGGAGGGATCTCCGTGGGGCGGTGAACGCCGATGAT SEQ ID NO: 12 Polynucleotide sequence of the Splice Acceptor Region
GCCTCTACTAACCATGTTCATGTTTTCTTTTTTTTCTACAGGTCCTGGGTGACGAACAG

The invention claimed is:

1. A promoter comprising:
   an hCMV enhancer sequence;
   (ii) an hCMV promoter sequence;
   (iii) a splice donor region;
   (iv) a cell-derived enhancer sequence; and
   (v) a splice acceptor region.

2. The promoter of claim 1, wherein the cell-derived enhancer sequence is a ubiquitin (UBC) enhancer sequence.

3. The promoter of claim 2, wherein the UBC enhancer comprises the sequence of SEQ ID NO: 11.

4. The promoter of claim 1 comprising one or more of SEQ ID NO: 8, SEQ ID NO:10, SEQ ID NO:11 and SEQ ID NO: 12.

5. The promoter of claim 1, wherein the promoter further comprises a fragment of a chicken beta-actin sequence, wherein the fragment of the chicken beta-actin sequence comprises a 5' untranslated region of a chicken beta actin sequence and does not contain a promoter sequence of the chicken beta-actin sequence.

6. A promoter comprising a nucleic acid sequence having at least 90% identity to SEQ ID NO: 3.

7. The promoter of claim 6, wherein the promoter comprises a nucleic acid sequence having at least about 90%, at least about 95%, at least about 96%, at least about 97%, at least about 98% or at least about 99% sequence identity to SEQ ID NO: 3.

8. The promoter of claim 7, wherein the promoter comprises the nucleic acid sequence of SEQ ID NO: 3.

9. The promoter of claim 8, wherein the promoter consists of the nucleic acid sequence of SEQ ID NO: 3.

10. An adenoviral vector comprising an expression cassette, wherein the expression cassette comprises a transgene and a promoter, wherein the promoter comprises:
    an hCMV enhancer sequence;
    (ii) an hCMV promoter sequence;
    (iii) a splice donor region;
    (iv) a cell-derived enhancer sequence; and
    (v) a splice acceptor region.

11. The adenoviral vector of claim 10, wherein the expression cassette is the first expression cassette, and the adenoviral vector further comprises a second expression cassette, wherein the second expression cassette comprises a transgene and a promoter, wherein the promoter comprises:
    an hCMV enhancer sequence;
    (ii) an hCMV promoter sequence;
    (iii) a splice donor region;
    (iv) a cell-derived enhancer sequence; and
    (v) a splice acceptor region.

12. The adenoviral vector of claim 10, wherein the promoter comprises a nucleic acid sequence having at least 90% identity to SEQ ID NO: 3.

13. The adenoviral vector of claim 10, wherein the cell-derived enhancer sequence is a ubiquitin (UBC) enhancer sequence.

14. The adenoviral vector of claim 10, wherein the promoter comprises one or more of SEQ ID NO: 8, SEQ ID NO:10, SEQ ID NO:11 and SEQ ID NO: 12.

15. The adenoviral vector of claim 10, wherein the promoter comprises a fragment of a chicken beta-actin sequence, wherein the fragment of the chicken beta-actin sequence comprises a 5' untranslated region of a chicken beta actin sequence and does not contain a promoter sequence of the chicken beta-actin sequence.

16. The adenoviral vector of claim 12, wherein the promoter comprises a nucleic acid sequence having at least about 95%, at least about 96%, at least about 97%, at least about 98% or at least about 99% sequence identity to SEQ ID NO: 3.

* * * * *

UNITED STATES PATENT AND TRADEMARK OFFICE
CERTIFICATE OF CORRECTION

PATENT NO. : 11,352,643 B2
APPLICATION NO. : 16/756373
DATED : June 7, 2022
INVENTOR(S) : Stefano Colloca It is certified that error appears in the above-identified patent and that said Letters Patent is hereby corrected as shown below:

In the Claims

Column 85, Line 10, Claim 1:
Change: "an hCMV enhancer sequence;"
To: -- (i) an hCMV enhancer sequence; --

Column 85, Lines 31-32, Claim 7:
Change: "a nucleic acid sequence having at least about 90%, at least about 95%,"
To: -- a nucleic acid sequence having at least about 95%, --

Column 86, Line 8, Claim 10:
Change: "an hCMV enhancer sequence;"
To: -- (i) an hCMV enhancer sequence; --

Column 86, Line 18, Claim 11:
Change: "an hCMV enhancer sequence;"
To: -- (i) an hCMV enhancer sequence; --

Signed and Sealed this
Ninth Day of August, 2022

Katherine Kelly Vidal
*Director of the United States Patent and Trademark Office*